US010274717B2

(12) United States Patent
Togino

(10) Patent No.: US 10,274,717 B2
(45) Date of Patent: Apr. 30, 2019

(54) OPTICAL SYSTEM, STEREOSCOPIC IMAGING DEVICE, AND ENDOSCOPE

(71) Applicant: OLYMPUS CORPORATION, Hachioji-shi, Tokyo (JP)

(72) Inventor: Takayoshi Togino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 222 days.

(21) Appl. No.: 15/208,653

(22) Filed: Jul. 13, 2016

(65) Prior Publication Data
US 2016/0320606 A1 Nov. 3, 2016

Related U.S. Application Data

(63) Continuation of application No. PCT/JP2014/076968, filed on Oct. 8, 2014.

(30) Foreign Application Priority Data

Jan. 15, 2014 (JP) .................................. 2014-005019

(51) Int. Cl.
*G02B 23/24* (2006.01)
*G02B 23/18* (2006.01)
(Continued)

(52) U.S. Cl.
CPC ...... *G02B 23/2415* (2013.01); *A61B 1/00193* (2013.01); *G02B 13/001* (2013.01);
(Continued)

(58) Field of Classification Search
CPC .. G02B 23/2415; G02B 23/18; G02B 23/243; G02B 13/001; G02B 27/0025; A61B 1/00193
(Continued)

(56) References Cited

U.S. PATENT DOCUMENTS 2,268,338 A * 12/1941 Kober .................... G03B 35/00
352/57
4,862,873 A * 9/1989 Yajima ............... A61B 1/00193
348/45
(Continued)

FOREIGN PATENT DOCUMENTS

CN 103026295 A 4/2013
JP 08056891 A 3/1996
(Continued)

OTHER PUBLICATIONS

Chinese Office Action dated Dec. 4, 2017 issued in counterpart Chinese Application No. 201480073186.1.
(Continued)

*Primary Examiner* — William R Alexander
(74) *Attorney, Agent, or Firm* — Holtz, Holtz & Volek PC

(57) ABSTRACT

An optical system 1 includes, in order from an object side to an image plane side, a front group Gf including a first front group Gf1 arranged centering a first front central axis Cf1 and a second front group Gf2 arranged centering a second front group central axis Cf2 as a rotation symmetry axis extending parallel to the first front group central axis Cf1; and a back group Gb arranged centering a single back group central axis Cb. A central principal ray of a first light beam L1 that has passed through the first front group Gf1 and a central principal ray of a second light beam L2 that has passed through the second front group Gf2 do not cross each other from when they exit from the back group Gb to when they reach the image plane.

19 Claims, 45 Drawing Sheets

(51) Int. Cl.
*A61B 1/00* (2006.01)
*G03B 35/10* (2006.01)
*G02B 13/00* (2006.01)
*G02B 27/00* (2006.01)

(52) U.S. Cl.
CPC ........... *G02B 23/18* (2013.01); *G02B 23/243* (2013.01); *G02B 27/0025* (2013.01); *G03B 35/10* (2013.01)

(58) Field of Classification Search
USPC .......................................... 359/363, 376, 377
See application file for complete search history.

(56) References Cited

U.S. PATENT DOCUMENTS

| | | | | |
|---|---|---|---|---|
| 5,459,605 | A | * | 10/1995 | Kempf ............... A61B 1/00165 359/462 |
| 5,860,912 | A | * | 1/1999 | Chiba ............... A61B 1/00059 348/45 |
| 5,971,915 | A | | 10/1999 | Yamamoto et al. |
| 6,104,426 | A | * | 8/2000 | Street ................. G02B 23/2415 348/45 |
| 6,383,131 | B1 | | 5/2002 | Yamamoto et al. |
| 6,396,627 | B1 | * | 5/2002 | Tachihara ............. G02B 21/22 348/42 |
| 7,586,675 | B2 | * | 9/2009 | Sander .................... G02B 3/10 359/368 |
| 2005/0185050 | A1 | | 8/2005 | Ohashi |
| 2010/0208046 | A1 | | 8/2010 | Takahashi |
| 2013/0022344 | A1 | * | 1/2013 | Bae ..................... G02B 27/123 396/324 |
| 2013/0127997 | A1 | * | 5/2013 | Inomoto ................ H04N 13/02 348/46 |
| 2013/0170029 | A1 | | 7/2013 | Morita et al. |
| 2014/0177043 | A1 | | 6/2014 | Togino et al. |
| 2016/0070094 | A1 | | 3/2016 | Togino |
| 2016/0370571 | A1 | * | 12/2016 | Togino ..................... G02B 5/04 |

FOREIGN PATENT DOCUMENTS

| | | |
|---|---|---|
| JP | 08122665 A | 5/1996 |
| JP | 2001147382 A | 5/2001 |
| JP | 2001221961 A | 8/2001 |
| JP | 2003005096 A | 1/2003 |
| JP | 4093503 B2 | 6/2008 |
| JP | 4248771 B2 | 4/2009 |
| JP | 2012220848 A | 11/2012 |
| WO | 2013108500 A1 | 7/2013 |
| WO | 2014147856 A1 | 9/2014 |

OTHER PUBLICATIONS

International Search Report (ISR) dated Jan. 6, 2015 issued in International Application No. PCT/JP2014/076968.
Extended European Search Report (EESR) dated Jun. 30, 2017 issued in counterpart European Application No. 14878996.9.

* cited by examiner

Example 1

Example 1

Example2

Example2

Example3

FIG.19 Example 4

Example4

FIG.21 Example5

Example 5

Example6

Example6

Example6

Example6

FIG.28 Example 7

Example 7

Example 7

Example 7

FIG.33 Example 8

Example 8

Example8

Example8

FIG.37 Example9

Example9

Example9

FIG.41 Example 10

Example 10

Example 10

Example 10

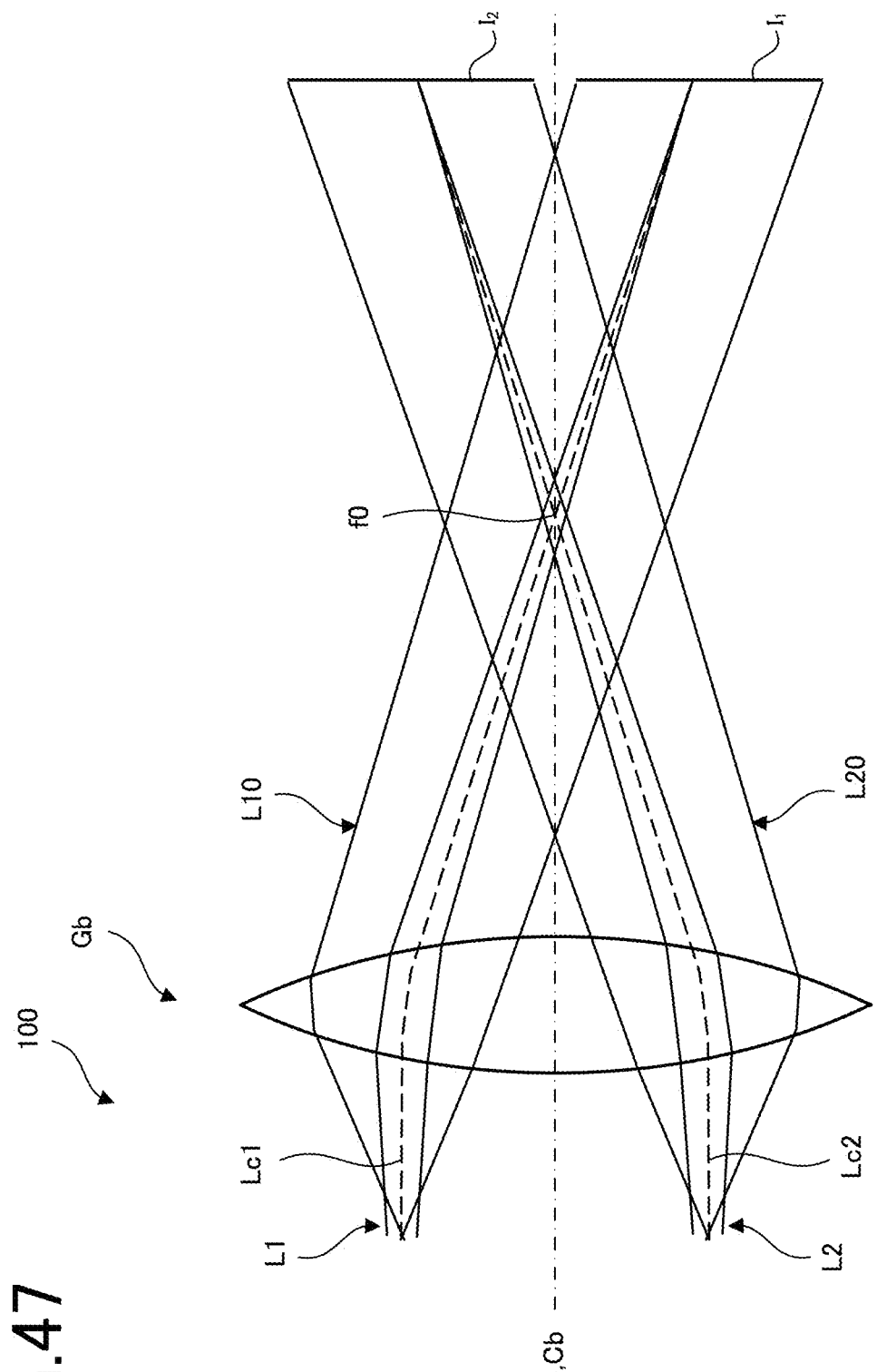

OPTICAL SYSTEM, STEREOSCOPIC IMAGING DEVICE, AND ENDOSCOPE

CROSS-REFERENCE TO RELATED APPLICATIONS

This application is a continuation claiming priority on the basis of Japan Patent Application No. 2014-005019 applied in Japan on Jan. 15, 2014 and based on PCT/JP2014/076968 filed on Oct. 8, 2014. The contents of both the PCT application and the Japan Application are incorporated herein by reference.

BACKGROUND OF THE INVENTION AND RELATED ART STATEMENT

The present invention relates to an optical system, a stereoscopic imaging device, and an endoscope.

There is conventionally disclosed a method for stereoscopic vision, in which two images having different parallaxes are formed on substantially the same plane and then imaged (see JP 08-122665A, Japanese Patent No. 4,248,771, Japanese Patent No. 4,093,503 and JP 2001-147382A).

SUMMARY OF INVENTION

An optical system according to an embodiment of the present invention includes, in order from an object side to an image plane side, a front group including a first front group arranged centering a first front central axis and a second front group arranged centering a second front group central axis extending parallel to the first front group central axis and a back group arranged centering a single back group central axis, wherein a central principal ray of a first light beam that has passed through the first front group and a central principal ray of a second light beam that has passed through the second front group do not cross each other from when they exit from the first and second front groups, respectively, to when they reach the image plane, the first and second light beams are convergent light beams that do not cross each other from when they exit from the first and second front groups, respectively, to when they reach the image plane, an interval between the first and second front group central axes is larger than an interval between the centers of the first and second light beams at the image plane, and the first and second front groups each include a stop.

A stereoscopic imaging device according to an embodiment of the present invention includes the above-described optical system and an imaging device.

An endoscope according to an embodiment of the present invention includes the above-described stereoscopic imaging device.

BRIEF DESCRIPTION OF DRAWINGS

FIG. 47 is a view illustrating, as a reference example, a portion around an image plane of an optical system.

DESCRIPTION OF EMBODIMENTS

Hereinafter, an optical system 1 according to an embodiment of the present invention will be described.

Figure 1:
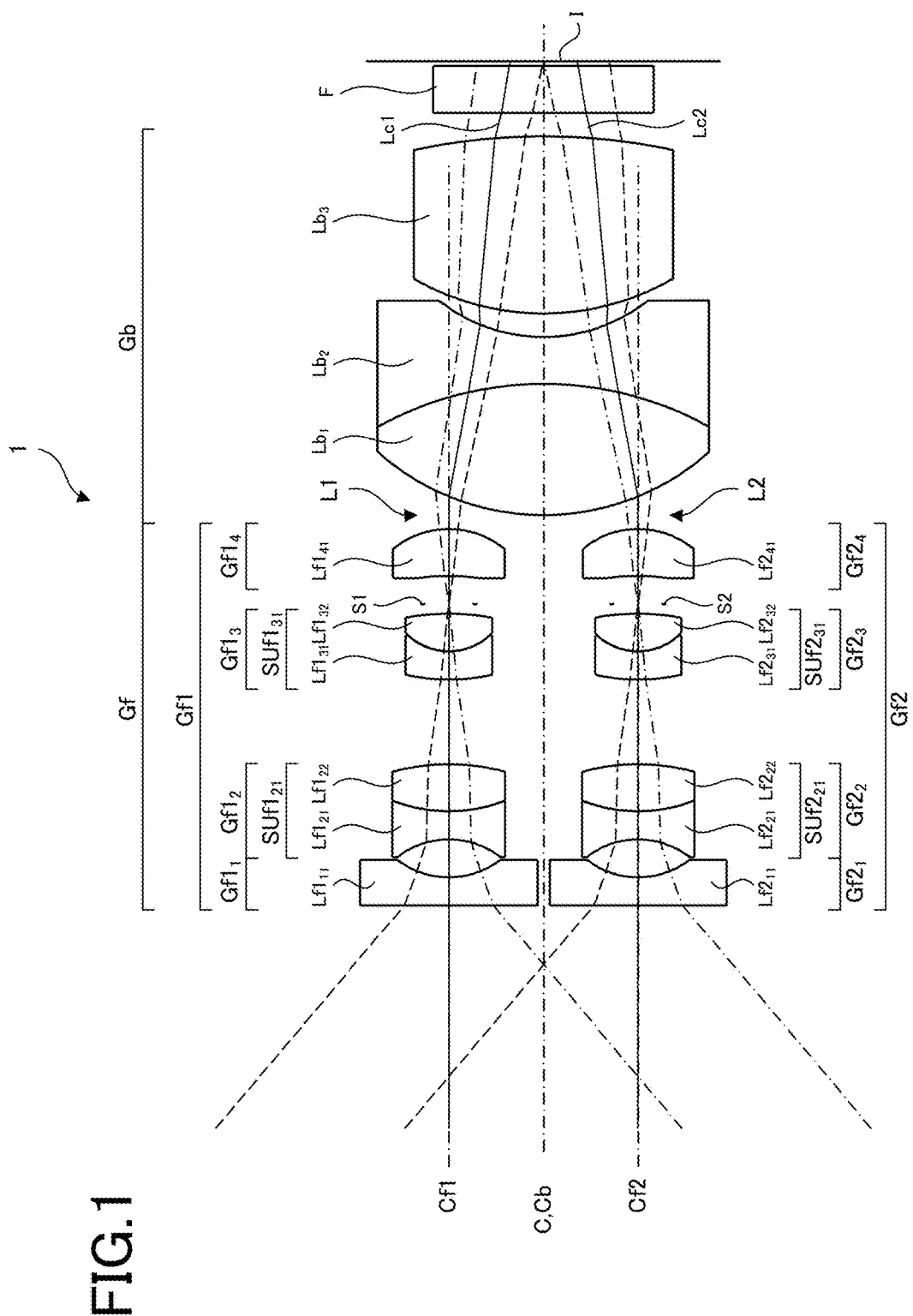
FIG. 1 is a cross-sectional view of an optical system 1 according to an embodiment taken along a central axis C thereof.

FIG. 1 is a cross-sectional view of the optical system 1 according to an embodiment taken along a central axis C thereof.

The optical system 1 according to the present embodiment includes a front group Gf and a back group Gb, in order from an object side. The front group Gf includes a first front group Gf1 having a first front group central axis Cf1 and a second front group Gf2 having a second front group central axis Cf2 extending parallel to the first front group central axis Cf1. The back group Gb has a single back group central axis Cb. A central principal ray of a first light beam L1 that has passed through the first front group Gf1 and a central principal ray of a second light beam L2 that has passed through the second front group Gf2 are preferably convergent light beams that do not cross each other from when they exit from the back group Gb to when they reach the image plane I.

In the optical system 1 according to the present embodiment, the first light beam L1 and second light beam L2 are preferably convergent light beams that do not cross each other from when they exit from the back group Gb to when they reach the image plane I.

A stereoscopic imaging system includes the following four types.

(1) Optical system having two central axes completely independent of each other.

(2) Optical system including, in order from the object side, a front group having one central axis and a back group having two central axes.

(3) Optical system including, in order from the object side, a front group having two central axes and a back group having one central axis.

(4) Optical system having one central axis and obtaining a parallax by pupil division.

In the optical system of (1), imaging devices are required for two respective central axes, resulting in an increase in the device size. In the optical systems of (2) and (4), in order to obtain a wide view angle, it is necessary to dispose a strong negative lens on the object side, resulting in failing to obtain a long base length. The optical system of (3) is a type often adopted for a small-sized stereoscopic imaging device but has a drawback in that the entire length of the optical system is disadvantageously increased.

In recent years, imaging devices having a small size and a large number of pixels have been put into practical use, so that high-resolution image can be performed despite small image height. Thus, the present embodiment assumes use of a small-sized imaging device and aims to provide an optical system having a small size and capable of obtaining a stereoscopic image with a high resolution and a wide observation view angle.

Figure 2:
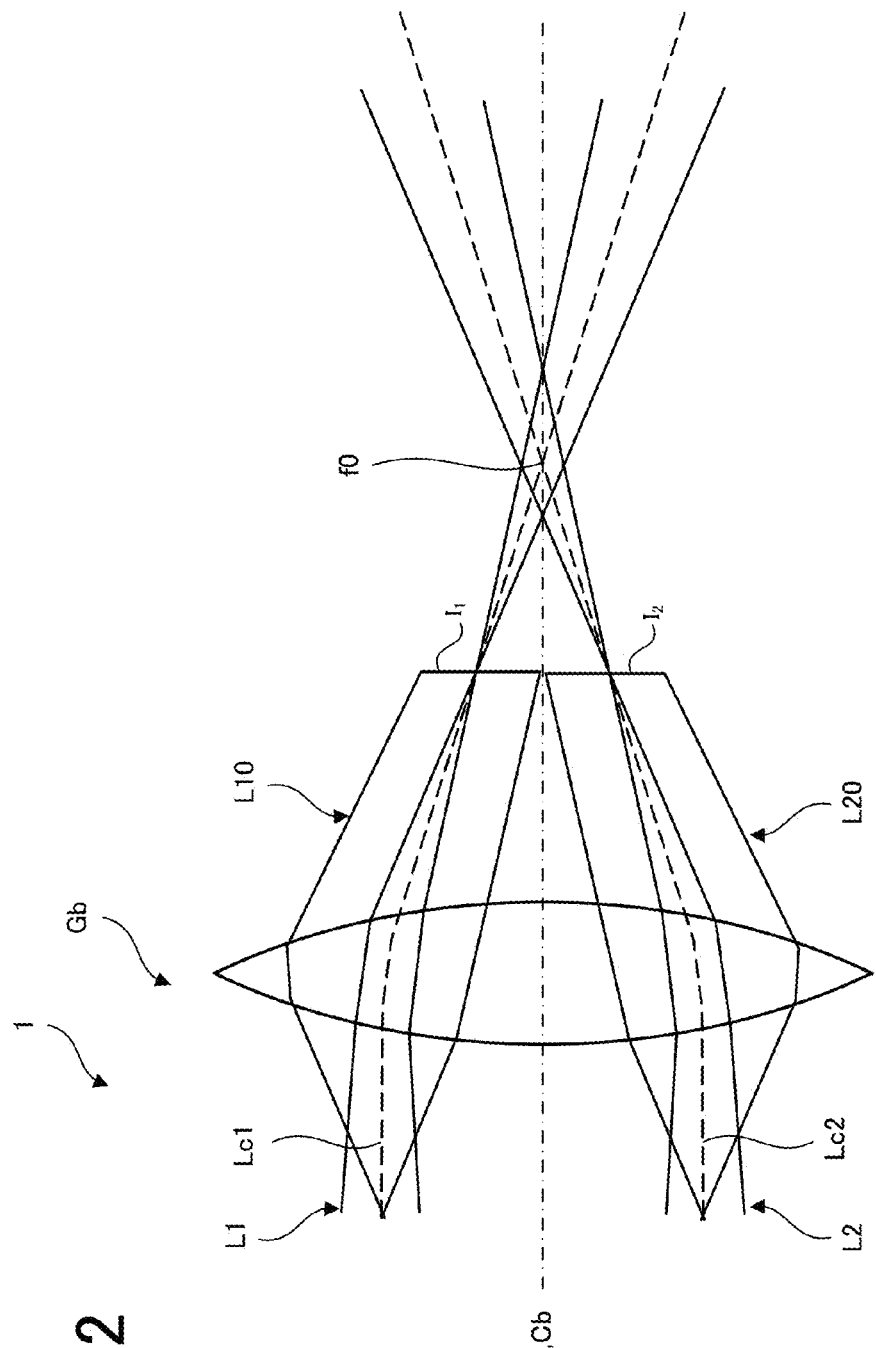
FIG. 2 is a view illustrating a portion around an image plane of the optical system 1 according to the embodiment.

FIG. 2 is a view illustrating a portion around the image plane I of the optical system 1 according to the embodiment. FIG. 47 is a view illustrating a reference example of a portion around an image plane of an optical system. In FIGS. 2 and 47, the back group Gb is schematically illustrated.

The optical system 1 illustrated in FIG. 2 and an optical system 100 as a reference example illustrated in FIG. 47 each include, in order from the object side, an unillustrated front group and a back group Gb. In FIGS. 2 and 47, a left side is set as a front side, and a right side is set as a back side.

Light beams enter, in parallel, the back group Gb from the unillustrated front group having two optical axes. Then, parallel first and second central principal rays Lc1 and Lc2 of the respective first and second light beams L1 and L2 pass through the back group Gb and cross each other at a position backward of the back group Gb. This is because a focal position f0 of the first light beam L1 and second light beam L2 that have entered the back group Gb is the position backward of the back group Gb. When on-axis light beams L10 and L20 exiting from the front group are parallel beams, images of the first light beam L1 and second light beam L2 are formed overlapping the focal position f0 backward of the back group Gb, so that a stereoscopic image cannot be taken.

In the optical system 100 illustrated in FIG. 47, the on-axis light beams L10 and L20 are each made to diverge to make the images be formed at a position backward of the focal position f0, whereby a first imaging plane I₁ and a second imaging plane I₂ are aligned side by side. This method is effective when an image size needs to be comparatively increased, and by increasing a distance from the back group Gb to the imaging planes $I_1$ and $I_2$, the size of an image to be formed can be increased unlimitedly. In this case, light paths cross each other, so that it is possible to ensure a large imaging plane without enlarging the outer diameter of the optical system 100.

In the present embodiment, contrary to the above idea, the image formation is made to occur at a position forward of the focal position f0 backward of the back group Gb, whereby the left and right images can be aligned side by side. As illustrated in FIG. 2, the first central principal ray Lc1 and second central principal ray Lc2 going out of the unillustrated front group cross each other at the focal position f0 backward of the back group Gb as in the case of the reference example illustrated in FIG. 47.

In the present embodiment, the image formation is made to occur at a position closer to the back group Gb than to the focal position f0, so that the light paths do not cross each other before the first imaging plane $I_1$ and second imaging plane $I_2$. In order to make the image formation occur forward of the focal position f0 backward of the back group Gb, it is important to make the on-axis light beams L10 and L20 exiting from the front group converge, contrary to the reference example illustrated in FIG. 47.

When the image formation is made to occur at a position closer to the back group Gb than to the focal position f0 rearward of the back group Gb, the imaging planes $I_1$ and $I_2$ can be reduced in size, resulting in good compatibility with a recent small-sized high definition imaging device. This further allows the distance from the back group Gb to the imaging planes $I_1$ and $I_2$ to be significantly reduced as compared to conventional approaches, whereby it is possible to reduce the entire length of the optical system 1 and that of a system using the optical system 1.

Further, in the present embodiment, as illustrated in FIG. 1, an interval between the first front group central axis Cf1 and the second front group central axis Cf2 is larger than an interval between the first central principal ray Lc1 of the first light beam L1 at the image plane I and the second central principal ray Lc2 of the second light beam L2 at the image plane I. In other words, a center interval between images is preferably smaller than an interval between entrance pupils of an optical system.

In order to obtain a natural-looking stereoscopic image when stereoscopic viewing is performed at a physical distance of several mm to several hundred mm, it is preferable to give a parallax amount corresponding to that obtained when a human performs observation with his or her both eyes in normal cases. For example, when an observer with a pupil distance of 6 cm performs stereoscopic viewing at a distance of 50 cm from a target, a convergence angle is about 7°. Thus, in order to obtain the equivalent convergence angle in a stereoscopic imaging optical system where magnified observation is made at a distance of 15 mm from a target, it is necessary to make an optical-axis interval closer to about 1.8 mm.

However, when the first front group Gf1 and second front group Gf2 are arranged side by side with the interval between central axes made equal to or less than 1.8 mm, an Fno of an optical system becomes large, making it difficult to achieve high resolution imaging. Further, it is difficult to arrange small-sized imaging devices at positions spaced apart from each other on the image plane I, when considering disadvantage in terms of assembling and adjustment of the components. Thus, in the present embodiment, the center interval between images is made smaller than the interval between entrance pupils so as to respond to an imaging device having a small size and a large number of pixels. With such a configuration, a small-sized optical system can be obtained.

Figure 3:
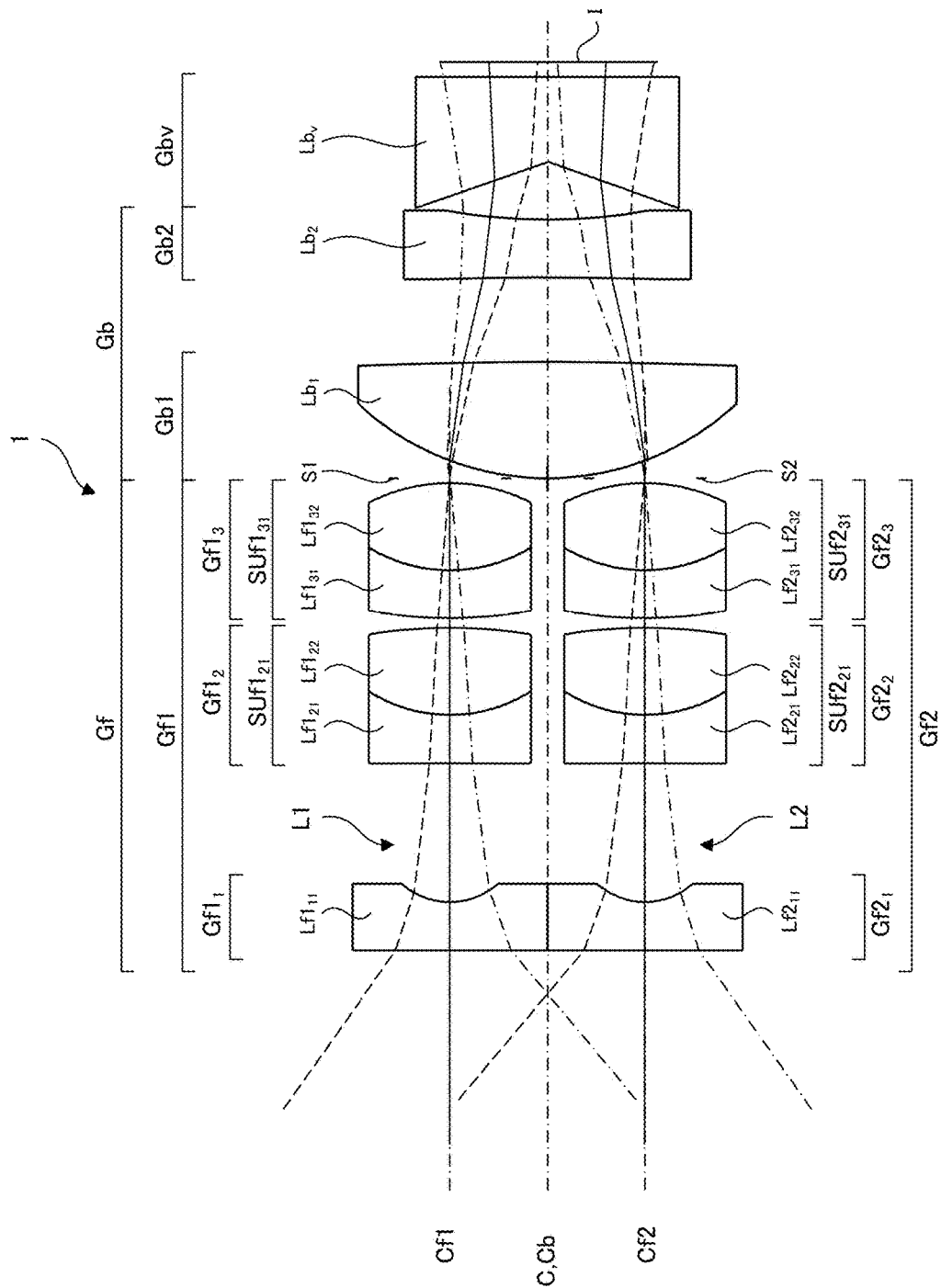
FIG. 3 is a cross-sectional view of the optical system 1 of the embodiment having a back deflection group taken along the central axis C of the optical system 1.

FIG. 3 is a cross-sectional view of the optical system 1 of the embodiment having a back deflection group taken along the central axis C of the optical system 1.

The present embodiment preferably includes a back deflection group Gbv which is disposed between the back group Gb and the image plane I and configured to deflect the first light beam L1 and second light beam L2. The back deflection group Gbv preferably performs deflection so as to reduce convergence of the first light beam L1 and second light beam L2 that have exited from the back group Gb and to make an absolute value of an incident angle of the first and second light beams L1 and L2 onto the image plane I smaller than an absolute value of an incident angle thereof onto the back deflection group Gbv.

In the present embodiment, the first light beam L1 and second light beam L2 exit from their corresponding front groups Gf in a convergent manner to form an image on the image plane I in front of focal positions, with the result that the first light beam L1 and second light beam L2 obliquely enter the image plane I. Recent high-resolution and high-sensitivity imaging devices that use a micro-lens array has incident angle characteristics, so that a problem of insufficient light amount around the image or color blur may occur unless emission characteristics of the optical system is made to respond to the incident angle characteristics of the image plane I. Thus, the back deflection group is disposed so as to deflect the first light beam L1 and second light beam L2 tilted toward the back group central axis Cb in a direction away from the back group central axis Cb. With such a configuration, a small-sized and high-resolution optical system can be obtained.

Further, in the present embodiment, the back deflection group Gbv may include a first back deflection group for deflecting the first light beam L1 and a second back deflection group for deflecting the second light beam L2.

By separately forming the first back deflection group and second back deflection group corresponding respectively to the first light beam L1 and second light beam L2, each deflection group can be rotated in a plane perpendicular to the back group central axis Cb, thereby allowing the deflection to be changed by a very small amount. This allows fine movement of the image center in the image plane I, thereby allowing fine adjustment of the centers of the first and second light beams L1 and L2.

Figure 4:
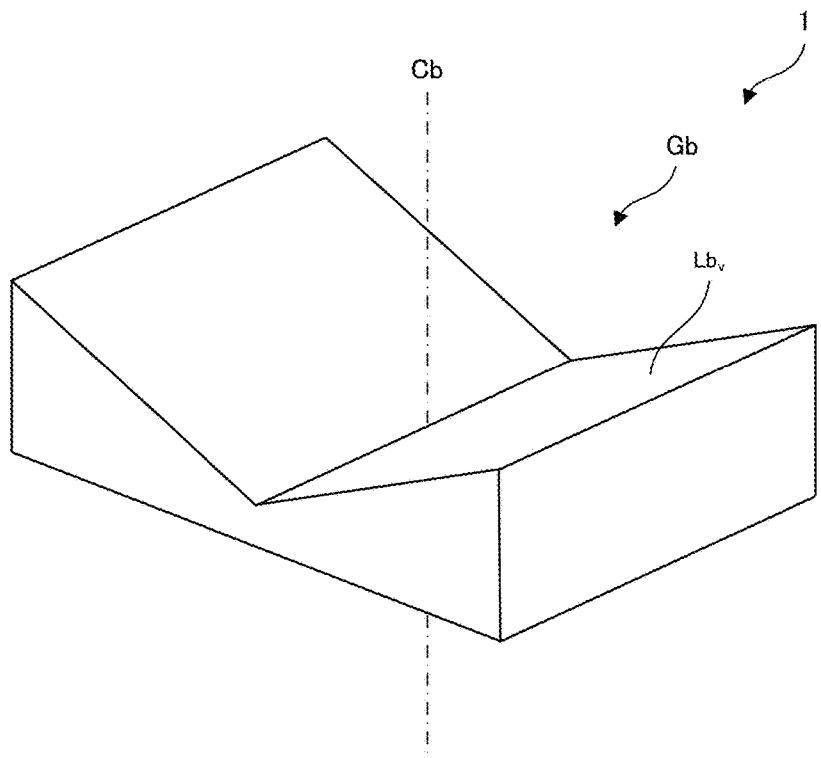
FIG. 4 is a view illustrating an example in which a back deflection member Lbv of the optical system 1 according to the embodiment is formed into a wedge prism shape.

FIG. 4 is a view illustrating an example in which a back deflection member Lbv of the optical system 1 according to the embodiment of the present invention is formed into a wedge prism shape.

In the present embodiment, the back deflection group Gbv preferably includes the back deflection member Lbv, and the back deflection member Lbv is preferably an optical device having a thickness in a direction of the back group central axis Cb which increases toward an outer peripheral side with respect to the back group central axis Cb.

Using the back deflection member Lbv having a refraction function to constitute the back deflection group Gbv allows the back deflection group Gbv to be formed by polishing or molding, thereby making it possible to significantly improve productivity.

Further, in the present embodiment, the back deflection member Lbv is preferably an optical device having a wedge prism shape.

Forming the back deflection member Lbv into a wedge prism shape allows both surfaces of the back deflection member Lbv to be formed as a plane, thereby making it possible to significantly improve productivity.

Figure 5:
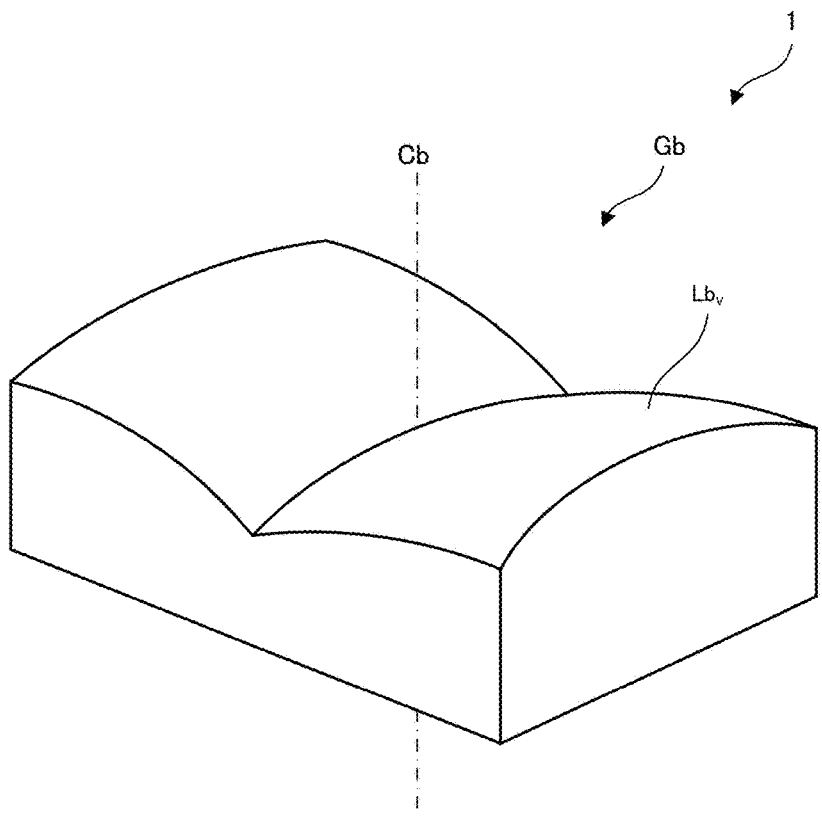
FIG. 5 is a view illustrating an example in which the back deflection member Lbv of the optical system 1 according to the embodiment includes a curved surface.
Figure 6A:
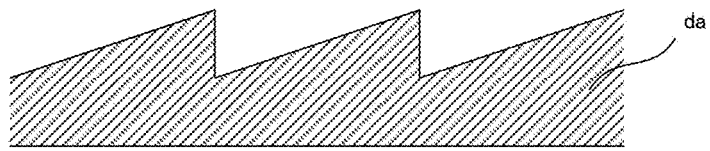
FIGS. 6A to 6D are views each illustrating an example of a diffraction grating included in the back deflection group Gbv of the optical system 1 according to the embodiment.
Figure 6B:
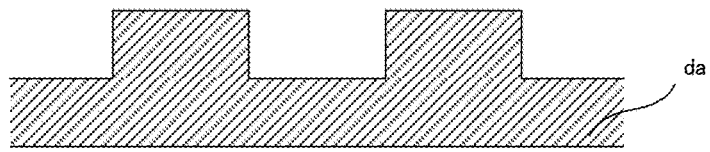
Figure 6C:
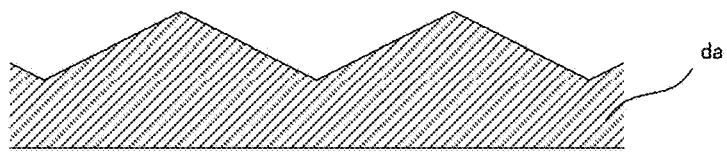
Figure 6D:
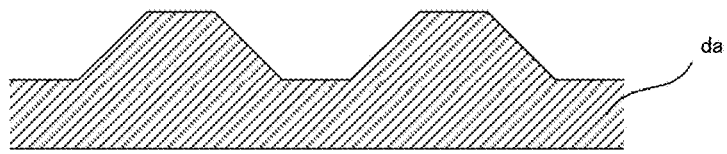

FIG. 5 is a view illustrating an example in which the back deflection member Lbv of the optical system 1 according to the embodiment of the present invention includes a curved surface.

Further, in the present embodiment, the back deflection group Gbv preferably includes an optical device having a curved surface.

When the back deflection member Lbv includes a curved surface, it is possible to set more freely an angle of the light beam entering into the image plane. This can further improve telecentricity of the principal ray with respect to image height after the principal ray exits from the back group Gb and image plane curvature. More preferably, the curved surface may be a spherical surface, a toric surface, an anamorphic surface, or a free-form surface.

FIGS. 6A to 6D are views each illustrating an example of a diffraction grating included in the back deflection group Gbv of the optical system 1 according to the embodiment of the present invention.

Further, in the present embodiment, the back deflection group Gbv may include a diffraction optical device da. As illustrated in FIGS. 6A to 6D, the diffraction optical device da may have any shape. When the back deflection group Gbv includes the diffraction optical device da, tilt of the image plane is reduced, and occurrence of coma aberration is suppressed. This reduces a burden involved in aberration correction in the back group Gb and allows further miniaturization of the optical system.

Figure 7:
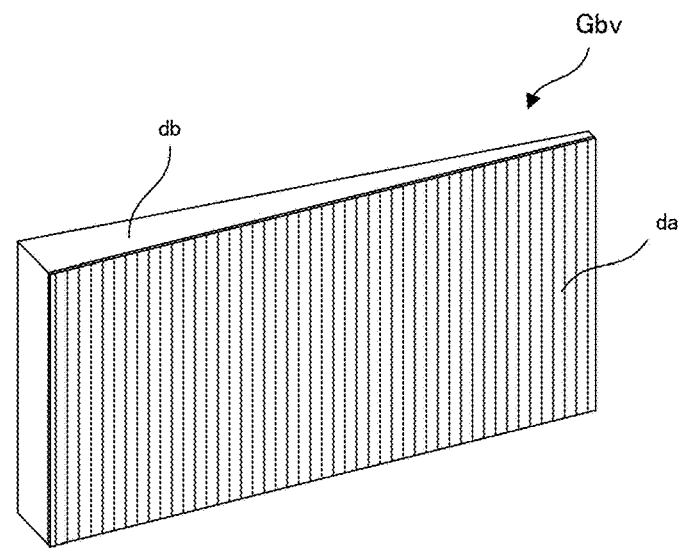
FIG. 7 is a view illustrating an example in which a diffraction grating is attached to a wedge prism included in the back deflection group Gbv of the optical system 1 according to the embodiment.

FIG. 7 is a view illustrating an example in which a diffraction grating is joined to the wedge prism included in the back deflection group Gbv of the optical system 1 according to the embodiment of the present invention.

As illustrated in FIG. 7, the back deflection member Lbv and diffraction optical device da may be joined to each other. Further, as illustrated in FIGS. 6A to 6D, the diffraction optical device da may have any shape.

Using the back deflection member Lbv and diffraction optical device da can suppress occurrence of chromatic aberration and enhance resolving power. At the same time, the entire length of the stereoscopic imaging optical system 1 can be reduced.

Further, as illustrated in FIG. 1, in the optical system 1 according to the present embodiment, the first front group Gf1 preferably includes, in order from the object side, a first group $Gf1_1$ including a flat-concave negative lens $Lf1_{11}$ and a second group $Gf1_2$ including a cemented positive lens $SUf1_{21}$. Similarly, the second front group Gf2 preferably includes, in order from the object side, a first group $Gf2_1$ including a flat-concave negative lens $Lf2_{11}$ and a second group $Gf2_2$ including a cemented positive lens $SUf2_{21}$.

As illustrated in FIG. 2, when the on-axis light beams L10 and L20 that have exited from the front groups Gf are made converge, a burden on the front group Gf is increased. That is, in order to take in light beams from an object point having a wide view angle and to make the light beams converge without generating aberration, a strong positive refractive power and high aberration correction function are required of the front group Gf. To meet this requirement, as illustrated in FIG. 1, the first front group Gf1 and second front group Gf2 preferably include, the front first groups $Gf1_1$ and $Gf2_1$, respectively, each having a strong negative refractive power for taking in light beams having a wide view angle and reducing an angle of an off-axis principal ray and front second groups $Gf1_2$ and $Gf2_2$, respectively, each including a cemented positive lens for strongly correcting magnification chromatic aberration generated in the front first groups $Gf1_1$ and $Gf2_1$. For example, the first front group Gf1 and second front group Gf2 preferably include, respectively, the front first groups $Gf1_1$ and $Gf2_1$ including the flat-concave negative lenses $Lf1_{11}$ and $Lf2_{11}$, respectively, and front second groups $Gf1_2$ and $Gf2_2$ including the cemented meniscus lenses $SUf1_{21}$ and $SUf2_{21}$, respectively, whose concave surfaces face the object side.

Further, in the optical system 1 according to the present embodiment, the first front group Gf1 and second front group Gf2 preferably include, respectively, on the back group Gb side of the front second groups $Gf1_2$ and $Gf2_2$, front third groups $Gf1_3$ and $Gf2_3$ including cemented positive lenses $SUf1_{31}$ and $SUf2_{31}$, respectively, which are different from those of the front second groups $Gf1_2$ and $Gf2_2$.

Light beams whose view angle is reduced by the front first groups $Gf1_1$ and $Gf2_1$ and front second groups $Gf1_2$ and $Gf2_2$ of the front group Gf become convergent light beams by the front third groups $Gf1_3$ and $Gf2_3$ of the front group Gf. Therefore, a large burden is imposed on the front group Gf, so that the first front group Gf1 and second front group Gf2 preferably include, respectively, front third groups $Gf1_3$ and $Gf2_3$ that correct at least on-axis chromatic aberration by the cemented lens. Further, the first front group Gf1 and second front group Gf2 preferably include, respectively, front fourth groups $Gf1_4$ and $Gf2_4$ each including a single positive lens.

Figure 8:
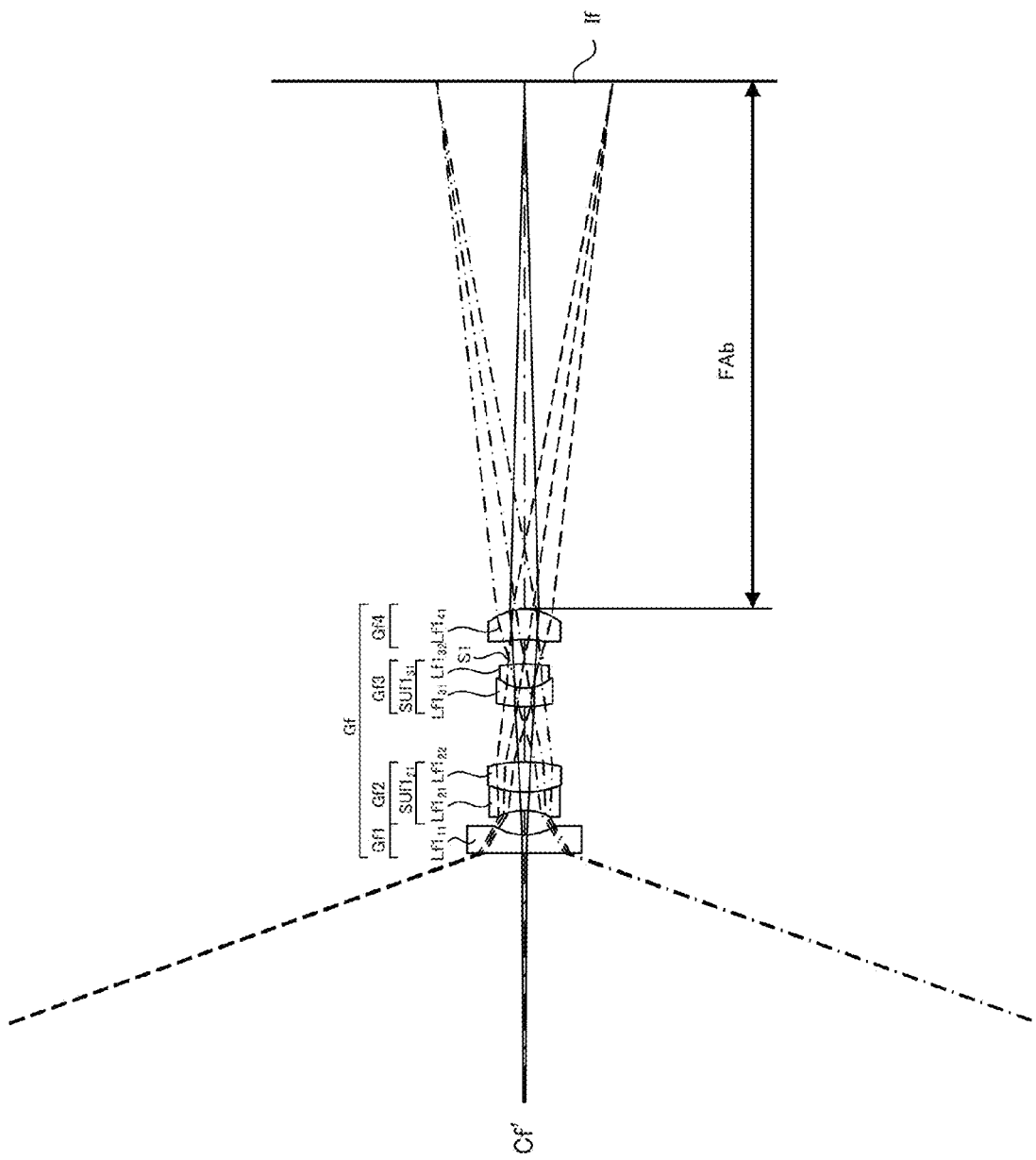
FIG. 8 is a view for explaining a position of an image formed only by a front group Gf of the optical system 1 according to the embodiment.
Figure 9:
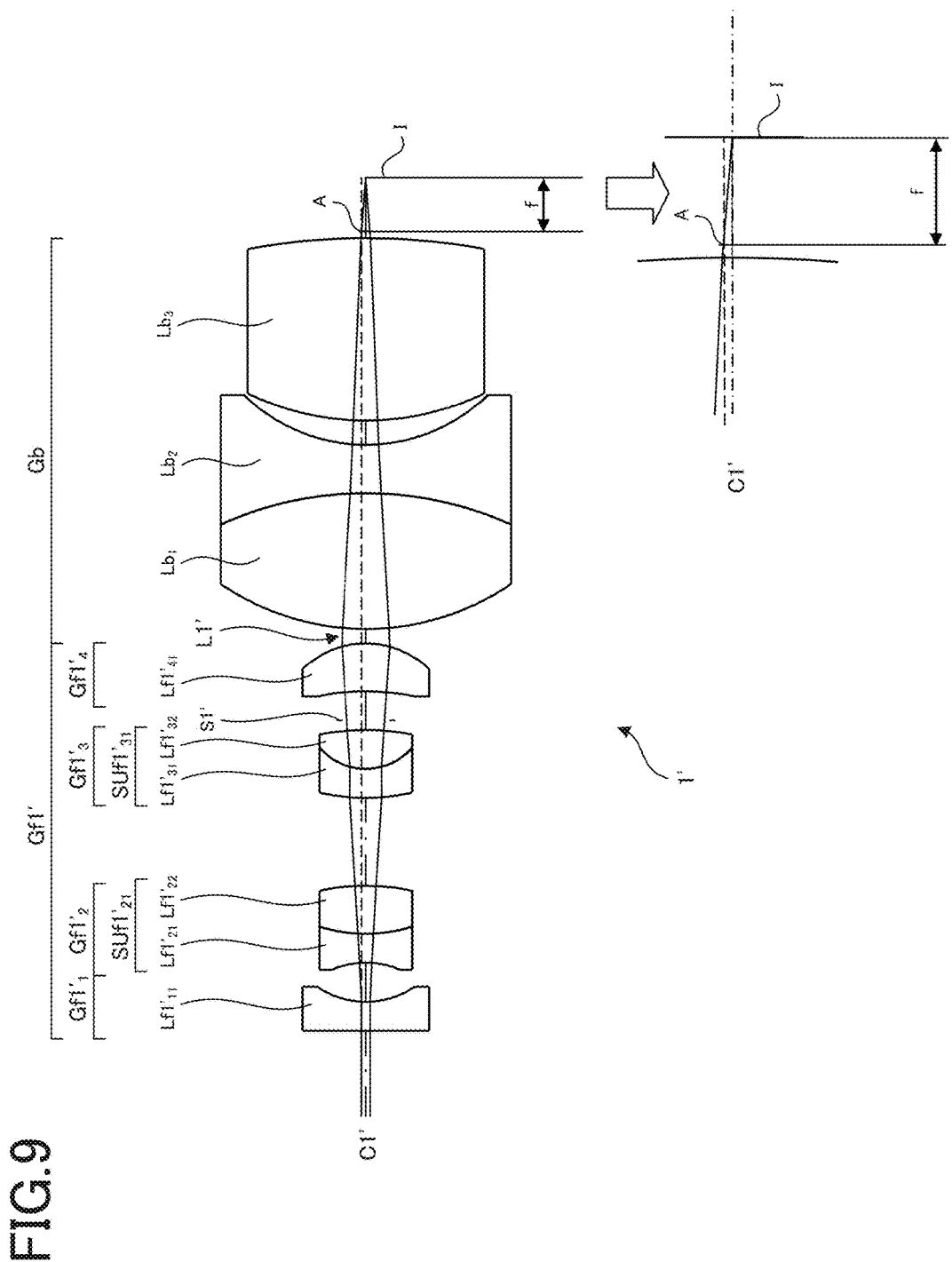
FIG. 9 is a view for explaining a focal distance $\underline{f}$ of the optical system 1 according to the embodiment.

FIG. 8 is a view for explaining a position of an image formed only by the front group Gf of the optical system 1 according to the embodiment of the present invention. FIG. 9 is a view for explaining a focal distance $\underline{f}$ of the optical system 1 according to the embodiment of the present invention.

The optical system 1 according to the present embodiment preferably satisfies the following conditional formula (1):

$$FAb/f < 50 \quad (1)$$

where FAb is a distance from a final surface of the front group Gf to an image formation position at which light beams exiting from the front group Gf are image-formed, and $\underline{f}$ is a focal distance of the entire optical system.

In the present embodiment, as illustrated in FIG. 8, a distance from a final surface of the front group Gf to an image formation position If at which light beams exiting from the front group Gf are image-formed is FAb. Further, as illustrated in FIG. 9, a focal distance of the entire optical system 1 is f. When the optical system 1 is an eccentric optical system, parallel light beams are made to enter the optical system 1 from an infinity after removal of eccentricity. Then, an on-axial marginal ray L1' having entered into the optical system 1 exits from the optical system 1 after passing therethrough, and arrives at a position A where it bends virtually. A distance from the position A to the image plane I is defined as the focal distance f.

When the upper limit of the conditional formula (1) is exceeded, a distance from the back group Gb to the image formation position is increased to increase the entire length of the optical system 1.

More preferably, the optical system 1 according to the present embodiment satisfies the following conditional formula (1'):

$$Fab/f < 10 \quad (1')$$

When the above conditional formula (1') is satisfied, the distance from the back group Gb to the image formation position is further reduced to further reduce the entire length of the optical system 1.

Figure 10:
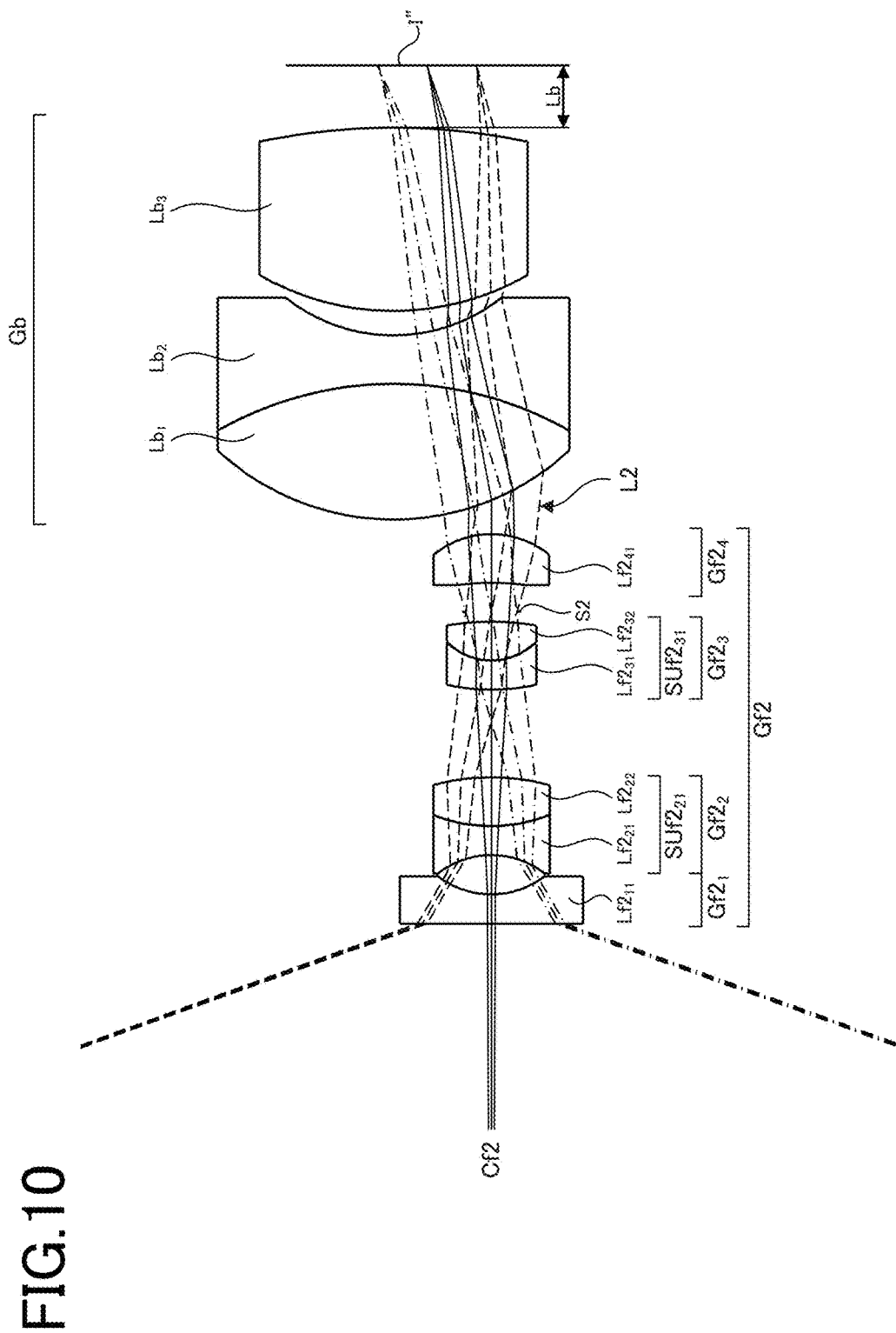
FIG. 10 is a view for explaining a position of an image in a state where a filter F of the optical system 1 according to the embodiment is removed.

FIG. 10 is a view for explaining a position of an image in a state where a filter F of the optical system 1 according to the embodiment of the present invention is removed.

The optical system 1 according to the present embodiment preferably satisfies the following conditional formula (2):

$$Lb/f<5 \qquad (2)$$

where Lb is a distance from a final surface of the back group Gb to the image plane I, and f is a focal distance of the entire optical system.

When the upper limit of the conditional formula (2) is exceeded, the distance from the back group Gb to the image formation position is increased to increase the entire length of the optical system 1.

More preferably, the optical system 1 according to the present embodiment satisfies the following conditional formula (2'):

$$Lb/f<3 \qquad (2')$$

When the above conditional formula (2') is satisfied, the distance from the back group Gb to the image formation position is further reduced to further reduce the entire length of the optical system 1.

More preferably, the optical system 1 according to the present embodiment satisfies the following conditional formula (2"):

$$Lb/f \leq 2 \qquad (2")$$

When the above conditional formula (2") is satisfied, the distance from the back group Gb to the image formation position is further reduced to further reduce the entire length of the optical system 1.

Figure 11:
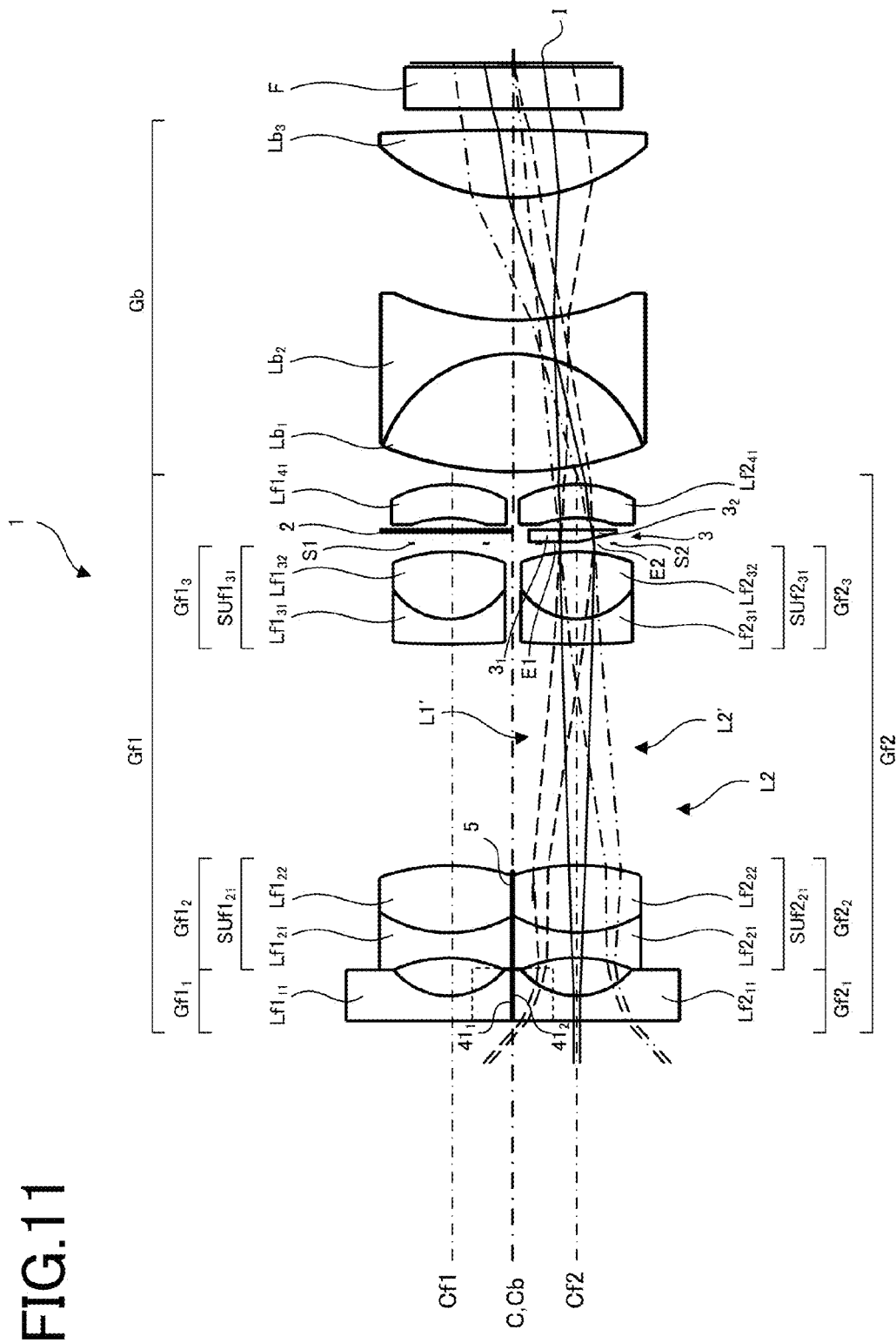
FIG. 11 is a cross-sectional view of the optical system 1 according to another embodiment taken along the central axis C thereof.
Figure 12:
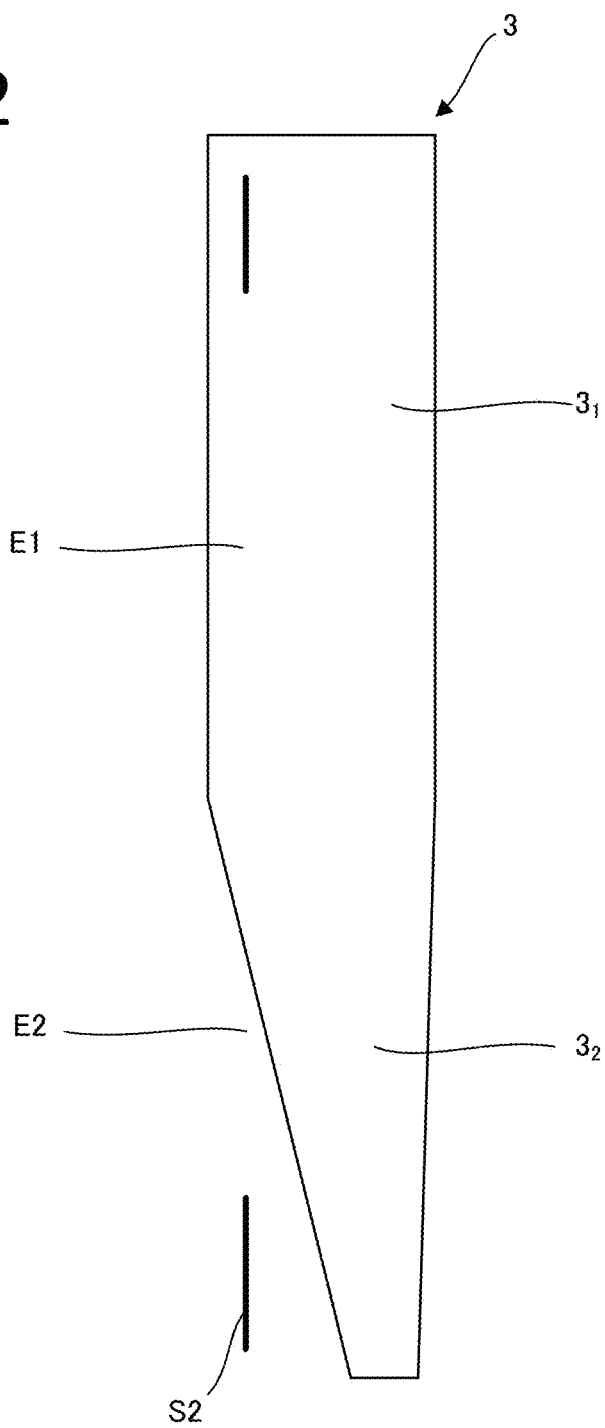
FIG. 12 is a view illustrating a pupil dividing member 3.

FIG. 11 is a cross-sectional view of the optical system 1 according to another embodiment of the present invention taken along the central axis C thereof. FIG. 12 is a view illustrating a pupil dividing member 3.

The optical system 1 according to another embodiment of the present invention preferably includes a shielding member 2 disposed in the first front group Gf1 so as to shield the first light beam L1 and a pupil dividing member 3 disposed in the second front group Gf2 so as to deflect the second light beam L2.

Ordinarily, we see stereoscopically. An object point distance upon stereoscopic observation is 30 cm from infinity, which is 0 to 3 $m^{-1}$ measured in units of diopter. However, in magnified optical system, the object point distance is 20 mm to 1 mm, which is 50 to 1000 $m^{-1}$ in diopter. Thus, stereoscopic observation fails unless the base length is changed.

The optical system 1 according to the present embodiment relates to a mechanism that changes the base length of a stereoscopic magnified optical system wherein the object point distance is largely changed. In far-point observation, stereoscopic imaging is performed in a general optical system 1 having two light paths. In near-point observation, stereoscopic imaging is performed with the first light beam L1 passing through a first light path of the two light paths shielded by the shielding member 2, and with the pupil dividing member 3 which is a pupil dividing device that divides a pupil inserted into a second light path to divide the second light beam L2 into a deflected first light beam L1' and a deflected second light beam L2'. Thus, by changing the base length according to the object point distance which may be largely changed, a natural stereoscopic effect can be obtained.

Further, in the optical system 1 according to the another embodiment, the pupil dividing member 3 preferably forms a first pupil E1 that forms an image of a part of the second light beam L2 without deflecting it and a second pupil E2 that forms an image of the remaining part of the second light beam L2 at a different position from that at which an image is formed by the first pupil E1 on the same plane thereas.

The pupil dividing member 3 that divides a pupil includes a parallel flat plate part $3_1$ corresponding to the first pupil E1 and a wedge prism part $3_2$ corresponding to the second pupil E2. The wedge prism part $3_2$ of the pupil dividing member 3 has a deflection effect to move the image formation position of the deflected second light beam L2' passing through the pupil E2 from the image formation position of the deflected first light beam L1' passing through the first pupil E1 to an adjacent position on the same plane. By disposing the pupil dividing member 3 having the above configuration to divide the pupil with the base length set short, it is possible to perform natural stereoscopic imaging for a near point by using an imaging device used for imaging a far point as it is.

Further, in the optical system 1 according to the another embodiment of the present invention, the pupil dividing member 3 has preferably a positive refractive power, and an image formation position upon far-point observation obtained without use of the pupil dividing member 3 and an image formation position upon near-point observation obtained with use of the pupil dividing member 3 are preferably the same or substantially the same.

In near-point observation, the base length needs to be set short, and at the same time, a focus position is preferably corrected. Thus, when a weak positive power is imparted to the pupil dividing member 3, focus shift upon near-point observation can be corrected.

Further, in the optical system 1 according to the another embodiment of the present invention, the shielding member 2 and pupil dividing member 3 are preferably disposed in opposition to each other between their corresponding lenses of the first front group Gf1 and second front group Gf2, respectively.

This allows the shielding member 2 and pupil dividing member 3 to be easily inserted in the optical system 1 at the same time.

Further, as illustrated in FIG. 11, the flat-concave negative lens $Lf1_{11}$ of the first front first group $Gf1_1$ may have a first cut part $41_1$ obtained by partially cutting the second front group Gf2 side thereof, and the flat-concave negative lens $Lf2_{11}$ of the second front first group $Gf2_1$ may have a second cut part $41_2$ obtained by partially cutting the first front group Gf1 side thereof.

The first cut part $41_1$ and second cut part $41_2$ are preferably brought into contact with each other. This can reduce a distance between the first optical axis of the first front group Gf1 and the second optical axis of the second front group Gf2, allowing miniaturization of the optical system 1.

The cut part may be formed in the lenses other than those of the first front first group $Gf1_1$ and second front first group $Gf2_1$. For example, the cut part may be formed, in a contact state, in other lenses of the first front group Gf1 and second front group Gf2, such as those of the first front second group $Gf1_2$ and second front second group $Gf2_2$, and those of the first front third group $Gf1_3$ and second front third group $Gf2_3$.

Further, the shielding member 5 may be installed between the first cut part $41_1$ and the second cut part $41_2$. Even when the shielding member 5 is installed to reduce the base length, it is possible to reduce a possibility that flare light generated from the first front group Gf1 and second front group Gf2 enter their counterpart groups.

More preferably, a color shift of an image generated due to deflection by the pupil dividing member 3 can be corrected electronically. More preferably, shading generated when an angle of ray incident on the imaging device is increased can be corrected electronically.

Hereinafter, Examples 1 to 10 of the optical system 1 according to the present embodiment will be described. Numerical data of Examples 1 to 10 will be given later.

Figure 13:
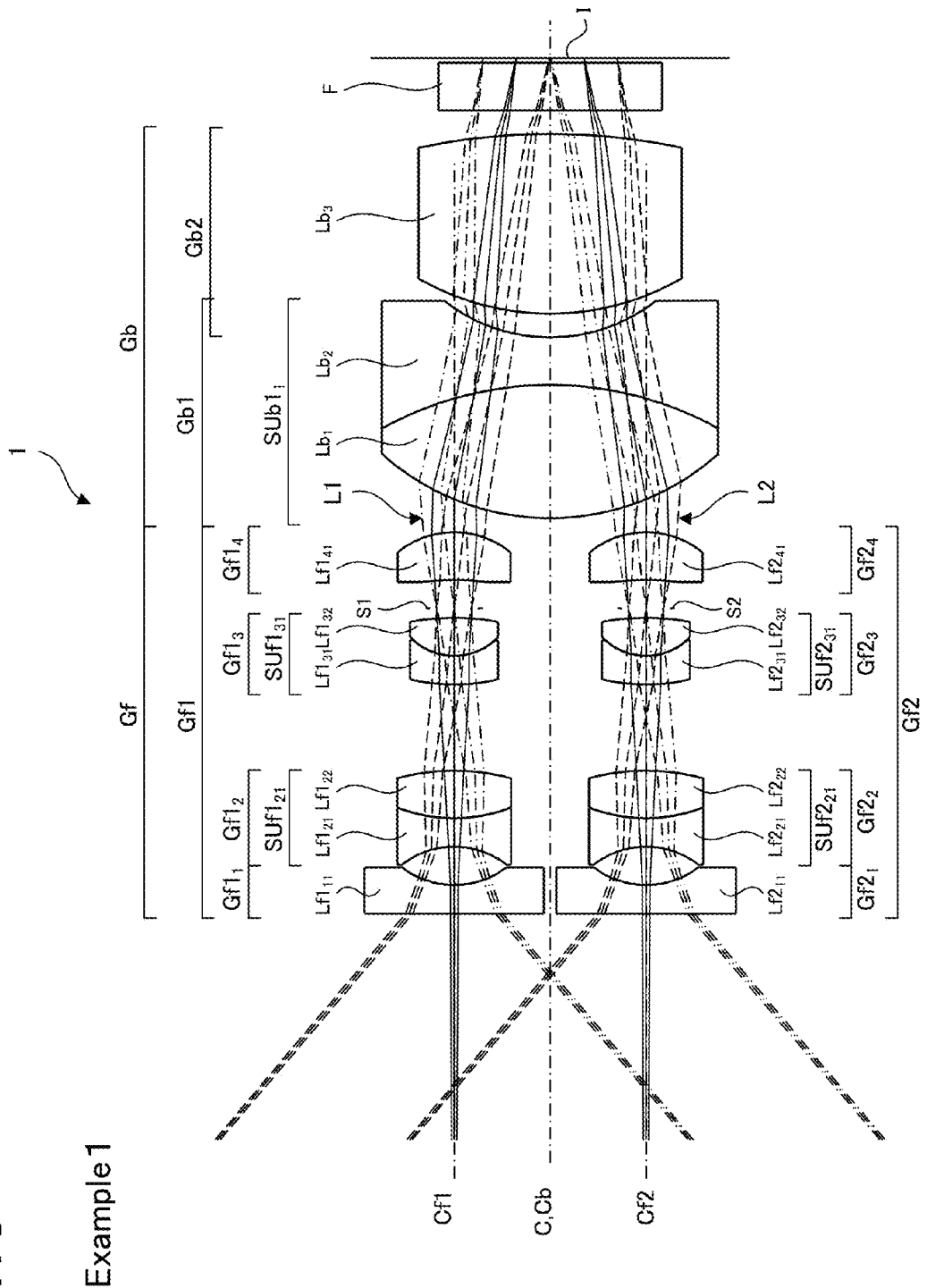
FIG. 13 is a cross-sectional view of the optical system 1 according to Example 1 taken along the central axis C thereof.
Figure 14:
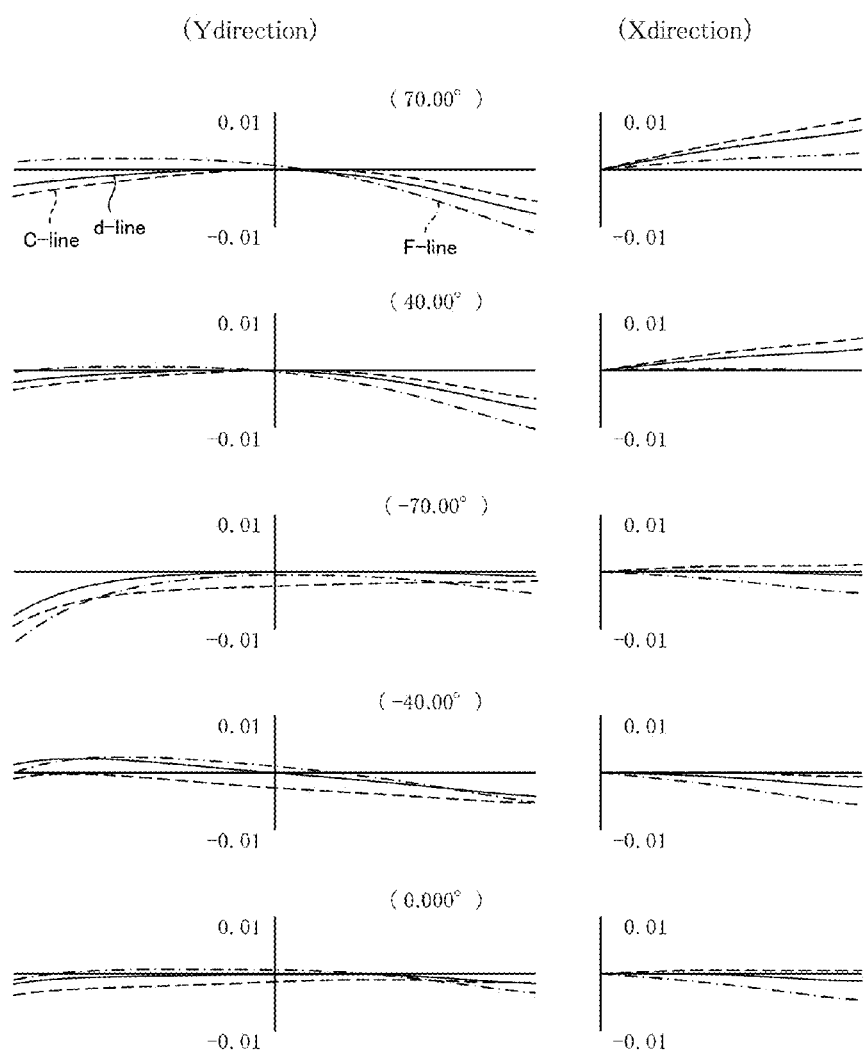
FIG. 14 is a lateral aberration diagram of the optical system 1 of Example 1.

FIG. 13 is a cross-sectional view of the optical system 1 according to Example 1 taken along the central axis C thereof. FIG. 14 is a lateral aberration diagram of the optical system 1 of Example 1.

Angles given in a center of the lateral aberration diagram each represent (view angle in the vertical direction), and lateral aberrations in the Y-direction (meridional direction) and X-direction (sagittal direction) at respective view angles are given. A negative view angle means an angle in a clockwise direction with respect to an X-axis positive direction. The same is applied to the lateral aberration diagrams of Examples 2 to 10 descried below.

As illustrated in FIG. 13, the optical system 1 of Example 1 includes, in order from the object side to the image side, a front group Gf and a back group Gb. The front group Gf includes a first front group Gf1 having a first front group central axis Cf1 and a second front group Gf2 having a second front group central axis Cf2 extending parallel to the first front group central axis Cf1. The back group Gb has a single back group central axis Cb.

Parallel arrangement of the first front group Gf1 and second front group Gf2 allows stereoscopic observation.

The first front group Gf1 preferably includes a first front first group $Gf1_1$ including a flat-concave negative lens $Lf1_{11}$ whose flat surface faces the object side, a first front second group $Gf1_2$ including a cemented lens $SUf1_{21}$ composed of a concave-concave negative lens $Lf1_{21}$ and a convex-convex positive lens $Lf1_{22}$, a first front third group $Gf1_3$ including a cemented lens $SUf1_{31}$ composed of a negative meniscus lens $Lf1_{31}$ whose convex surface faces the object side and a convex-convex positive lens $Lf1_{32}$, a first stop S1, and a first front fourth group $Gf1_4$ including a positive meniscus lens $Lf1_{41}$ whose convex surface faces the image plane side.

The second front group Gf2 preferably includes a second front first group $Gf2_1$ including a flat-concave negative lens $Lf2_{11}$ whose flat surface faces the object side, a second front second group $Gf2_2$ including a cemented lens $SUf2_{21}$ composed of a concave-concave negative lens $Lf2_{21}$ and a convex-convex positive lens $Lf2_{22}$, a second front third group $Gf2_3$ including a cemented lens $SUf2_{31}$ composed of a negative meniscus lens $Lf2_{31}$ whose convex surface faces the object side and a convex-convex positive lens $Lf2_{32}$, a second stop S2, and a second front fourth group $Gf2_4$ including a positive meniscus lens $Lf2_{41}$ whose convex surface faces the image plane side.

The back group Gb includes a back first group $Gb_1$ including a cemented lens $SUb1_1$ composed of a convex-convex positive lens $Lb_1$ and a concave-concave negative lens $Lb_2$ and a back second group Gb2 including a convex-convex positive lens $Lb_3$.

A filter is disposed in front of the image plane I.

A first light beam L1 entering the first front group Gf1 from an unillustrated first object plane passes through the flat-concave negative lens $LF1_{11}$ of the first front first group $Gf1_1$, cemented lens $SUf1_{21}$ of the first front second group $Gf1_2$, cemented lens $SUf1_{31}$ of the first front third group $Gf1_3$, first stop S1, and positive meniscus lens $Lf1_{41}$ of the first front fourth group $Gf1_4$, exits from the first front group Gf1, and, thereafter, enters the back group Gb.

A second light beam L2 entering the second front group Gf2 from an unillustrated second object plane passes through the flat-concave negative lens $Lf2_{11}$ of the second front first group $Gf2_1$, cemented lens $SUf2_{21}$ of the second front second group $Gf2_2$, cemented lens $SUf2_{31}$ of the second front third group $Gf2_3$, second stop S2, and positive meniscus lens $Lf2_{41}$ of the second front fourth group $Gf2_4$, exits from the second front group Gf2, and, thereafter, enters the back group Gb.

The first and second light beams L1 and L2 entering the back group Gb pass through the cemented lens $SUb1_1$ of the back first group Gb1, the convex-convex positive lens $Lb_3$ of the back second group Gb2, and the filter F, and then enter the image plane.

Figure 15:
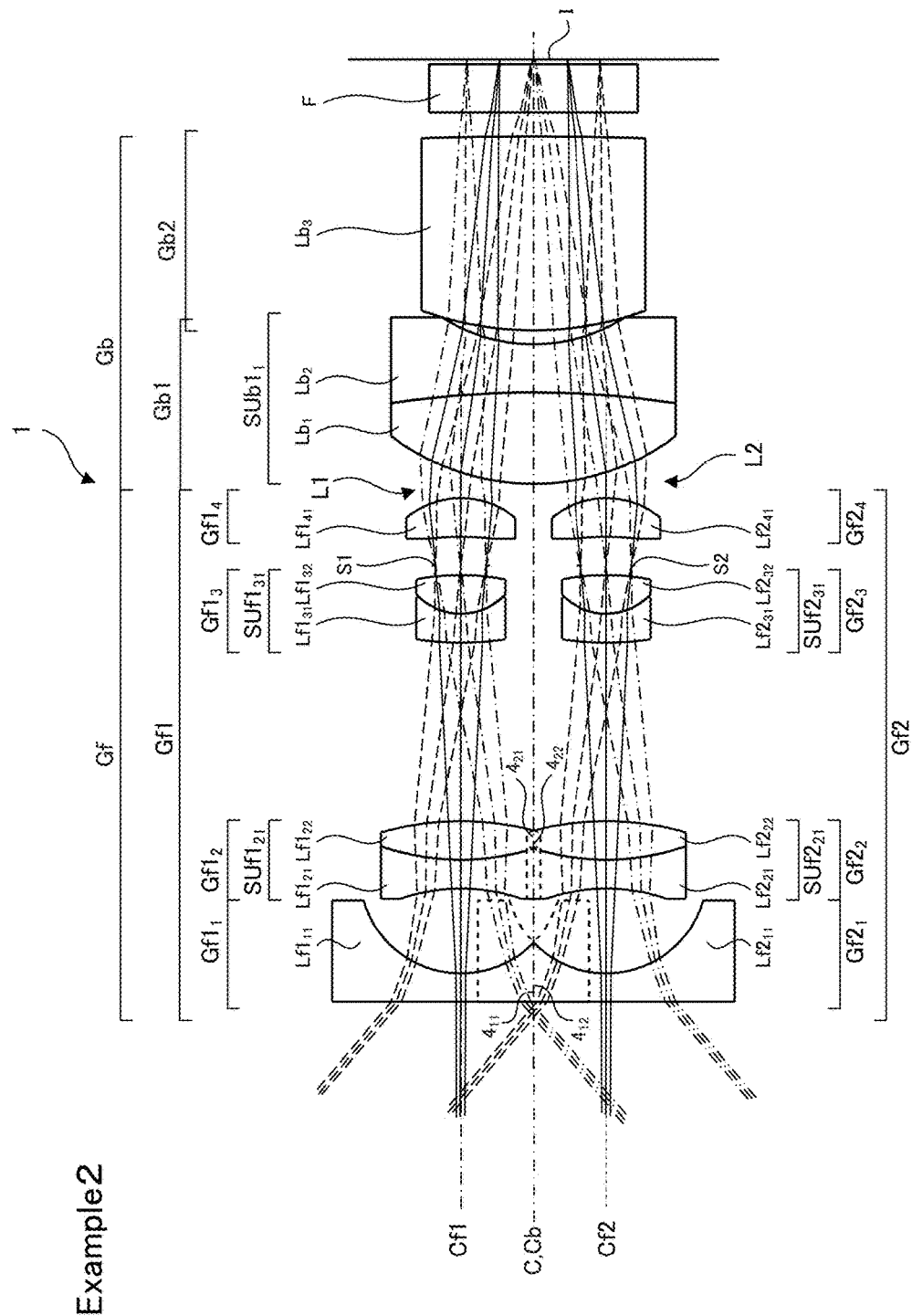
FIG. 15 is a cross-sectional view of the optical system 1 according to Example 2 taken along the central axis C thereof.
Figure 16:
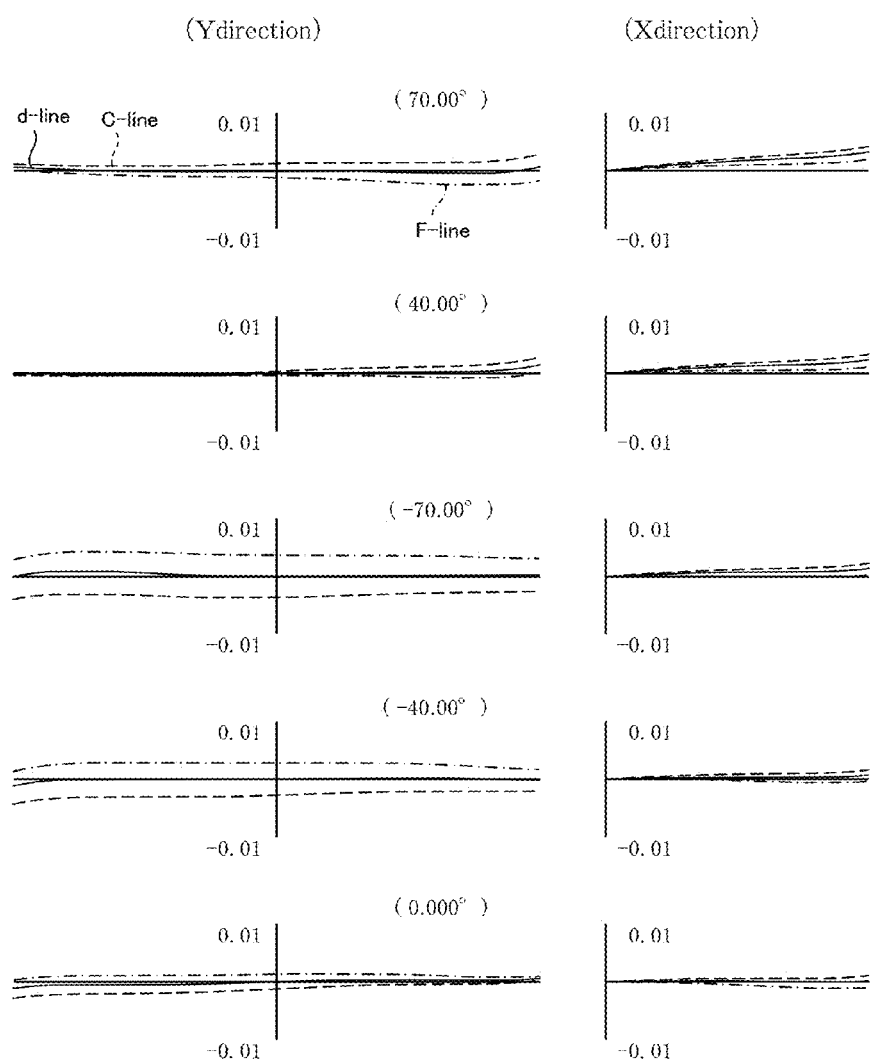
FIG. 16 is a lateral aberration diagram of the optical system 1 of Example 2.

FIG. 15 is a cross-sectional view of the optical system 1 according to Example 2 taken along the central axis C thereof. FIG. 16 is a lateral aberration diagram of the optical system 1 of Example 2.

As illustrated in FIG. 15, the optical system 1 of Example 2 includes, in order from the object side to the image side, a front group Gf and a back group Gb. The front group Gf includes a first front group Gf1 having a first front group central axis Cf1 and a second front group Gf2 having a second front group central axis Cf2 extending parallel to the first front group central axis Cf1. The back group Gb has a single back group central axis Cb.

Parallel arrangement of the first front group Gf1 and second front group Gf2 allows stereoscopic observation.

The first front group Gf1 preferably includes a first front first group $Gf1_1$ including a flat-concave negative lens $Lf1_{11}$ whose flat surface faces the object side, a first front second group $Gf1_2$ including a cemented lens $SUf1_{21}$ composed of a concave-concave negative lens $Lf1_{21}$ and a convex-convex positive lens $Lf1_{22}$, a first front third group $Gf1_3$ including a cemented lens $SUf1_{31}$ composed of a negative meniscus lens $Lf1_{31}$ whose convex surface faces the object side and a convex-convex positive lens $Lf1_{32}$, a first stop S1, and a first front fourth group $Gf1_4$ including a positive meniscus lens $Lf1_{41}$ whose convex surface faces the image plane side.

The second front group Gf2 preferably includes a second front first group $Gf2_1$ including a flat-concave negative lens $Lf2_{11}$ whose flat surface faces the object side, a second front second group $Gf2_2$ including a cemented lens $SUf2_{21}$ composed of a concave-concave negative lens $Lf2_{21}$ and a convex-convex positive lens $Lf2_{22}$, a second front third group $Gf2_3$ including a cemented lens $SUf2_{31}$ composed of a negative meniscus lens $Lf2_{31}$ whose convex surface faces the object side and a convex-convex positive lens $Lf2_{32}$, a second stop S2, and a second front fourth group $Gf2_4$ including a positive meniscus lens $Lf2_{41}$ whose convex surface faces the image plane side.

The back group Gb includes a back first group Gb1 including a cemented lens $SUb1_1$ composed of a convex-convex positive lens $Lb_1$ and a concave-concave negative lens $Lb_2$ and a back second group Gb2 including a convex-convex positive lens $Lb_3$.

A filter is disposed in front of the image plane I.

The flat-concave negative lens $Lf1_{11}$ of the first front first group $Gf1_1$ has a first front first group first cut part $4_{11}$ obtained by partially cutting the second front group Gf2 side thereof, and the flat-concave negative lens $Lf2_{11}$ of the second front first group Gf2$_1$ has a second front first group second cut part 4$_{12}$ obtained by partially cutting the first front group Gf1 side thereof.

The cemented lens SUf1$_{21}$ of the first front second group Gf1$_2$, which is composed of the concave-concave negative lens Lf1$_{21}$ and the convex-convex positive lens Lf1$_{22}$ has a first front second group first cut part 4$_{21}$ obtained by partially cutting the second front group Gf2 side thereof, and the cemented lens SUf2$_{21}$ composed of the concave-concave negative lens Lf2$_{21}$ and convex-convex positive lens Lf2$_{22}$ of the second front second group Gf2$_2$ has a second front second group second cut part 4$_{22}$ obtained by partially cutting the first front group Gf1 side thereof.

A shielding member 5 may be installed between the contacting cut parts of the respective first front group Gf1 and second front group Gf2.

A first light beam L1 entering the first front group Gf1 from an unillustrated first object plane passes through the flat-concave negative lens Lf1$_{11}$ of the first front first group Gf1$_1$, the cemented lens SUf1$_{21}$ of the first front second group Gf1$_2$, the cemented lens SUf1$_{31}$ of the first front third group Gf1$_3$, the first stop S1, and the positive meniscus lens Lf1$_{41}$ of the first front fourth group Gf1$_4$, exits from the first front group Gf1, and, thereafter, enters the back group Gb.

A second light beam L2 entering the second front group Gf2 from an unillustrated second object plane passes through the flat-concave negative lens Lf2$_{11}$ of the second front first group Gf2$_1$, the cemented lens SUf2$_{21}$ of the second front second group Gf2$_2$, the cemented lens SUf2$_{31}$ of the second front third group Gf2$_3$, the second stop S2, and the positive meniscus lens Lf2$_{41}$ of the second front fourth group Gf2$_4$, exits from the second front group Gf2, and, thereafter, enters the back group Gb.

The first and second light beams L1 and L2 entering the back group Gb pass through the cemented lens SUb1$_1$ of the back first group Gb1, the convex-convex positive lens Lb$_3$ of the back second group Gb2, and the filter F and then enter the image plane.

Figure 17:
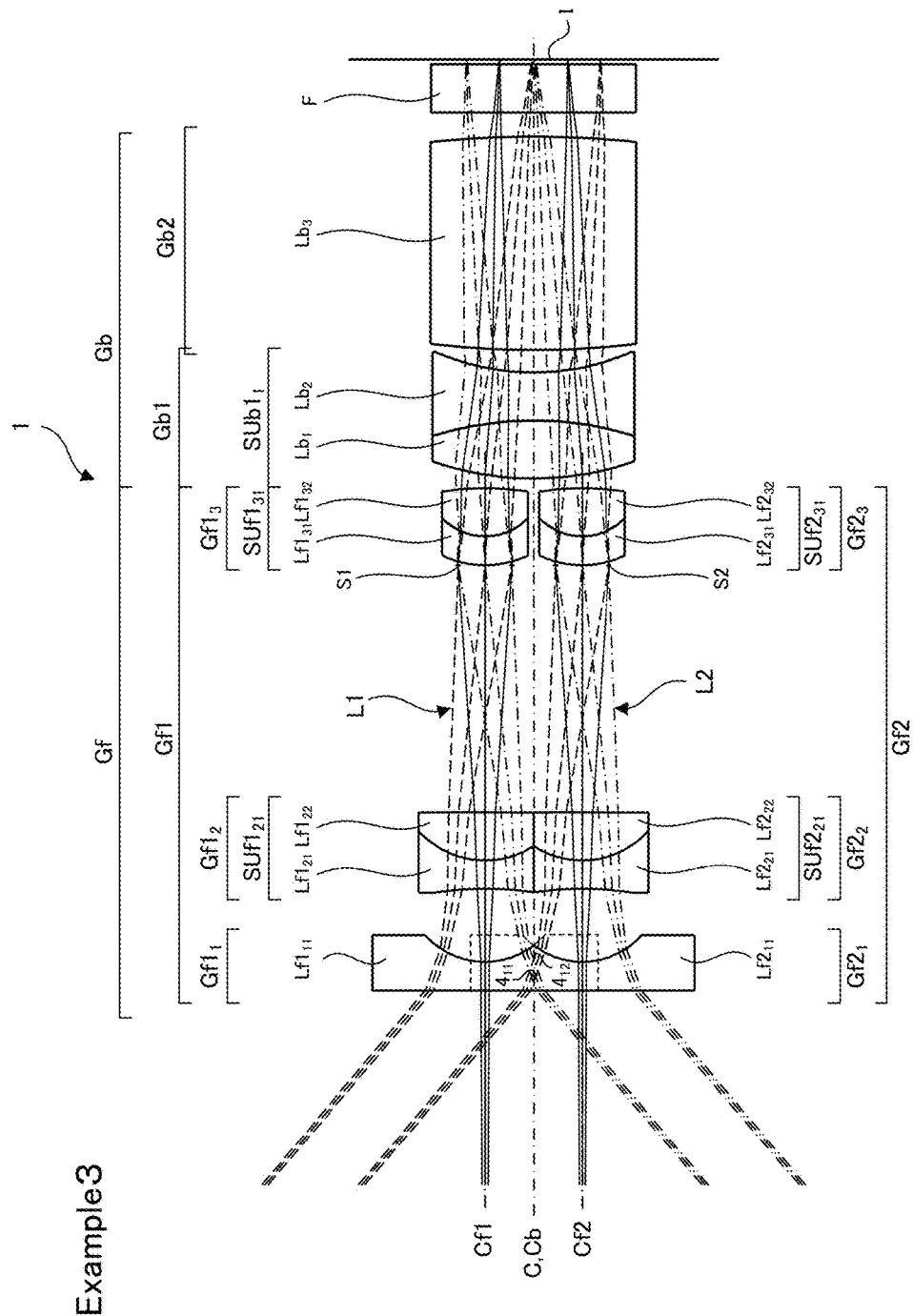
FIG. 17 is a cross-sectional view of the optical system 1 according to Example 3 taken along the central axis C thereof.
Figure 18:
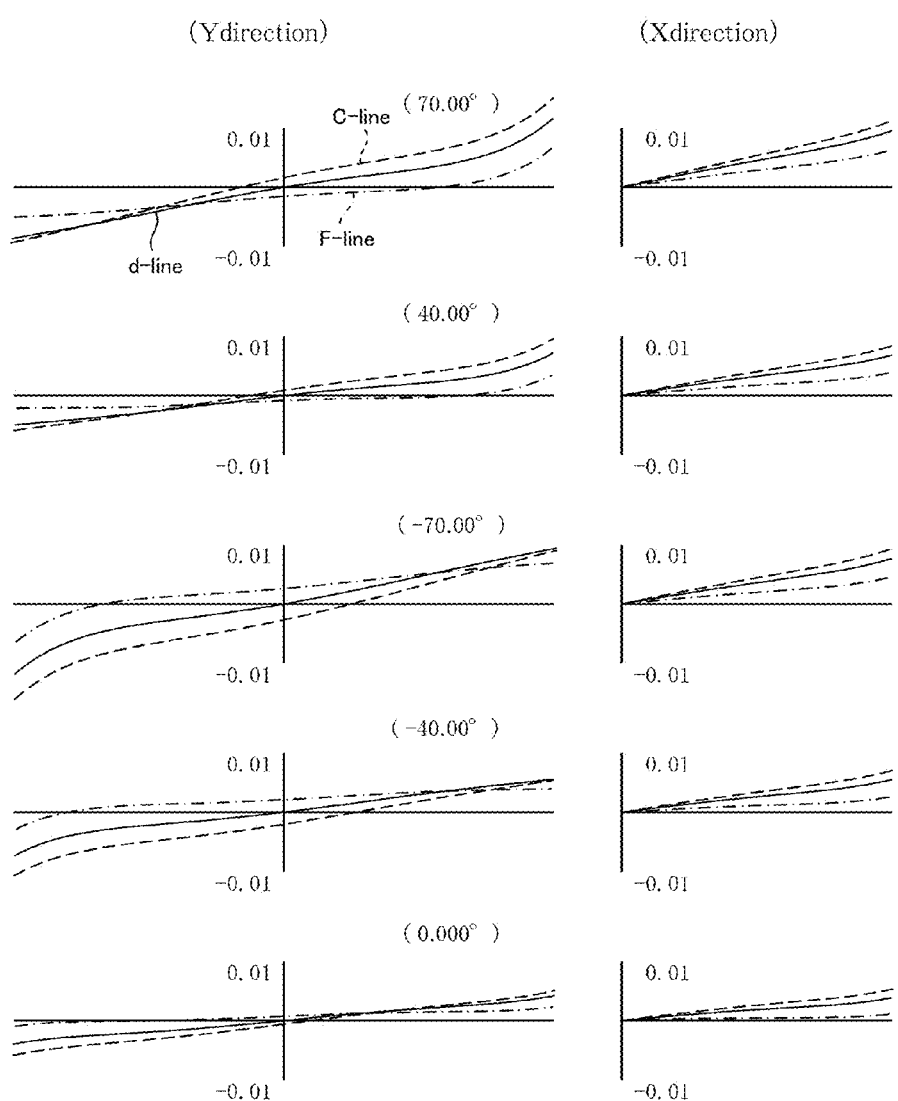
FIG. 18 is a lateral aberration diagram of the optical system 1 of Example 3.

FIG. 17 is a cross-sectional view of the optical system 1 according to Example 3 taken along the central axis C thereof. FIG. 18 is a lateral aberration diagram of the optical system 1 of Example 3.

As illustrated in FIG. 17, the optical system 1 of Example 3 includes, in order from the object side to the image side, a front group Gf and a back group Gb. The front group Gf includes a first front group Gf1 having a first front group central axis Cf1 and a second front group Gf2 having a second front group central axis Cf2 extending parallel to the first front group central axis Cf1. The back group Gb has a single back group central axis Cb.

Parallel arrangement of the first front group Gf1 and second front group Gf2 allows stereoscopic observation.

The first front group Gf1 preferably includes a first front first group Gf1$_1$ including a flat-concave negative lens Lf1$_{11}$ whose flat surface faces the object side, a first front second group Gf1$_2$ including a cemented lens SUf1$_{21}$ composed of a concave-concave negative lens Lf1$_{21}$ and a convex-convex positive lens Lf1$_{22}$, a first stop S1, and a first front third group Gf1$_3$ including a cemented lens SUf1$_{31}$ composed of a negative meniscus lens Lf1$_{31}$ whose convex surface faces the object side and a convex-convex positive lens Lf1$_{32}$.

The second front group Gf2 preferably includes a second front first group Gf2$_1$ including a flat-concave negative lens Lf2$_{11}$ whose flat surface faces the object side, a second front second group Gf2$_2$ including a cemented lens SUf2$_{21}$ composed of a concave-concave negative lens Lf2$_{21}$ and a convex-convex positive lens Lf2$_{22}$, a second stop S2, and a second front third group Gf2$_3$ including a cemented lens SUf2$_{31}$ composed of a negative meniscus lens Lf2$_{31}$ whose convex surface faces the object side and a convex-convex positive lens Lf2$_{32}$.

The back group Gb includes a back first group Gb1 including a cemented lens SUb1$_1$ composed of a convex-convex positive lens Lb$_1$ and a concave-concave negative lens Lb$_2$ and a back second group Gb2 including a convex-convex positive lens Lb$_3$.

A filter is disposed in front of the image plane I.

The flat-concave negative lens Lf1$_{11}$ of the first front first group Gf1$_1$ has a first front first group first cut part 4$_{11}$ obtained by partially cutting the second front group Gf2 side thereof, and the flat-concave negative lens Lf2$_{11}$ of the second front first group Gf2$_1$ has a second front first group second cut part 4$_{12}$ obtained by partially cutting the first front group Gf1 side thereof.

A shielding member may be installed between the contacting cut parts of the respective first front group Gf1 and second front group Gf2.

A first light beam L1 entering the first front group Gf1 from an unillustrated first object plane passes through the flat-concave negative lens Lf1$_{11}$ of the first front first group Gf1$_1$, the cemented lens SUf1$_{21}$ of the first front second group Gf1$_2$, the first stop S1, and the cemented lens SUf1$_{31}$ of the first front third group Gf1$_3$, exits from the first front group Gf1, and, thereafter, enters the back group Gb.

A second light beam L2 entering the second front group Gf2 from an unillustrated second object plane passes through the flat-concave negative lens Lf2$_{11}$ of the second front first group Gf2$_1$, the cemented lens SUf2$_{21}$ of the second front second group Gf2$_2$, the second stop S2, and the cemented lens SUf2$_{31}$ of the second front third group Gf2$_3$, exits from the second front group Gf2, and, thereafter, enters the back group Gb.

The first and second light beams L1 and L2 entering the back group Gb pass through the cemented lens SUb1$_1$ of the back first group Gb1, the convex-convex positive lens Lb$_3$ of the back second group Gb2, and the filter F and then enter the image plane.

Figure 19:
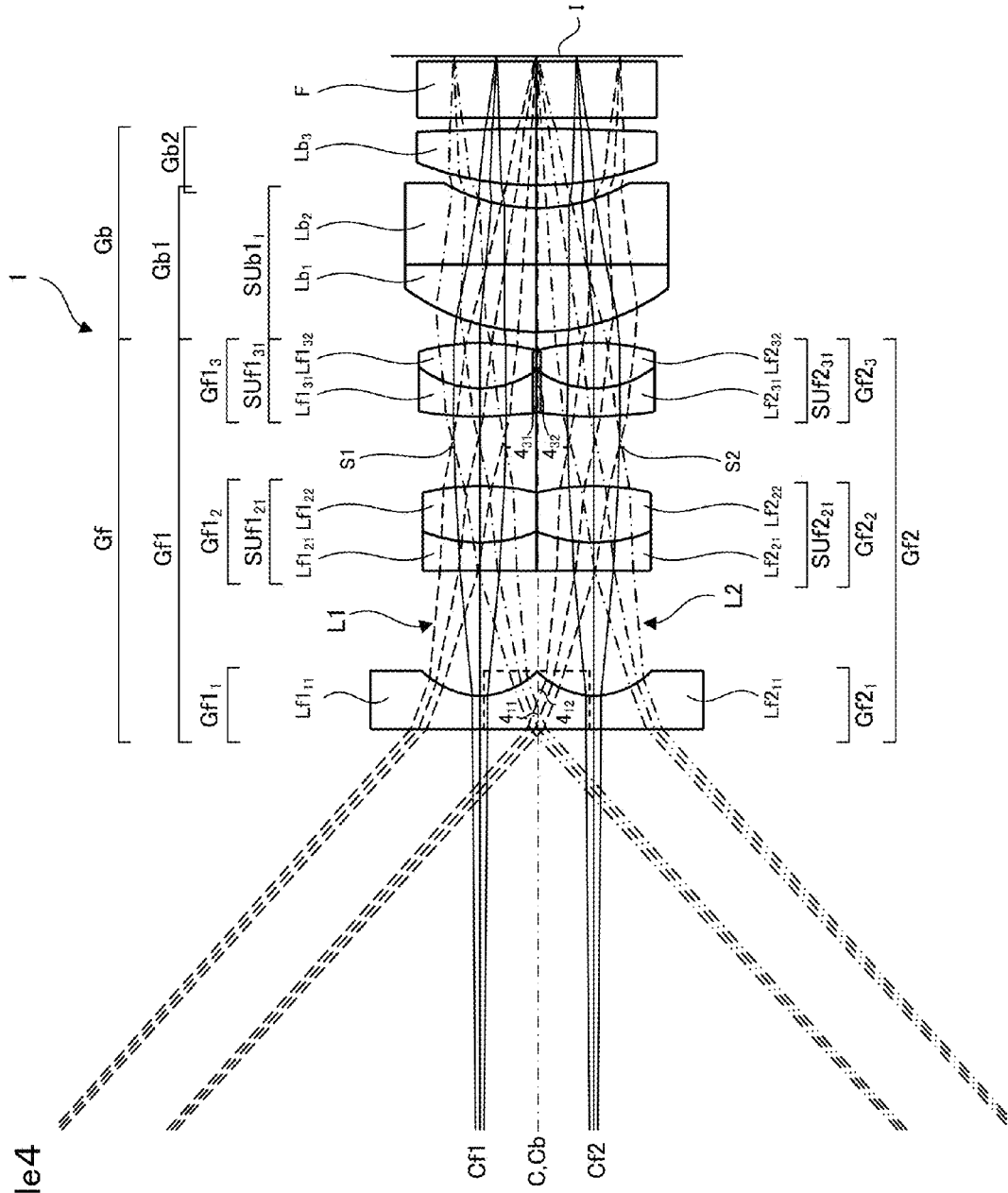
FIG. 19 is a cross-sectional view of the optical system 1 according to Example 4 taken along the central axis C thereof.
Figure 20:
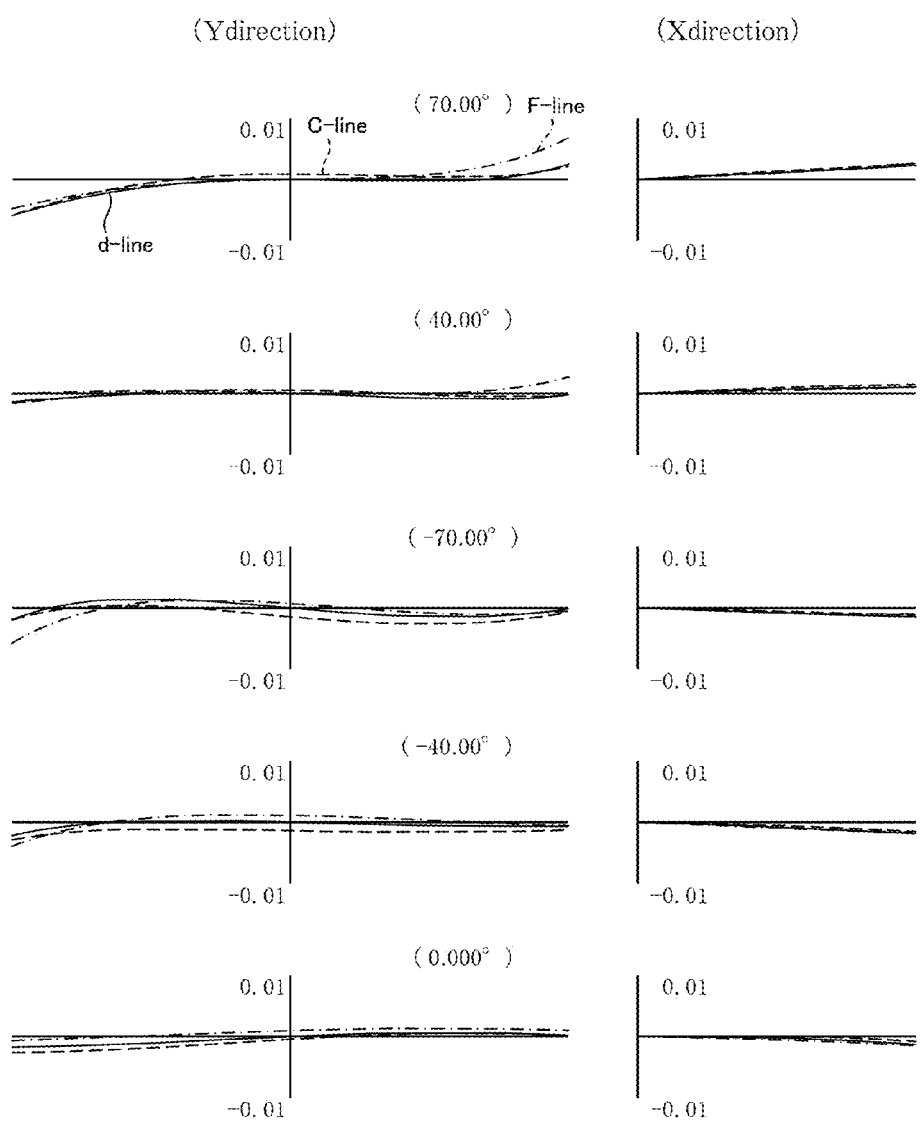
FIG. 20 is a lateral aberration diagram of the optical system 1 of Example 4.

FIG. 19 is a cross-sectional view of the optical system 1 according to Example 4 taken along the central axis C thereof. FIG. 20 is a lateral aberration diagram of the optical system 1 of Example 4.

As illustrated in FIG. 19, the optical system 1 of Example 4 includes, in order from the object side to the image side, a front group Gf and a back group Gb. The front group Gf includes a first front group Gf1 having a first front group central axis Cf1 and a second front group Gf2 having a second front group central axis Cf2 extending parallel to the first front group central axis Cf1. The back group Gb has a single back group central axis Cb.

Parallel arrangement of the first front group Gf1 and second front group Gf2 allows stereoscopic observation.

The first front group Gf1 preferably includes a first front first group Gf1$_1$ including a flat-concave negative lens Lf1$_{11}$ whose flat surface faces the object side, a first front second group Gf1$_2$ including a cemented lens SUf1$_{21}$ composed of a concave-concave negative lens Lf1$_{21}$ and a convex-convex positive lens Lf1$_{22}$, a first stop S1, and a first front third group Gf1$_3$ including a cemented lens SUf1$_{31}$ composed of a negative meniscus lens Lf1$_{31}$ whose convex surface faces the object side and a convex-convex positive lens Lf1$_{32}$.

The second front group Gf2 preferably includes a second front first group Gf2$_1$ including a flat-concave negative lens Lf2$_{11}$ whose flat surface faces the object side, a second front second group Gf2$_2$ including a cemented lens SUf2$_{21}$ composed of a concave-concave negative lens $Lf2_{21}$ and a convex-convex positive lens $Lf2_{22}$, a second stop S2, and a second front third group $Gf2_3$ including a cemented lens $SUf2_{31}$ composed of a negative meniscus lens $Lf2_{31}$ whose convex surface faces the object side and a convex-convex positive lens $Lf2_{32}$.

The back group Gb includes a back first group Gb1 including a cemented lens $SUb1_1$ composed of a convex-convex positive lens $Lb_1$ and a concave-concave negative lens $Lb_2$ and a back second group Gb2 including a convex-convex positive lens $Lb_3$.

A filter is disposed in front of the image plane I.

The flat-concave negative lens $Lf1_{11}$ of the first front first group $Gf1_1$ has a first front first group first cut part $4_{11}$ obtained by partially cutting the second front group Gf2 side thereof, and the flat-concave negative lens $Lf2_{11}$ of the second front first group $Gf2_1$ has a second front first group second cut part $4_{12}$ obtained by partially cutting the first front group Gf1 side thereof.

The cemented lens $SUf1_{31}$ of the first front third group $Gf1_3$, which is composed of the negative meniscus lens $Lf1_{31}$ whose convex surface faces the object side and the convex-convex positive lens $Lf1_{32}$ has a first front third group first cut part $4_{31}$ obtained by partially cutting the second front group Gf2 side thereof, and the cemented lens $SUf2_{31}$ of the second front third group $Gf2_3$, which is composed of the negative meniscus lens $Lf2_{31}$ whose convex surface faces the object side and the convex-convex positive lens $Lf2_{32}$ has a second front third group second cut part $4_{32}$ obtained by partially cutting the first front group Gf1 side thereof.

A shielding member 5 may be installed between the contacting cut parts of the respective first front group Gf1 and second front group Gf2.

A first light beam L1 entering the first front group Gf1 from an unillustrated first object plane passes through the flat-concave negative lens $Lf1_{11}$ of the first front first group $Gf1_1$, the cemented lens $SUf1_{21}$ of the first front second group $Gf1_2$, the first stop S1, and the cemented lens $SUf1_{31}$ of the first front third group $Gf1_3$, exits from the first front group Gf1, and, thereafter, enters the back group Gb.

A second light beam L2 entering the second front group Gf2 from an unillustrated second object plane passes through the flat-concave negative lens $Lf2_{11}$ of the second front first group $Gf2_1$, the cemented lens $SUf2_{21}$ of the second front second group $Gf2_2$, the second stop S2, and the cemented lens $SUf2_{31}$ of the second front third group $Gf2_3$, exits from the second front group Gf2, and, thereafter, enters the back group Gb.

The first and second light beams L1 and L2 entering the back group Gb pass through the cemented lens $SUb1_1$ of the back first group Gb1, convex-convex positive lens $Lb_3$ of the back second group Gb2, and filter F and then enter the image plane.

Figure 21:
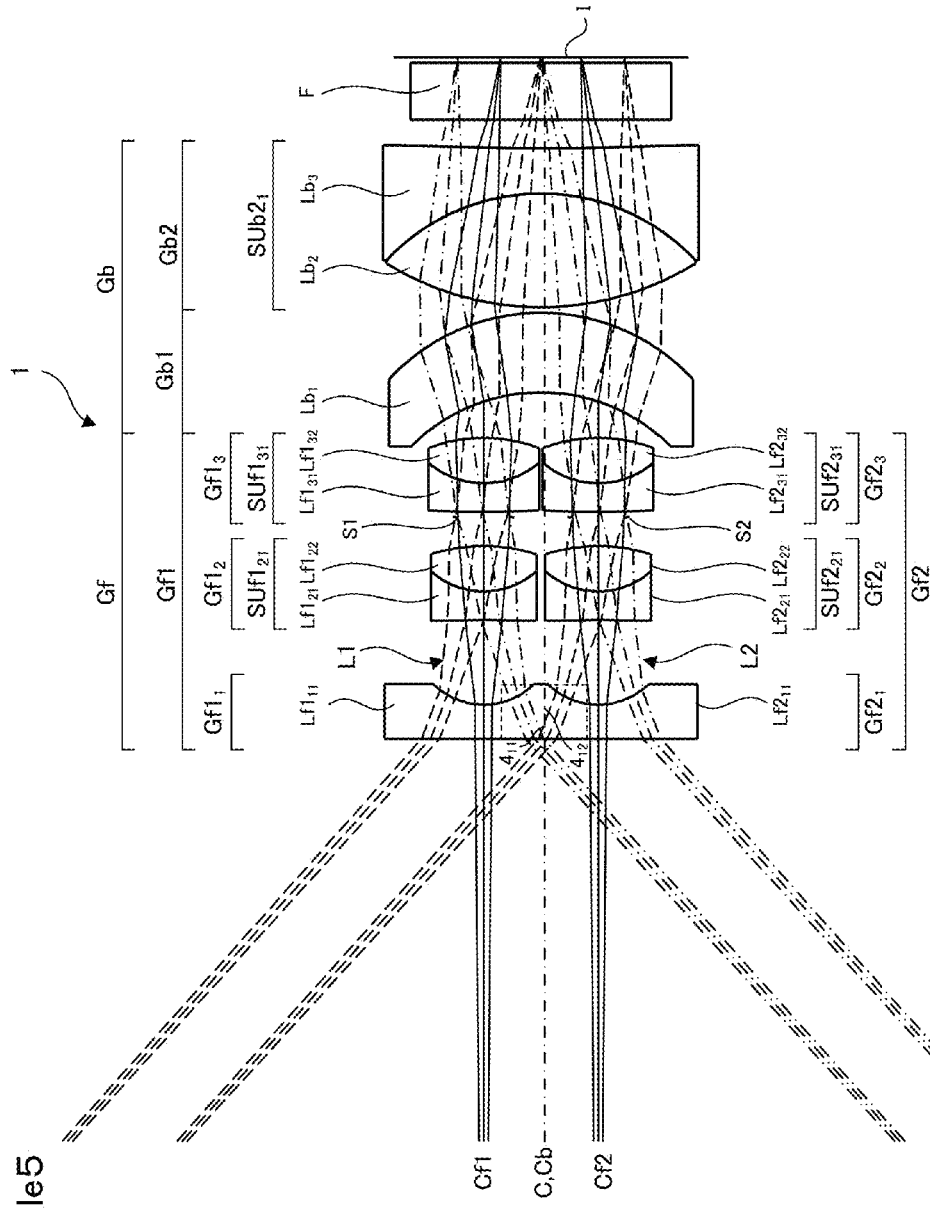
FIG. 21 is a cross-sectional view of the optical system 1 according to Example 5 taken along the central axis C thereof.
Figure 22:
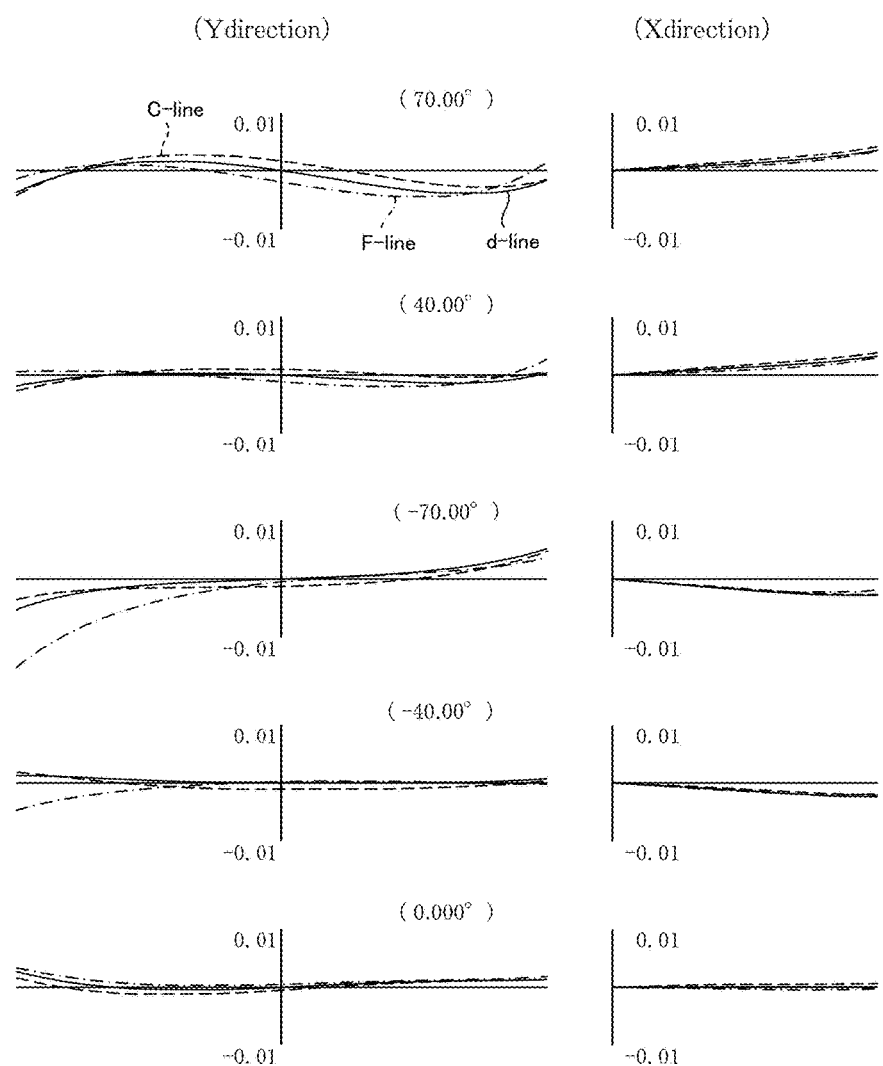
FIG. 22 is a lateral aberration diagram of the optical system 1 of Example 5.

FIG. 21 is a cross-sectional view of the optical system 1 according to Example 5 taken along the central axis C thereof. FIG. 22 is a lateral aberration diagram of the optical system 1 of Example 5.

As illustrated in FIG. 21, the optical system 1 of Example 5 includes, in order from the object side to the image side, a front group Gf and a back group Gb. The front group Gf includes a first front group Gf1 having a first front group central axis Cf1 and a second front group Gf2 having a second front group central axis Cf2 extending parallel to the first front group central axis Cf1. The back group Gb has a single back group central axis Cb.

Parallel arrangement of the first front group Gf1 and second front group Gf2 allows stereoscopic observation.

The first front group Gf1 preferably includes a first front first group $Gf1_1$ including a flat-concave negative lens $Lf1_{11}$ whose flat surface faces the object side, a first front second group $Gf1_2$ including a cemented lens $SUf1_{21}$ composed of a concave-concave negative lens $Lf1_{21}$ and a convex-convex positive lens $Lf1_{22}$, a first stop S1, and a first front third group $Gf1_3$ including a cemented lens $SUf1_{31}$ composed of a negative meniscus lens $Lf1_{31}$ whose convex surface faces the object side and a convex-convex positive lens $Lf1_{32}$.

The second front group Gf2 preferably includes a second front first group $Gf2_1$ including a flat-concave negative lens $Lf2_{11}$ whose flat surface faces the object side, a second front second group $Gf2_2$ including a cemented lens $SUf2_{21}$ composed of a concave-concave negative lens $Lf2_{21}$ and a convex-convex positive lens $Lf2_{22}$, a second stop S2, and a second front third group $Gf2_3$ including a cemented lens $SUf2_{31}$ composed of a negative meniscus lens $Lf2_{31}$ whose convex surface faces the object side and a convex-convex positive lens $Lf2_{32}$.

The back group Gb includes a back first group Gb1 including a positive meniscus lens $Lb_1$ whose convex surface faces the image plane side and a back second group Gb2 including a cemented lens $SUb2_1$ composed of a convex-convex positive lens $Lb_2$ and a concave-concave negative lens $Lb_3$.

A filter is disposed in front of the image plane I.

The flat-concave negative lens $Lf1_{11}$ of the first front first group $Gf1_1$ has a first front first group first cut part $4_{11}$ obtained by partially cutting the second front group Gf2 side thereof, and the flat-concave negative lens $Lf2_{11}$ of the second front first group $Gf2_1$ has a second front first group second cut part $4_{12}$ obtained by partially cutting the first front group Gf1 side thereof.

A shielding member may be installed between the contacting cut parts of the respective first front group Gf1 and second front group Gf2.

A first light beam L1 entering the first front group Gf1 from an unillustrated first object plane passes through the flat-concave negative lens $Lf1_{11}$ of the first front first group $Gf1_1$, the cemented lens $SUf1_{21}$ of the first front second group $Gf1_2$, the first stop S1, and the cemented lens $SUf1_{31}$ of the first front third group $Gf1_3$, exits from the first front group Gf1, and, thereafter, enters the back group Gb.

A second light beam L2 entering the second front group Gf2 from an unillustrated second object plane passes through the flat-concave negative lens $Lf2_{11}$ of the second front first group $Gf2_1$, the cemented lens $SUf2_{21}$ of the second front second group $Gf2_2$, the second stop S2, and the cemented lens $SUf2_{31}$ of the second front third group $Gf2_3$, exits from the second front group Gf2 and, thereafter, enters the back group Gb.

The first and second light beams L1 and L2 entering the back group Gb pass through the positive meniscus lens $Lb_1$ of the back first group Gb1, the cemented lens $SUb2_1$ of the back second group Gb2, and the filter F and then enter the image plane.

Figure 23:
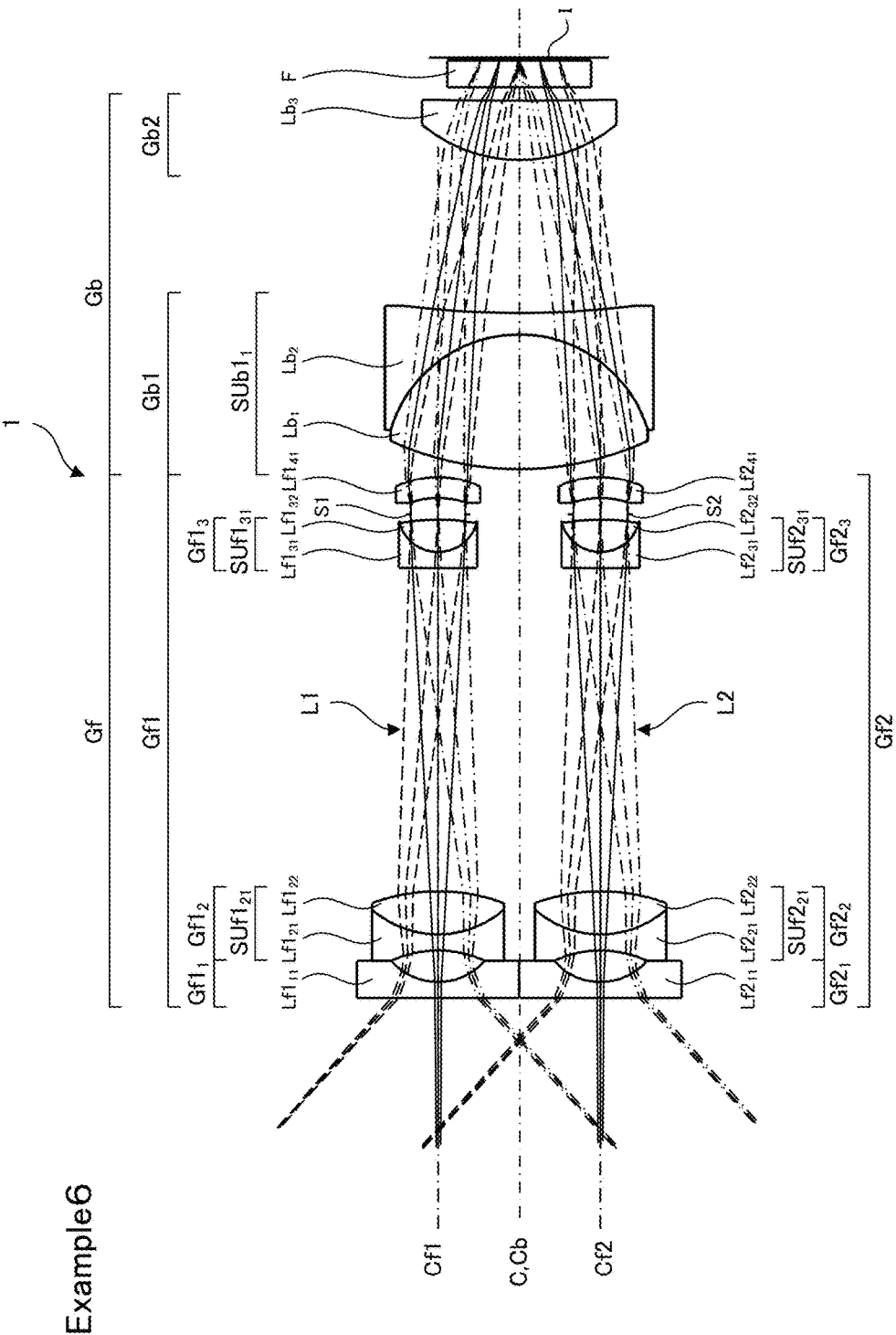
FIG. 23 is a cross-sectional view of the optical system 1 according to Example 6 taken along the central axis C thereof upon far-point observation.
Figure 24:
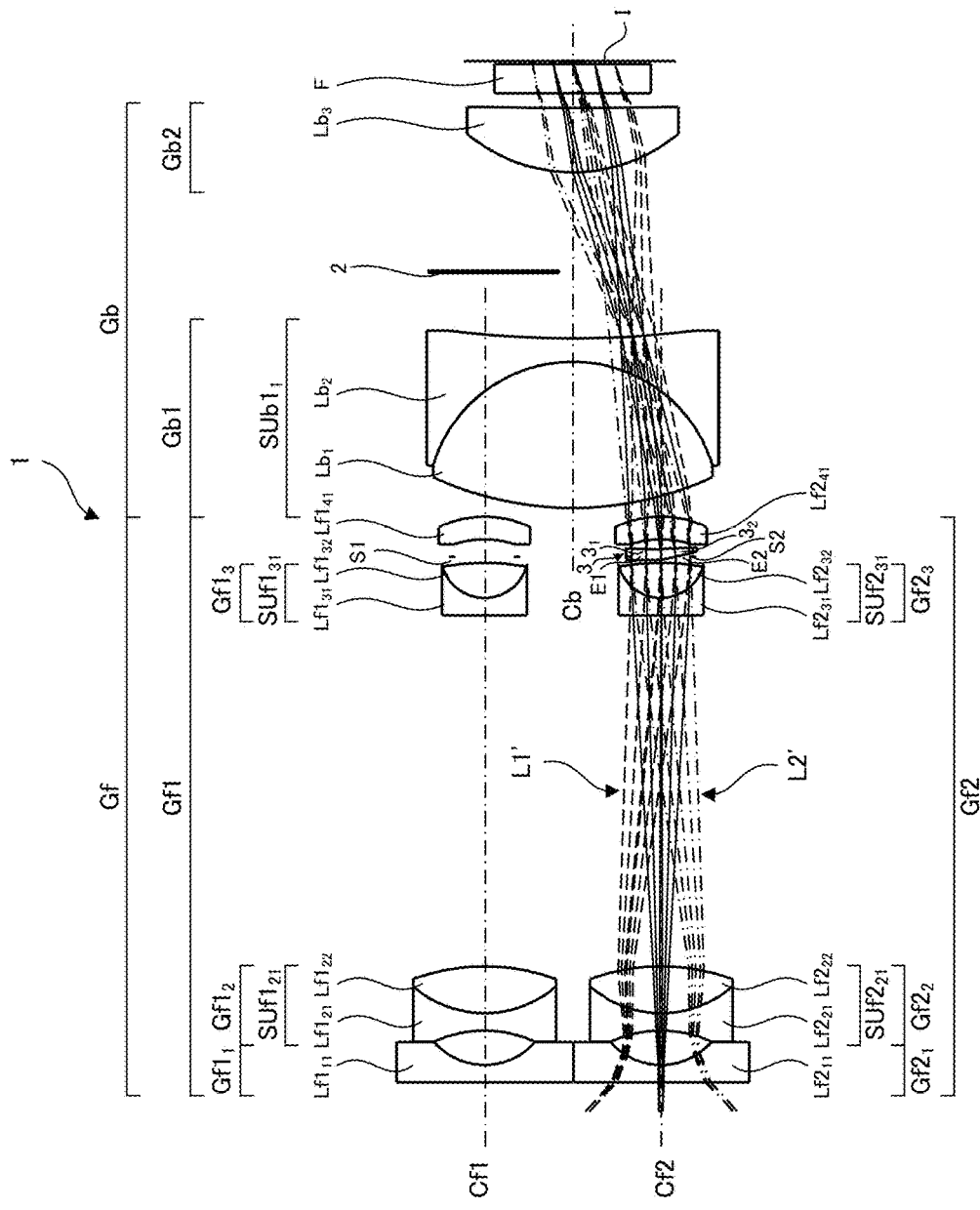
FIG. 24 is a cross-sectional view of the optical system 1 according to Example 6 taken along the central axis C thereof upon near-point observation.
Figure 25:
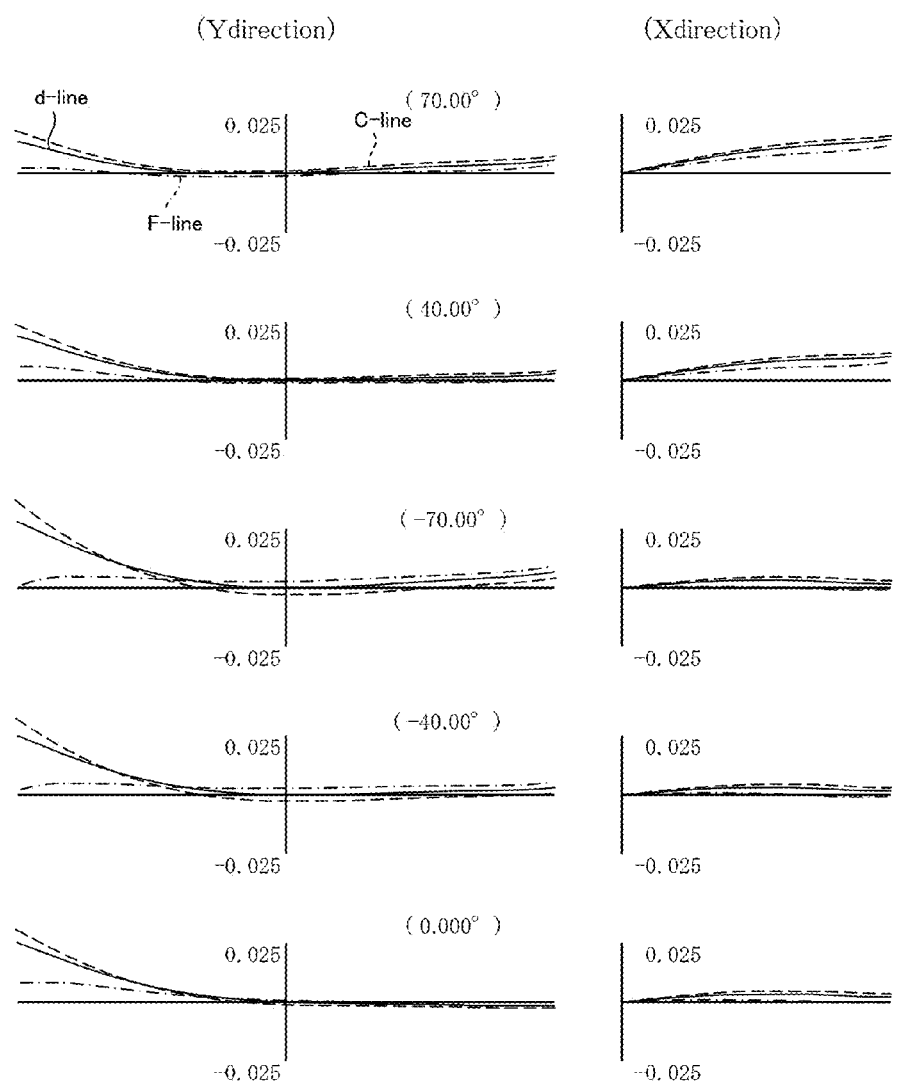
FIG. 25 is a lateral aberration diagram of the optical system 1 of Example 6 upon far-point observation.
Figure 26:
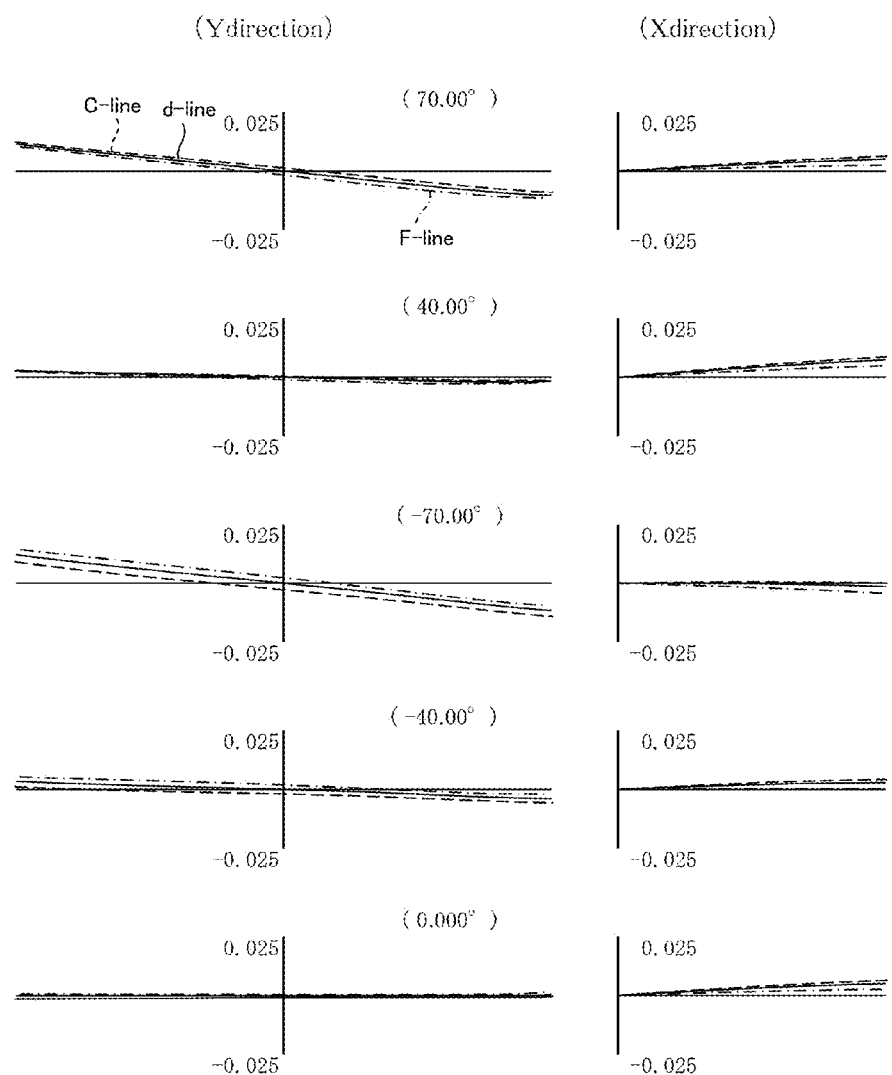
FIG. 26 is a lateral aberration diagram for a deflected first light beam L1' passing through a first pupil E1 of the optical system 1 according to Example 6 upon near-point observation.
Figure 27:
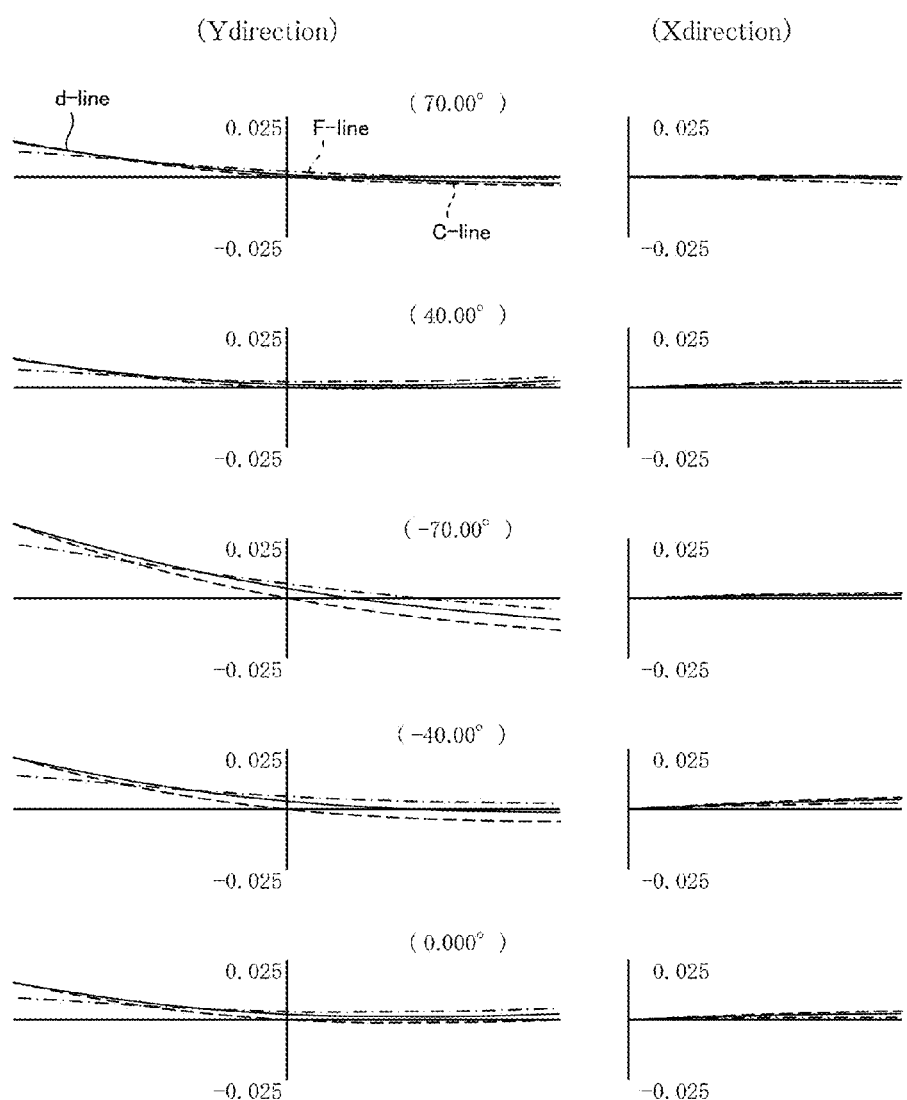
FIG. 27 is a lateral aberration diagram for a deflected second light beam L2' passing through the second pupil E2 of the optical system 1 according to Example 6 upon near-point observation.

FIG. 23 is a cross-sectional view of the optical system 1 according to Example 6 taken along the central axis C thereof upon far-point observation. FIG. 24 is a cross-sectional view of the optical system 1 according to Example 6 taken along the central axis C thereof upon near-point observation. FIG. 25 is a lateral aberration diagram of the optical system 1 of Example 6 upon far-point observation. FIG. 26 is a lateral aberration diagram for the deflected first light beam L1' passing through the first pupil E1 of the optical system 1 according to Example 6 upon near-point observation. FIG. 27 is a lateral aberration diagram for the deflected second light beam L2' passing through the second pupil E2 of the optical system 1 according to Example 6 upon near-point observation.

As illustrated in FIG. 23, the optical system 1 of Example 6 includes, in order from the object side to the image side, a front group Gf and a back group Gb. The front group Gf includes a first front group Gf1 having a first front group central axis Cf1 and a second front group Gf2 having a second front group central axis Cf2 extending parallel to the first front group central axis Cf1. The back group Gb has a single back group central axis Cb.

Parallel arrangement of the first front group Gf1 and second front group Gf2 allows stereoscopic observation.

The first front group Gf1 preferably includes a first front first group $Gf1_1$ including a flat-concave negative lens $Lf1_{11}$ whose flat surface faces the object side, a first front second group $Gf1_2$ including a cemented lens $SUf1_{21}$ composed of a concave-concave negative lens $Lf1_{21}$ and a convex-convex positive lens $Lf1_{22}$, a first front third group $Gf1_3$ including a cemented lens $SUf1_{31}$ composed of a negative meniscus lens $Lf1_{31}$ whose convex surface faces the object side and a convex-convex positive lens $Lf1_{32}$, a first stop S1, and a first front fourth group $Gf1_4$ including a negative meniscus lens $Lf1_{41}$ whose convex surface faces the image plane side.

The second front group Gf2 preferably includes a second front first group $Gf2_1$ including a flat-concave negative lens $Lf2_{11}$ whose flat surface faces the object side, a second front second group $Gf2_2$ including a cemented lens $SUf2_{21}$ composed of a concave-concave negative lens $Lf2_{21}$ and a convex-convex positive lens $Lf2_{22}$, a second front third group $Gf2_3$ including a cemented lens $SUf2_{31}$ composed of a negative meniscus lens $Lf2_{31}$ whose convex surface faces the object side and a convex-convex positive lens $Lf2_{32}$, a second stop S2, and a second front fourth group $Gf2_4$ including a negative meniscus lens $Lf2_{41}$ whose convex surface faces the image plane side.

The back group Gb includes a back first group Gb1 including a cemented lens $SUb1_1$ composed of a convex-convex positive lens $Lb_1$ and a concave-concave negative lens $Lb_2$ and a back second group Gb2 including a positive meniscus lens $Lb_3$ whose convex surface faces the object side.

A filter is disposed in front of the image plane I.

A first light beam L1 entering the first front group Gf1 from an unillustrated first object plane passes through the flat-concave negative lens $Lf1_{11}$ of the first front first group $Gf1_1$, the cemented lens $SUf1_{21}$ of the first front second group $Gf1_2$, the cemented lens $SUf1_{31}$ of the first front third group $Gf1_3$, the first stop S1, and the negative meniscus lens $Lf1_{41}$ of the first front fourth group $Gf1_4$, exits from the first front group Gf1, and, thereafter, enters the back group Gb.

A second light beam L2 entering the second front group Gf2 from an unillustrated second object plane passes through the flat-concave negative lens $Lf2_{11}$ of the second front first group $Gf2_1$, the cemented lens $SUf2_{21}$ of the second front second group $Gf2_2$, the cemented lens $SUf2_{31}$ of the second front third group $Gf2_3$, the second stop S2, and the negative meniscus lens $Lf2_{41}$ of the second front fourth group $Gf2_4$, exits from the second front group Gf2, and, thereafter, enters the back group Gb.

The first and second light beams L1 and L2 entering the back group Gb pass through the cemented lens $SUb1_1$ of the back first group Gb1, the positive meniscus lens $Lb_3$ of the back second group Gb2, and the filter F and then enter the image plane.

The optical system 1 according to Example 6 can perform near-point observation by installing therein a shielding member 2 and a pupil dividing member 3 as illustrated in FIG. 24.

The shielding member 2 shields the first light beam L1 illustrated in FIG. 23. In the example of FIG. 24, the shielding member 2 is installed between the back first and second groups Gb1 and Gb2 of the back group Gb; however, the shielding member 2 may be installed between any lenses in the first front group Gf1. Alternatively, the shielding member 2 may be installed between the front group Gf and the back group Gb.

The pupil dividing member 3 forms a first pupil E1 that forms an image of a part of the second light beam L2 illustrated in FIG. 23 without deflecting it and a second pupil E2 that forms an image of the remaining part of the second light beam L2 at a different position from that at which an image is formed by the first pupil E1 on the same plane thereas.

The pupil dividing member 3 that divides a pupil includes a parallel flat plate part $3_1$ corresponding to the first pupil E1 and a wedge prism part $3_2$ corresponding to the second pupil E2. The wedge prism part $3_2$ of the pupil dividing member 3 has a deflection effect to move the image formation position of the deflected second light beam L2' passing through the second pupil E2 from the image formation position of the deflected first light beam L1' passing through the first pupil E1 to an adjacent position on the same plane.

Figure 28:
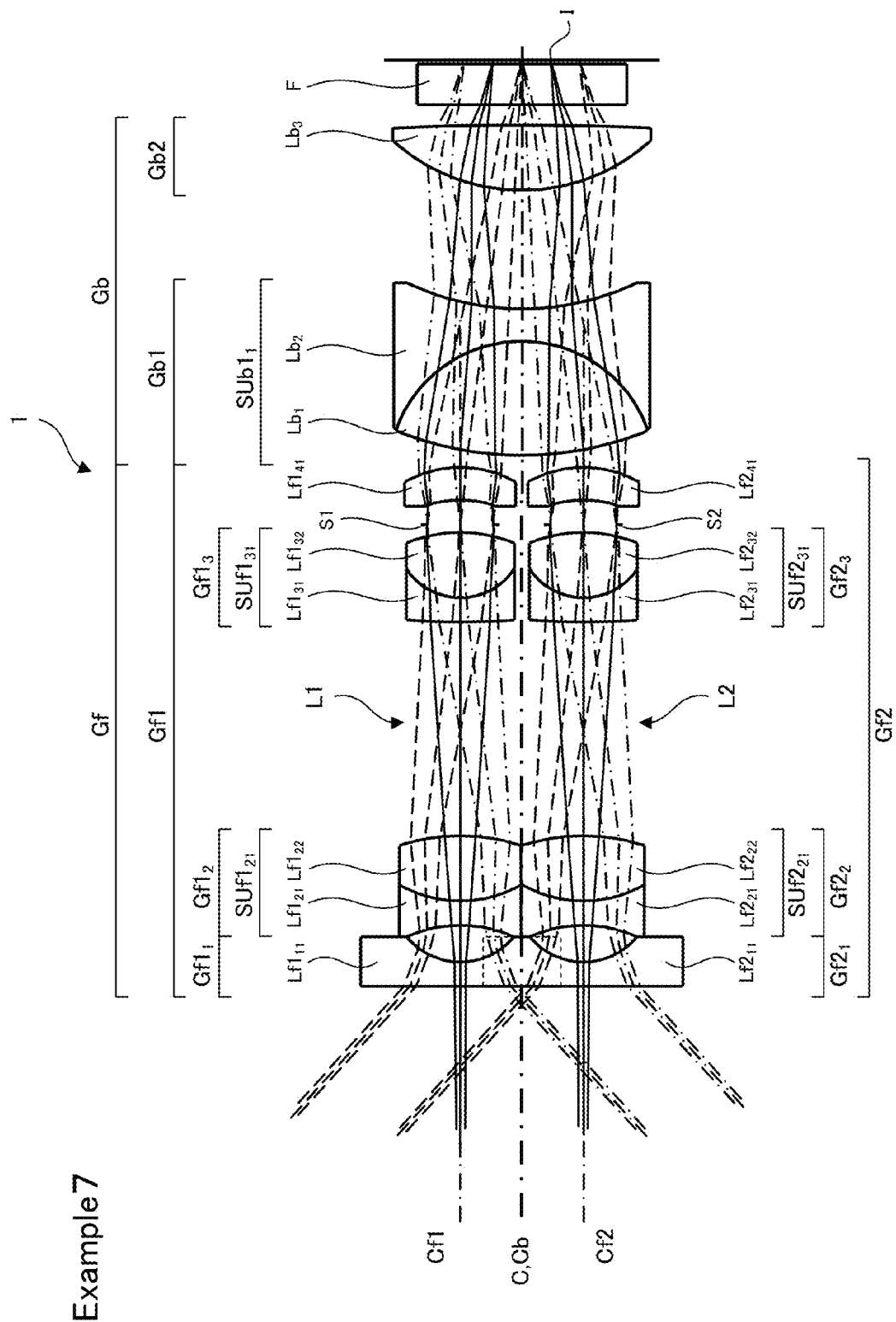
FIG. 28 is a cross-sectional view of the optical system 1 according to Example 7 taken along the central axis C thereof upon far-point observation.
Figure 29:
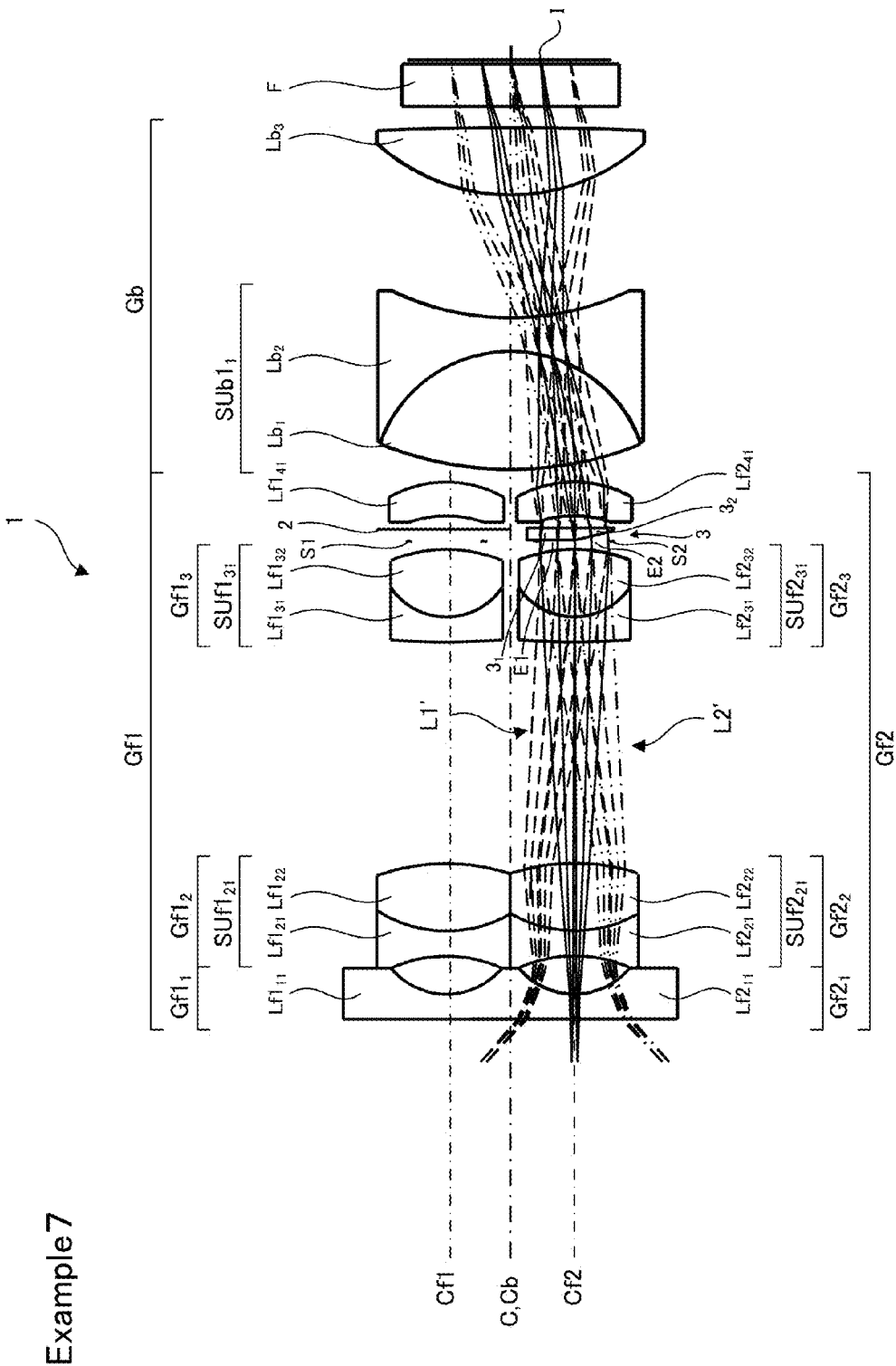
FIG. 29 is a cross-sectional view of the optical system 1 according to Example 7 taken along the central axis C thereof upon near-point observation.
Figure 30:
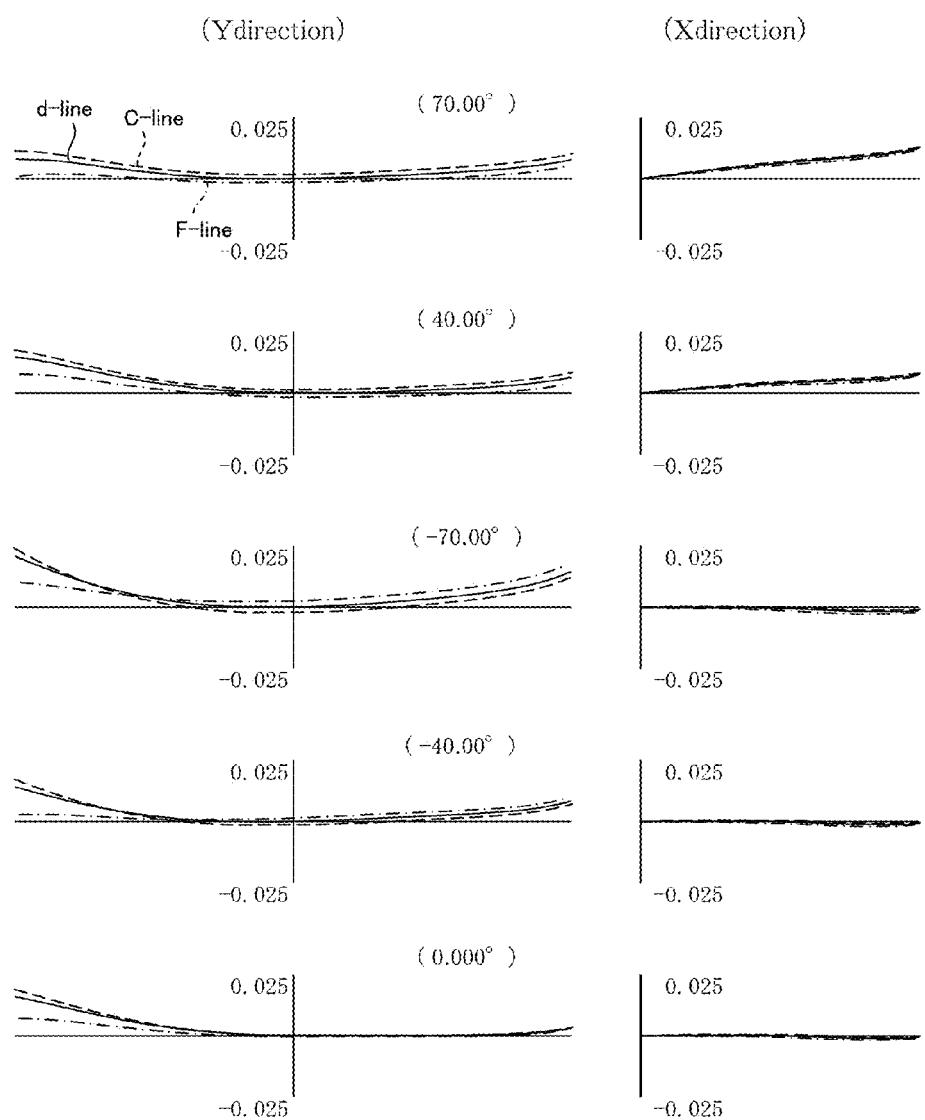
FIG. 30 is a lateral aberration diagram of the optical system 1 of Example 7 upon far-point observation.
Figure 31:
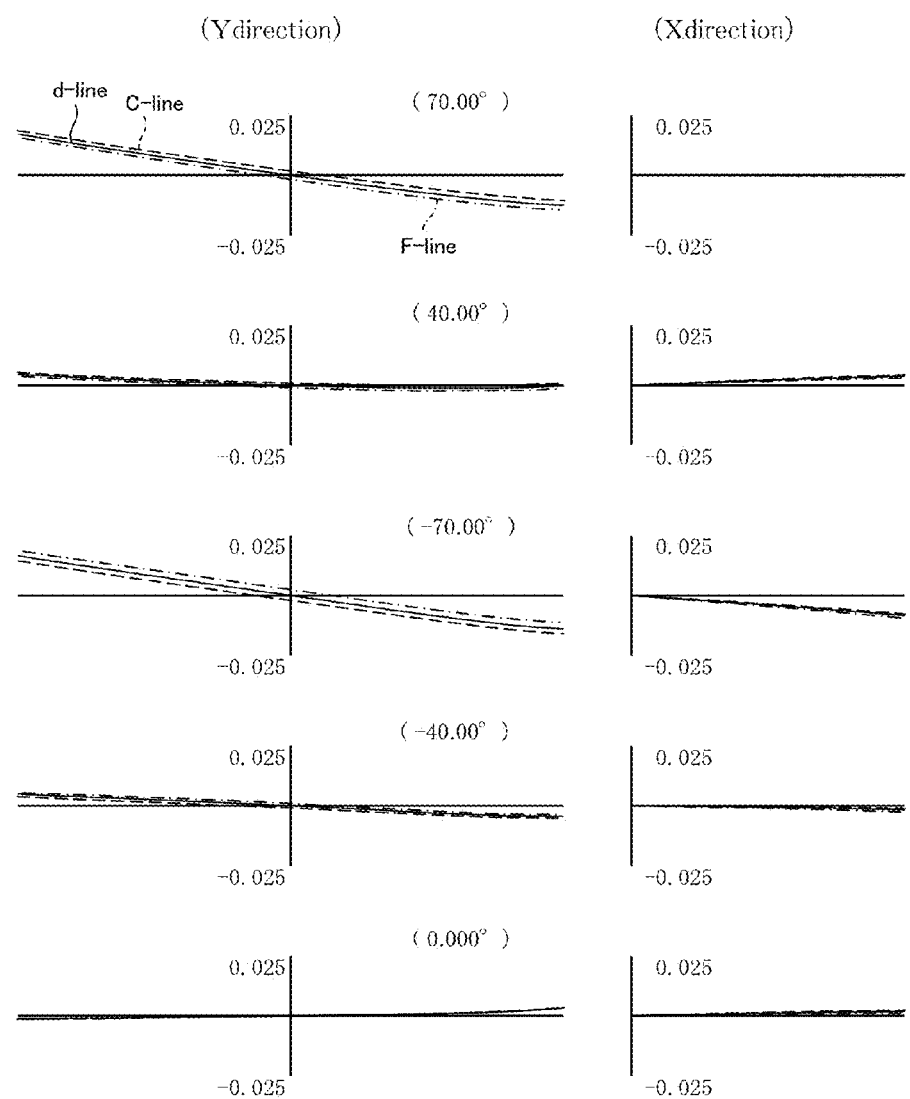
FIG. 31 is a lateral aberration diagram for the deflected first light beam L1' passing through the first pupil E1 of the optical system 1 according to Example 7 upon near-point observation.
Figure 32:
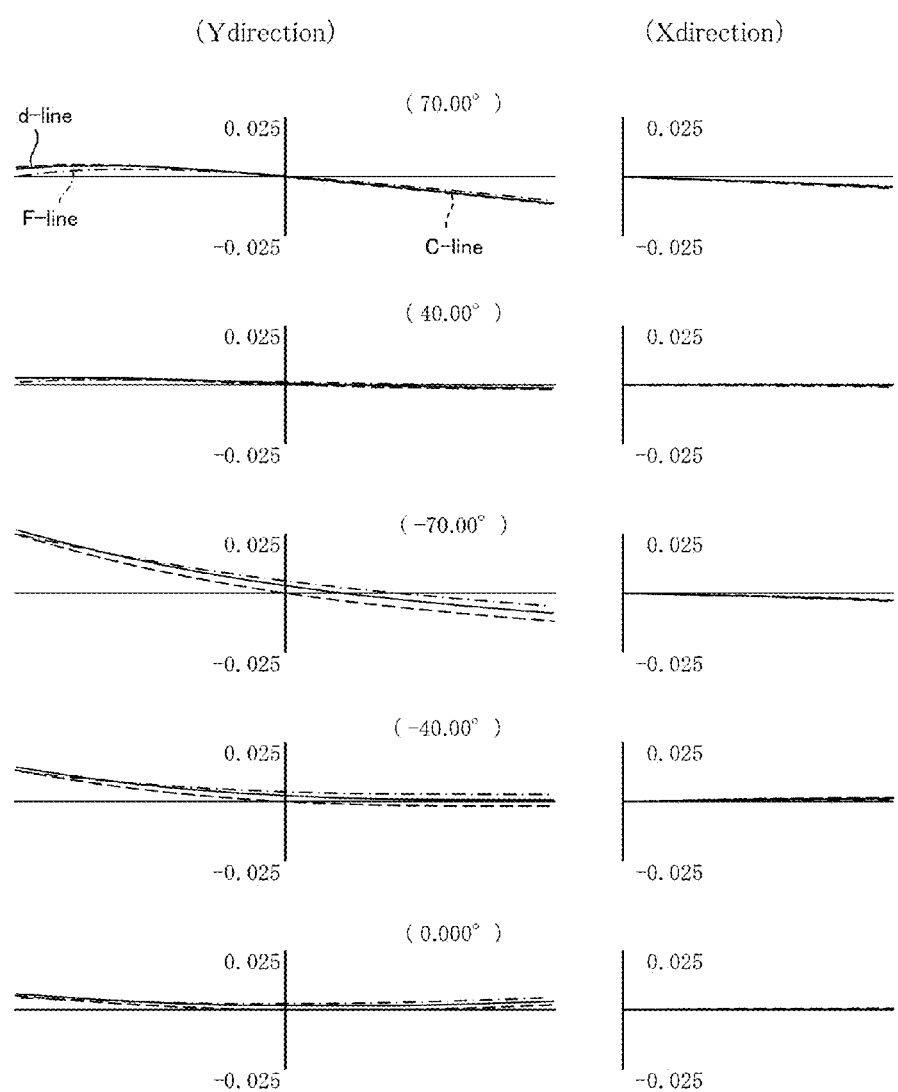
FIG. 32 is a lateral aberration diagram for the deflected second light beam L2' passing through the second pupil E2 of the optical system 1 according to Example 7 upon near-point observation.

FIG. 28 is a cross-sectional view of the optical system 1 according to Example 7 taken along the central axis C thereof upon far-point observation. FIG. 29 is a cross-sectional view of the optical system 1 according to Example 7 taken along the central axis C thereof upon near-point observation. FIG. 30 is a lateral aberration diagram of the optical system 1 of Example 7 upon far-point observation. FIG. 31 is a lateral aberration diagram for the deflected first light beam L1' passing through the first pupil E1 of the optical system 1 according to Example 7 upon near-point observation. FIG. 32 is a lateral aberration diagram for the deflected second light beam L2' passing through the second pupil E2 of the optical system 1 according to Example 7 upon near-point observation.

As illustrated in FIG. 28, the optical system 1 of Example 7 includes, in order from the object side to the image side, a front group Gf and a back group Gb. The front group Gf includes a first front group Gf1 having a first front group central axis Cf1 and a second front group Gf2 having a second front group central axis Cf2 extending parallel to the first front group central axis Cf1. The back group Gb has a single back group central axis Cb.

Parallel arrangement of the first front group Gf1 and second front group Gf2 allows stereoscopic observation.

The first front group Gf1 preferably includes a first front first group $Gf1_1$ including a flat-concave negative lens $Lf1_{11}$ whose flat surface faces the object side, a first front second group $Gf1_2$ including a cemented lens $SUf1_{21}$ composed of a concave-concave negative lens $Lf1_{21}$ and a convex-convex positive lens $Lf1_{22}$, a first front third group $Gf1_3$ including a cemented lens $SUf1_{31}$ composed of a negative meniscus lens $Lf1_{31}$ whose convex surface faces the object side and a convex-convex positive lens $Lf1_{32}$, a first stop S1, and a first front fourth group $Gf1_4$ including a negative meniscus lens $Lf1_{41}$ whose convex surface faces the image plane side.

The second front group Gf2 preferably includes a second front first group $Gf2_1$ including a flat-concave negative lens $Lf2_{11}$ whose flat surface faces the object side, a second front second group $Gf2_2$ including a cemented lens $SUf2_{21}$ composed of a concave-concave negative lens $Lf2_{21}$ and a convex-convex positive lens $Lf2_{22}$, a second front third group $Gf2_3$ including a cemented lens $SUf2_{31}$ composed of a negative meniscus lens $Lf2_{31}$ whose convex surface faces the object side and a convex-convex positive lens $Lf2_{32}$, a second stop S2, and a second front fourth group $Gf2_4$ including a negative meniscus lens $Lf2_{41}$ whose convex surface faces the image plane side.

The back group Gb includes a back first group Gb1 including a cemented lens $SUb1_1$ composed of a convex-convex positive lens $Lb_1$ and a concave-concave negative lens $Lb_2$ and a back second group Gb2 including a convex-convex positive lens $Lb_3$.

A filter is disposed in front of the image plane I.

A first light beam L1 entering the first front group Gf1 from an unillustrated first object plane passes through the flat-concave negative lens $Lf1_{11}$ of the first front first group $Gf1_1$, the cemented lens $SUf1_{21}$ of the first front second group $Gf1_2$, the cemented lens $SUf1_{31}$ of the first front third group $Gf1_3$, the first stop S1, and the negative meniscus lens $Lf1_{41}$ of the first front fourth group $Gf1_4$, exits from the first front group Gf1, and, thereafter, enters the back group Gb.

A second light beam L2 entering the second front group Gf2 from an unillustrated second object plane passes through the flat-concave negative lens $Lf2_{11}$ of the second front first group $Gf2_1$, the cemented lens $SUf2_{21}$ of the second front second group $Gf2_2$, the cemented lens $SUf2_{31}$ of the second front third group $Gf2_3$, the second stop S2, and the negative meniscus lens $Lf2_{41}$ of the second front fourth group $Gf2_4$, exits from the second front group Gf2, and, thereafter, enters the back group Gb.

The first and second light beams L1 and L2 entering the back group Gb pass through the cemented lens $SUb1_1$ of the back first group Gb1, the convex-convex positive lens $Lb_3$ of the back second group Gb2, and filter F and then enter the image plane.

The optical system 1 according to Example 7 can perform near-point observation by installing therein a shielding member 2 and a pupil dividing member 3 as illustrated in FIG. 29.

The shielding member 2 shields the first light beam L1 illustrated in FIG. 28. In the example of FIG. 29, the shielding member 2 is installed near the first stop S1 between the first front third group $Gf1_3$ and the first front fourth group $Gf1_4$.

The pupil dividing member 3 forms a first pupil E1 that forms an image of a part of the second light beam L2 illustrated in FIG. 28 without deflecting it and a second pupil E2 that forms an image of the remaining part of the second light beam L2 at a different position from that at which an image is formed by the first pupil E1 on the same plane thereas.

The pupil dividing member 3 that divides a pupil includes a parallel flat plate part $3_1$ corresponding to the first pupil E1 and a wedge prism part $3_2$ corresponding to the second pupil E2. The wedge prism part $3_2$ of the pupil dividing member 3 has a deflection effect to move the image formation position of the deflected second light beam L2' passing through the second pupil E2 from the image formation position of the deflected first light beam L1' passing through the first pupil E1 to an adjacent position on the same plane.

In the optical system 1 according to Example 7, the shielding member 2 is installed near the first stop S1 between the first front third group $Gf1_3$ and the first front fourth group $Gf1_4$, and the pupil dividing member 3 is installed near the second stop S2 between the second front third group $Gf2_3$ and the second front fourth group $Gf2_4$.

That is, the shielding member 2 and pupil dividing member 3 are disposed in opposition to each other between their corresponding lenses of the first front group Gf1 and second front group Gf2, respectively.

Figure 33:
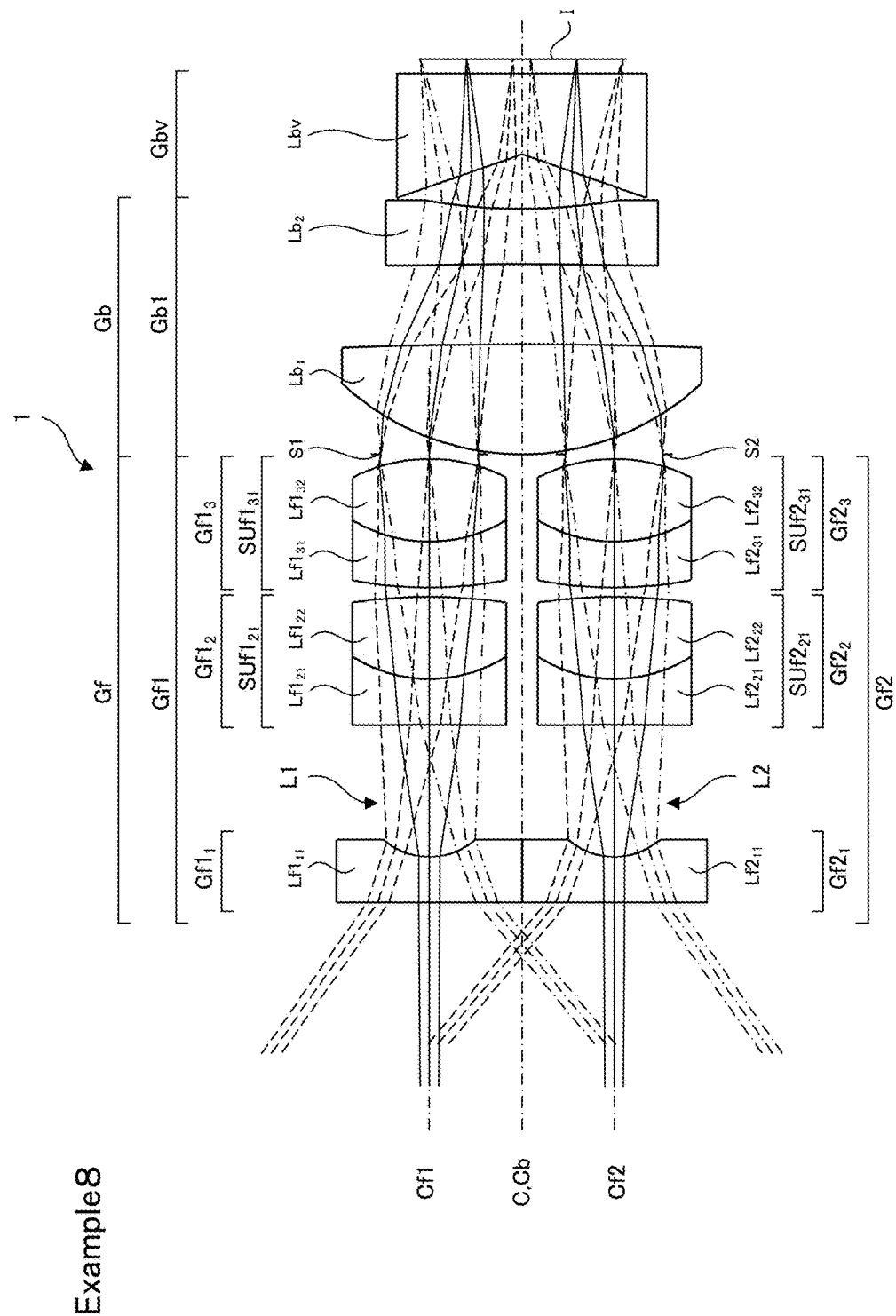
FIG. 33 is a cross-sectional view including a first front group central axis Cf1 and a second front group central axis Cf2 of the optical system 1 according to Example 8.
Figure 34:
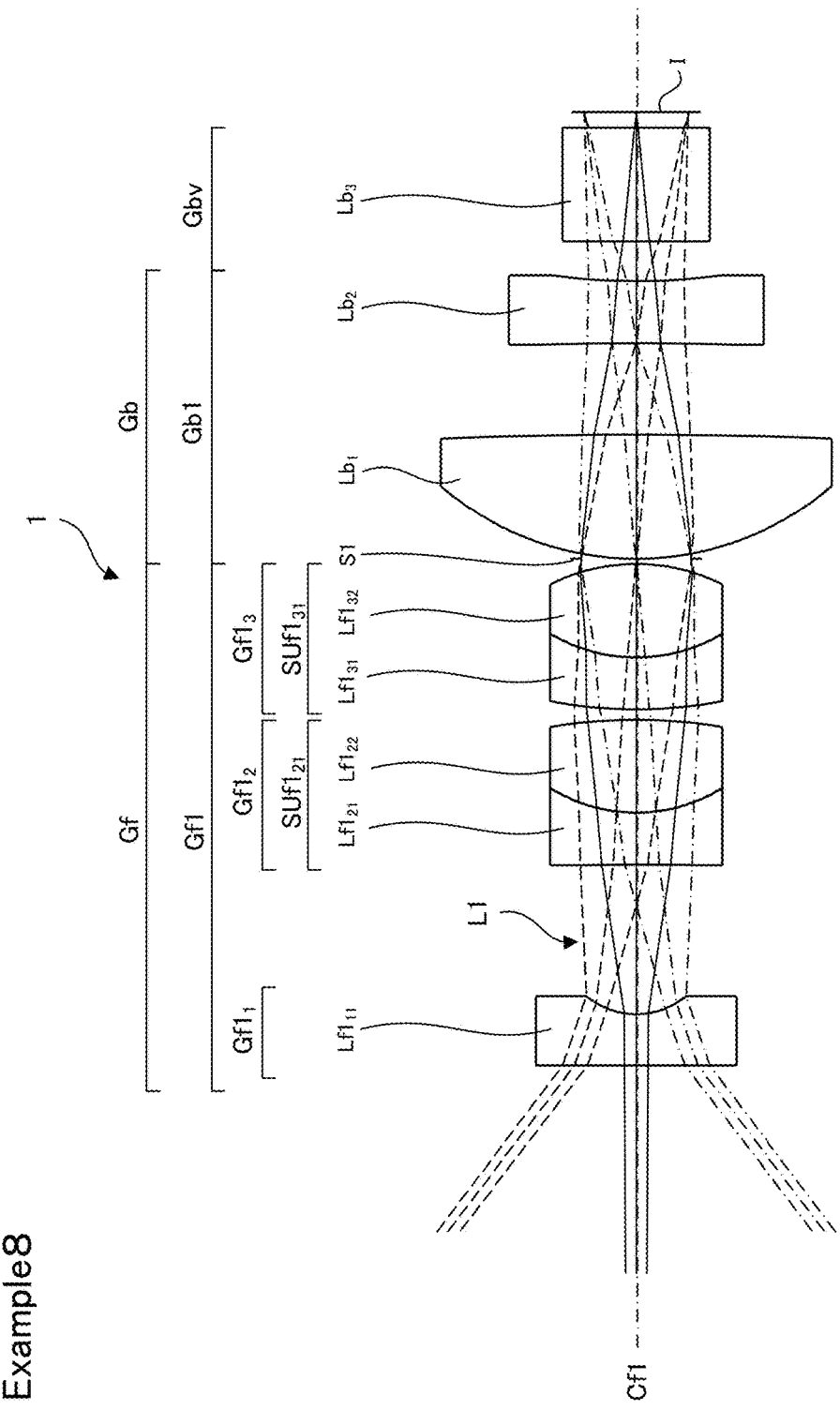
FIG. 34 is a view as seen from a direction perpendicular to that of FIG. 33.
Figure 35:
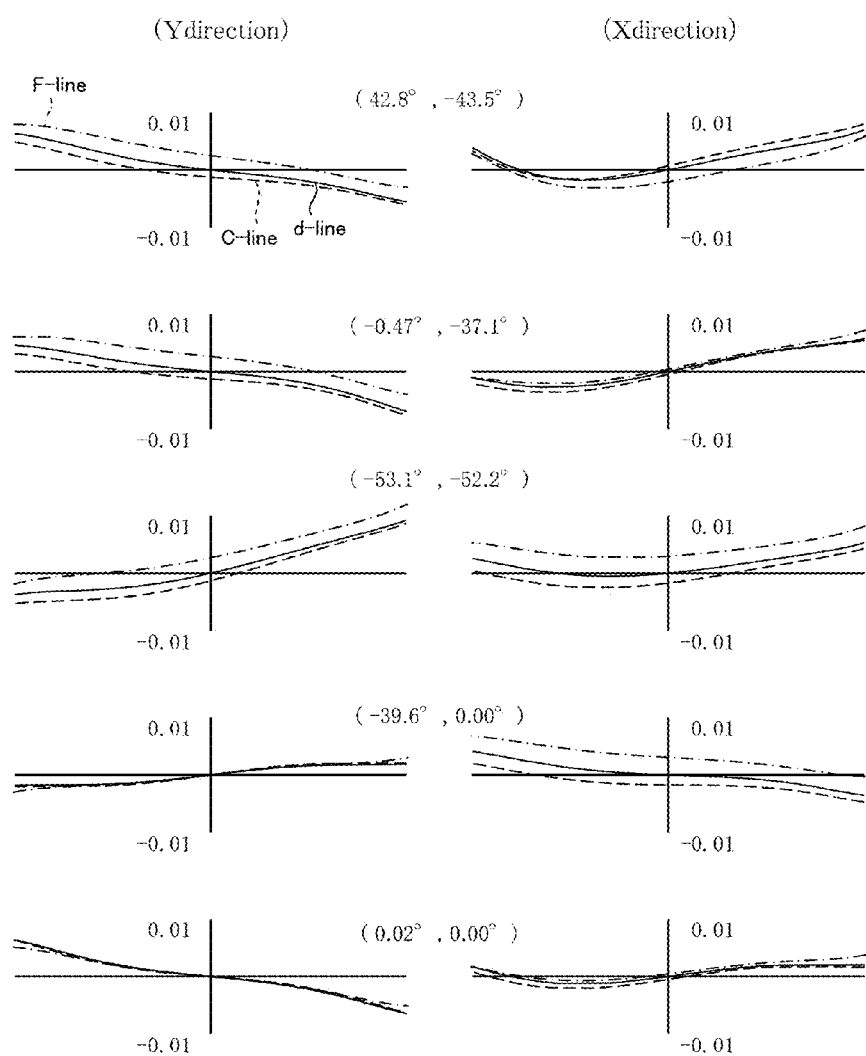
FIG. 35 is a lateral aberration diagram of the optical system 1 according to Example 8.
Figure 36:
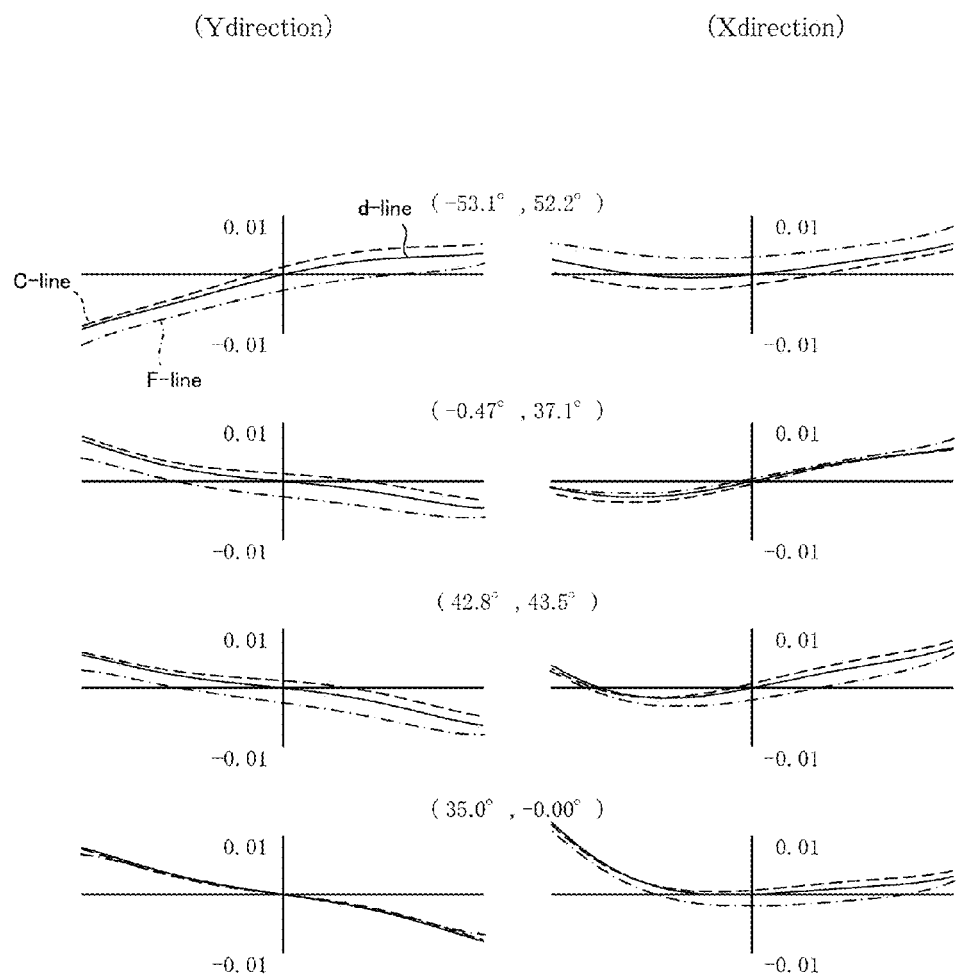
FIG. 36 is a lateral aberration diagram of the optical system 1 according to Example 8.

FIG. 33 is a cross-sectional view including a first front group central axis Cf1 and a second front group central axis Cf2 of the optical system 1 according to Example 8. FIG. 34 is a view as seen from a direction perpendicular to that of FIG. 33. FIGS. 35 and 36 are each a lateral aberration diagram of the optical system 1 according to Example 8.

As illustrated in FIG. 33, the optical system 1 of Example 8 includes, in order from the object side to the image side, a front group Gf, a back group Gb, and a back deflection group Gbv. The front group Gf includes a first front group Gf1 having a first front group central axis Cf1 and a second front group Gf2 having a second front group central axis Cf2 extending parallel to the first front group central axis Cf1. The back group Gb has a single back group central axis Cb. The back deflection group Gbv is disposed between the back group Gb and the image plane I.

Parallel arrangement of the first front group Gf1 and second front group Gf2 allows stereoscopic observation.

The first front group Gf1 preferably includes a first front first group $Gf1_1$ including a flat-concave negative lens $Lf1_{11}$ whose flat surface faces the object side, a first front second group $Gf1_2$ including a cemented lens $SUf1_{21}$ composed of a concave-concave negative lens $Lf1_{21}$ and a convex-convex positive lens $Lf1_{22}$, a first front third group $Gf1_3$ including a cemented lens $SUf1_{31}$ composed of a negative meniscus lens $Lf1_{31}$ whose convex surface faces the object side and a convex-convex positive lens $Lf1_{32}$, and a first stop S1. A surface of the flat-concave negative lens $Lf1_{11}$ on the image side is an aspheric surface.

The second front group Gf2 preferably includes a second front first group $Gf2_1$ including a flat-concave negative lens $Lf2_{11}$ whose flat surface faces the object side, a second front second group $Gf2_2$ including a cemented lens $SUf2_{21}$ composed of a concave-concave negative lens $Lf2_{21}$ and a convex-convex positive lens $Lf2_{22}$, a second front third group $Gf2_3$ including a cemented lens $SUf2_{31}$ composed of a negative meniscus lens $Lf2_{31}$ whose convex surface faces the object side and a convex-convex positive lens $Lf2_{32}$, and a second stop S2. A surface of the flat-concave negative lens $Lf2_{11}$ on the image side is an aspheric surface.

The back group Gb preferably includes a back first group Gb1 including a convex-convex positive lens $Lb_1$ and a concave-concave negative lens $Lb_2$.

The back deflection group Gbv is disposed between the back group Gb and the image plane I and includes a back deflection member Lbv that deflects the first and second light beams L1 and L2. The back deflection member Lbv preferably performs deflection so as to reduce convergence of the first and second light beams L1 and L2 that have exited from the back group Gb and to make an absolute value of an incident angle of the first and second light beams L1 and L2 onto the image plane I smaller than an absolute value of an incident angle thereof onto the back deflection group Gbv.

A first light beam L1 entering the first front group Gf1 from a first object plane passes through the flat-concave negative lens $Lf1_{11}$ of the first front first group $Gf1_1$, the cemented lens $SUf1_{21}$ of the first front second group $Gf1_2$, the cemented lens $SUf1_{31}$ of the first front third group $Gf1_3$, and the first stop S1, exits from the first front group Gf1, and, thereafter, enters the back group Gb.

A second light beam L2 entering the second front group Gf2 from a second object plane passes through the flat-concave negative lens $Lf2_{11}$ of the second front first group $Gf2_1$, the cemented lens $SUf2_{21}$ of the second front second group $Gf2_2$, the cemented lens $SUf2_{31}$ of the second front third group $Gf2_3$, and the second stop S2, exits from the second front group Gf2, and, thereafter, enters the back group Gb.

The first and second light beams L1 and L2 entering the back group Gb pass through the convex-convex positive lens $Lb_1$ and a concave-concave negative lens $Lb_2$ of the back first group Gb1 and the back deflection member Lbv of the back deflection group Gbv, and then enter the image plane.

As illustrated in FIG. 33, in the optical system 1 according to Example 8, the back deflection group Gbv includes the back deflection member Lbv, and the back deflection member Lbv is an optical device having a thickness in a direction of the back group central axis Cb which increases toward an outer peripheral side with respect to the back group central axis Cb.

Using the back deflection member Lbv having a refraction function to constitute the back deflection group Gbv allows the back deflection group Gbv to be formed by polishing or molding, thereby making it possible to significantly improve productivity.

Further, in the Example 8, the back deflection member Lbv is an optical device having a wedge prism shape.

Forming the back deflection member Lbv into a wedge prism shape allows both surfaces of the back deflection member Lbv to be formed as a plane, thereby making it possible to significantly improve productivity.

Figure 37:
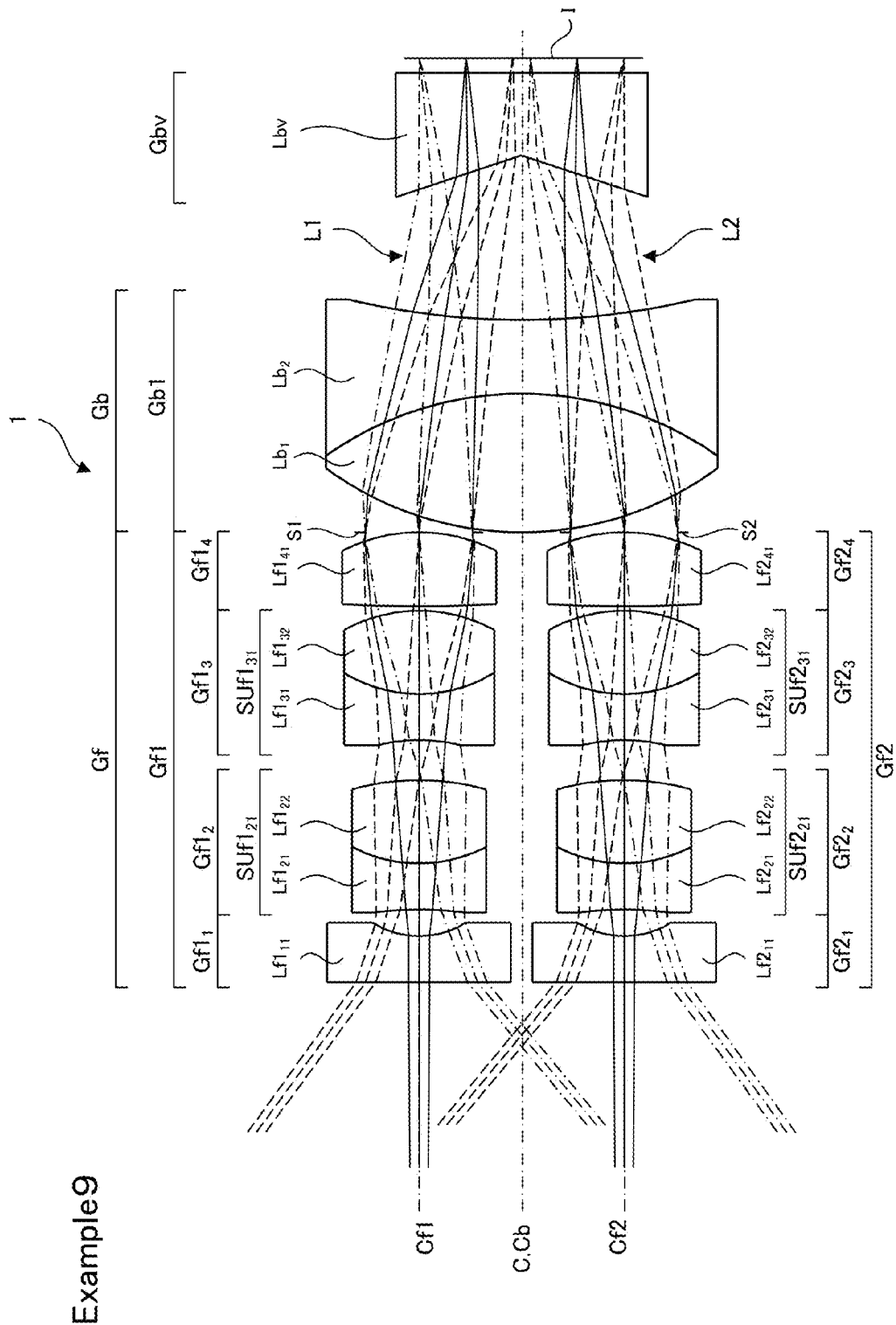
FIG. 37 is a cross-sectional view including a first front group central axis Cf1 and a second front group central axis Cf2 of the optical system 1 according to Example 9.
Figure 38:
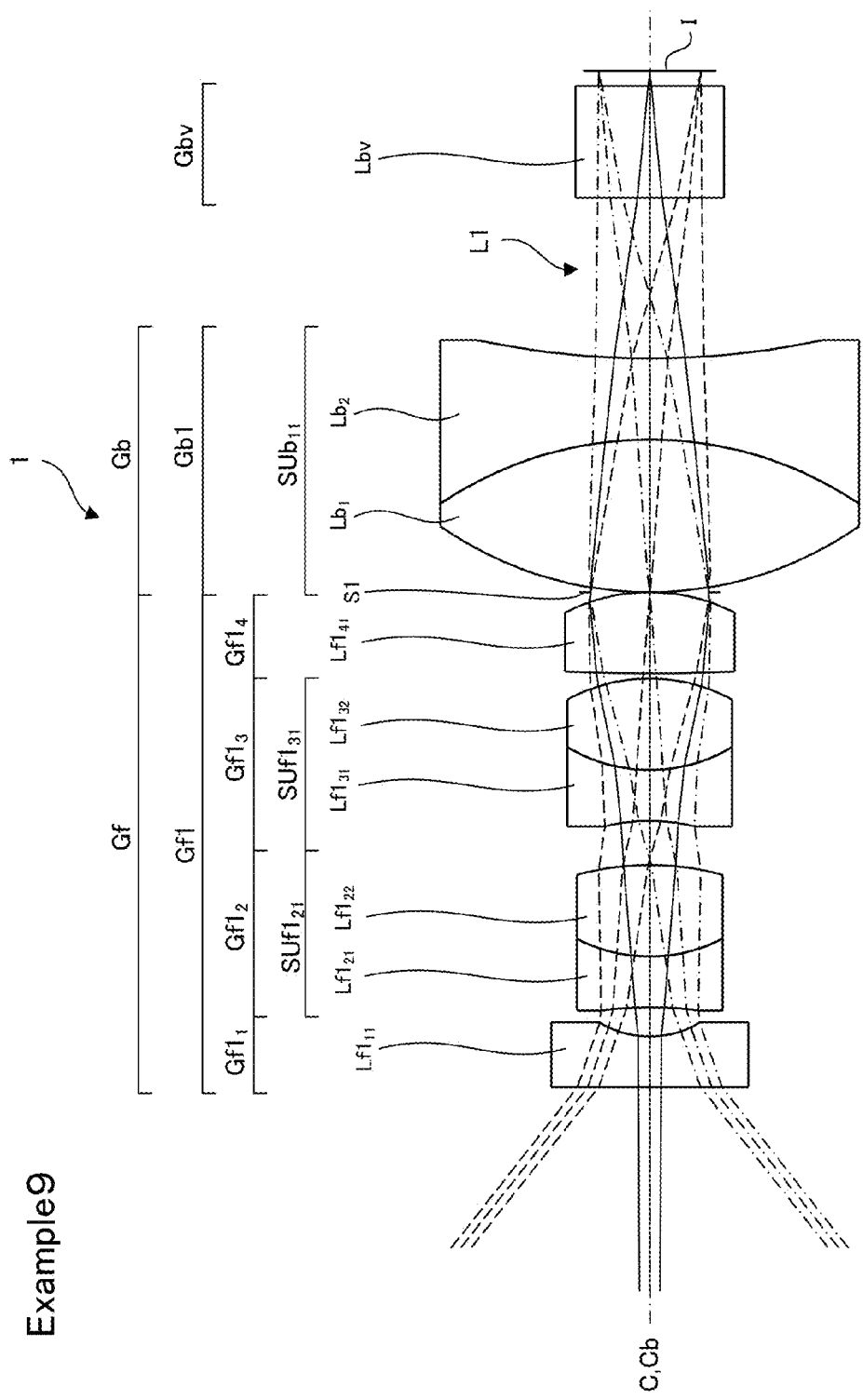
FIG. 38 is a view as seen from a direction perpendicular to that of FIG. 37.
Figure 39:
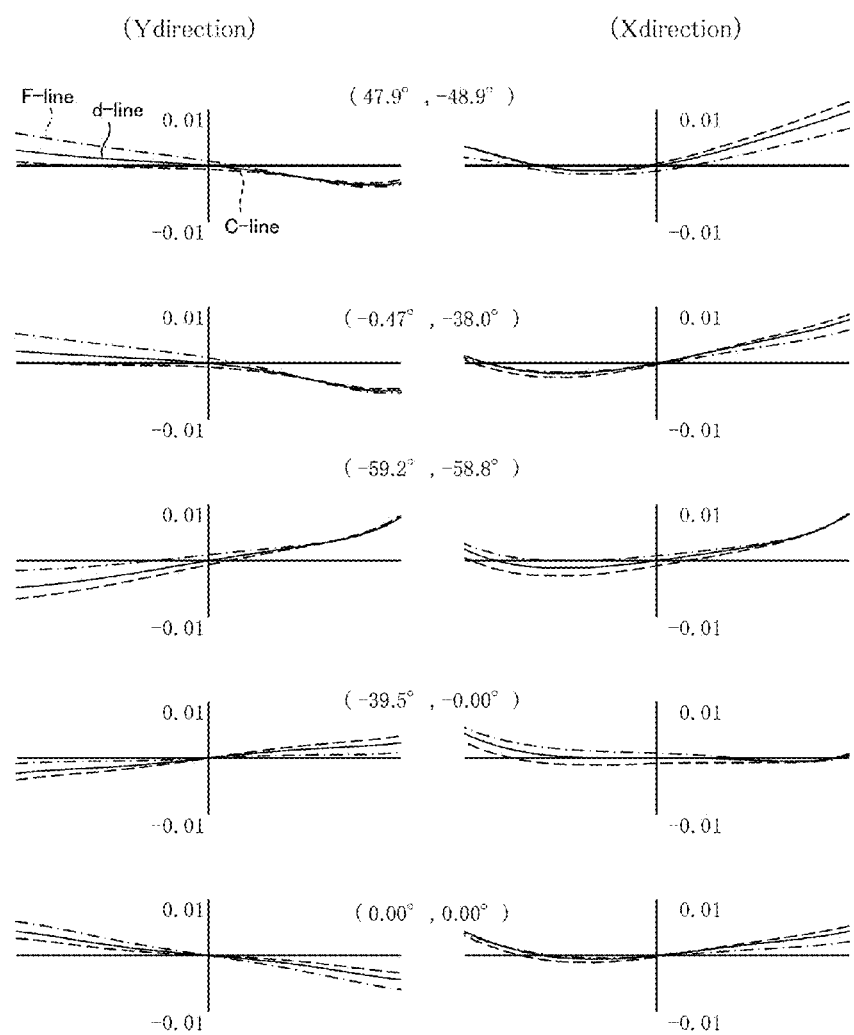
FIG. 39 is a lateral aberration diagram of the optical system 1 according to Example 9.
Figure 40:
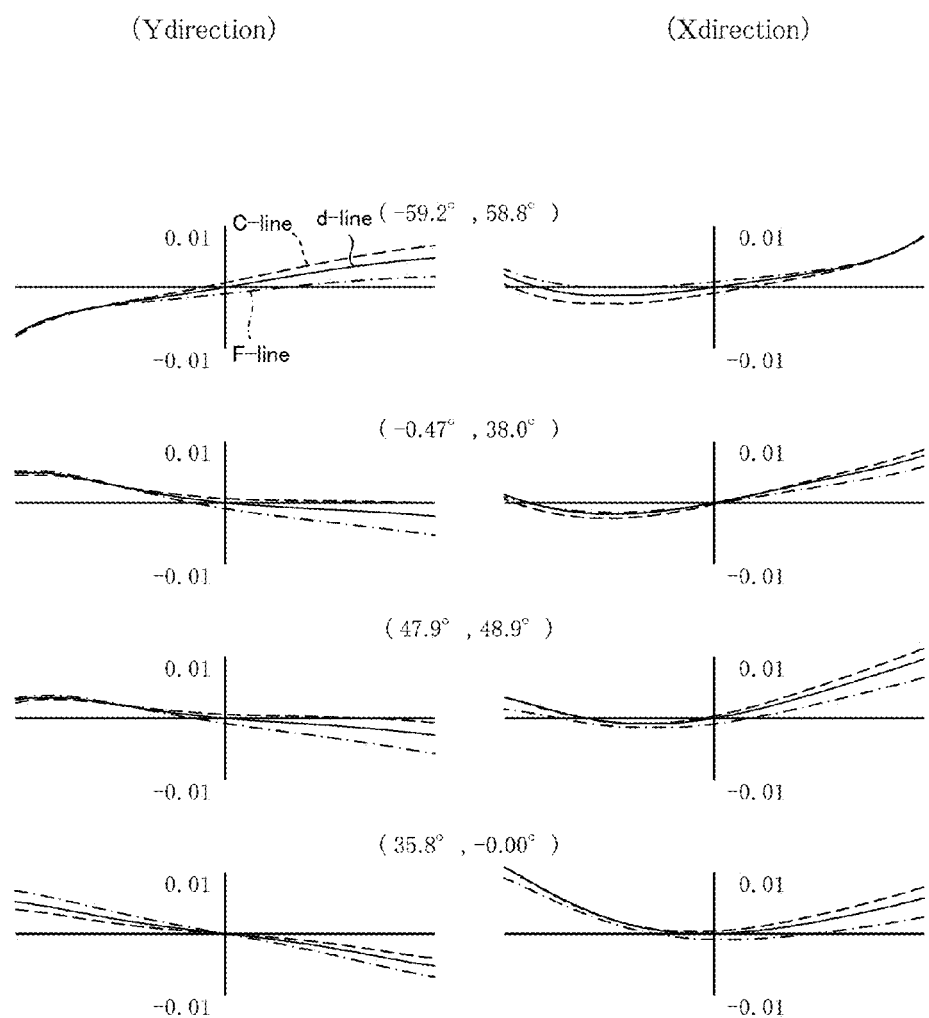
FIG. 40 is a lateral aberration diagram of the optical system 1 according to Example 9.

FIG. 37 is a cross-sectional view including a first front group central axis Cf1 and a second front group central axis Cf2 of the optical system 1 according to Example 9. FIG. 38 is a view as seen from a direction perpendicular to that of FIG. 37. FIGS. 39 and 40 are each a lateral aberration diagram of the optical system 1 according to Example 9.

As illustrated in FIG. 37, the optical system 1 of Example 9 includes, in order from the object side to the image side, a front group Gf, a back group Gb, and a back deflection group Gbv. The front group Gf includes a first front group Gf1 having a first front group central axis Cf1 and a second front group Gf2 having a second front group central axis Cf2 extending parallel to the first front group central axis Cf1. The back group Gb has a single back group central axis Cb. The back deflection group Gbv is disposed between the back group Gb and the image plane I.

Parallel arrangement of the first front group Gf1 and second front group Gf2 allows stereoscopic observation.

The first front group Gf1 preferably includes a first front first group $Gf1_1$ including a flat-concave negative lens $Lf1_{11}$ whose flat surface faces the object side, a first front second group $Gf1_2$ including a cemented lens $SUf1_{21}$ composed of a concave-concave negative lens $Lf1_{21}$ and a convex-convex positive lens $Lf1_{22}$, a first front third group $Gf1_3$ including a cemented lens $SUf1_{31}$ composed of a concave-concave negative lens $Lf1_{31}$ and a convex-convex positive lens $Lf1_{32}$, a first front fourth group $Gf1_4$ including a convex-convex positive lens $Lf1_{41}$, and a first stop S1. A surface of the flat-concave negative lens $Lf1_{11}$ on the image side is an aspheric surface.

The second front group Gf2 preferably includes a second front first group $Gf2_1$ including a flat-concave negative lens $Lf2_{11}$ whose flat surface faces the object side, a second front second group $Gf2_2$ including a cemented lens $SUf2_{21}$ composed of a concave-concave negative lens $Lf2_{21}$ and a convex-convex positive lens $Lf2_{22}$, a second front third group $Gf2_3$ including a cemented lens $SUf2_{31}$ composed of a concave-concave negative lens $Lf2_{31}$ and a convex-convex positive lens $Lf2_{32}$, a second front fourth group $Gf2_4$ including a convex-convex positive lens $Lf2_{41}$, and a second stop S2. A surface of the flat-concave negative lens $Lf2_{11}$ on the image side is an aspheric surface.

The back group Gb preferably includes a back first group Gb1 including a cemented lens $SUb1_{11}$ composed of a convex-convex positive lens $Lb_1$ and a concave-concave negative lens $Lb_2$.

The back deflection group Gbv is disposed between the back group Gb and the image plane I and includes a back deflection member Lbv that deflects the first and second light beams L1 and L2. The back deflection member Lbv preferably performs deflection so as to reduce convergence of the first and second light beams L1 and L2 that have exited from the back group Gb and to make an absolute value of an incident angle of the first and second light beams L1 and L2 onto the image plane I smaller than an absolute value of an incident angle thereof onto the back deflection group Gbv.

A first light beam L1 entering the first front group Gf1 from a first object plane passes through the flat-concave negative lens $Lf1_{11}$ of the first front first group $Gf1_1$, the cemented lens $SUf1_{21}$ of the first front second group $Gf1_2$, the cemented lens $SUf1_{31}$ of the first front third group $Gf1_3$, and the first stop S1, exits from the first front group Gf1, and, thereafter, enters the back group Gb.

A second light beam L2 entering the second front group Gf2 from a second object plane passes through the flat-concave negative lens $Lf2_{11}$ of the second front first group $Gf2_1$, the cemented lens $SUf2_{21}$ of the second front second group $Gf2_2$, the cemented lens $SUf2_{31}$ of the second front third group $Gf2_3$, and the second stop S2, exits from the second front group Gf2, and, thereafter, enters the back group Gb.

The first and second light beams L1 and L2 entering the back group Gb pass through the cemented lens $SUb1_{11}$ of the back first group Gb1 and the back deflection member Lbv of the back deflection group Gbv, and then enter the image plane.

As illustrated in FIG. 37, in the optical system 1 according to Example 9, the back deflection group Gbv includes the back deflection member Lbv, and the back deflection member Lbv is an optical device having a thickness in a direction of the back group central axis Cb which increases toward an outer peripheral side with respect to the back group central axis Cb.

Using the back deflection member Lbv having a refraction function to constitute the back deflection group Gbv allows the back deflection group Gbv to be formed by polishing or molding, thereby making it possible to significantly improve productivity.

Further, in the Example 9, the back deflection member Lbv is an optical device having a wedge prism shape.

Forming the back deflection member Lbv into a wedge prism shape allows both surfaces of the back deflection member Lbv to be formed as a plane, thereby making it possible to significantly improve productivity.

Figure 41:
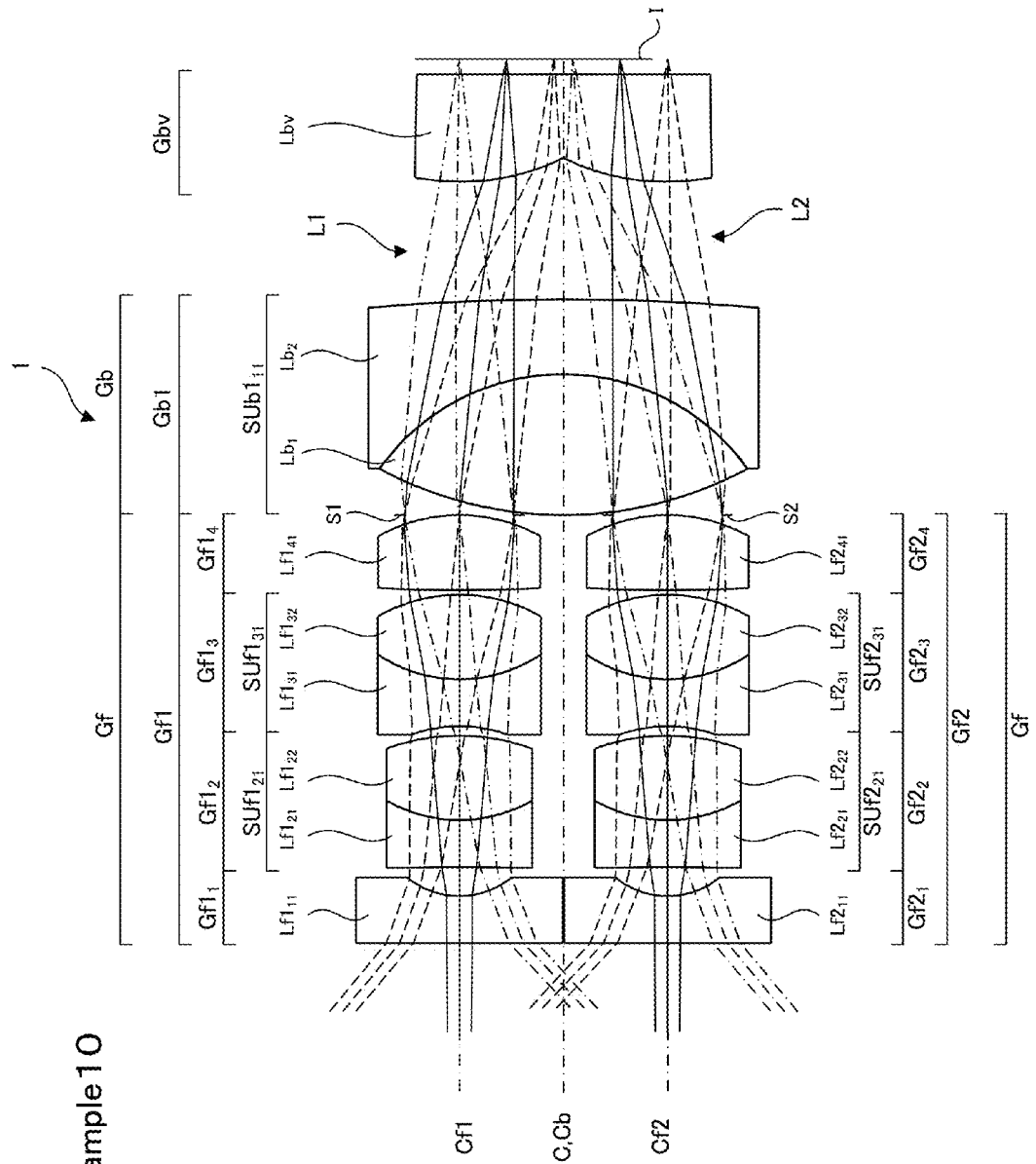
FIG. 41 is a cross-sectional view including a first front group central axis Cf1 and a second front group central axis Cf2 of the optical system 1 according to Example 10.
Figure 42:
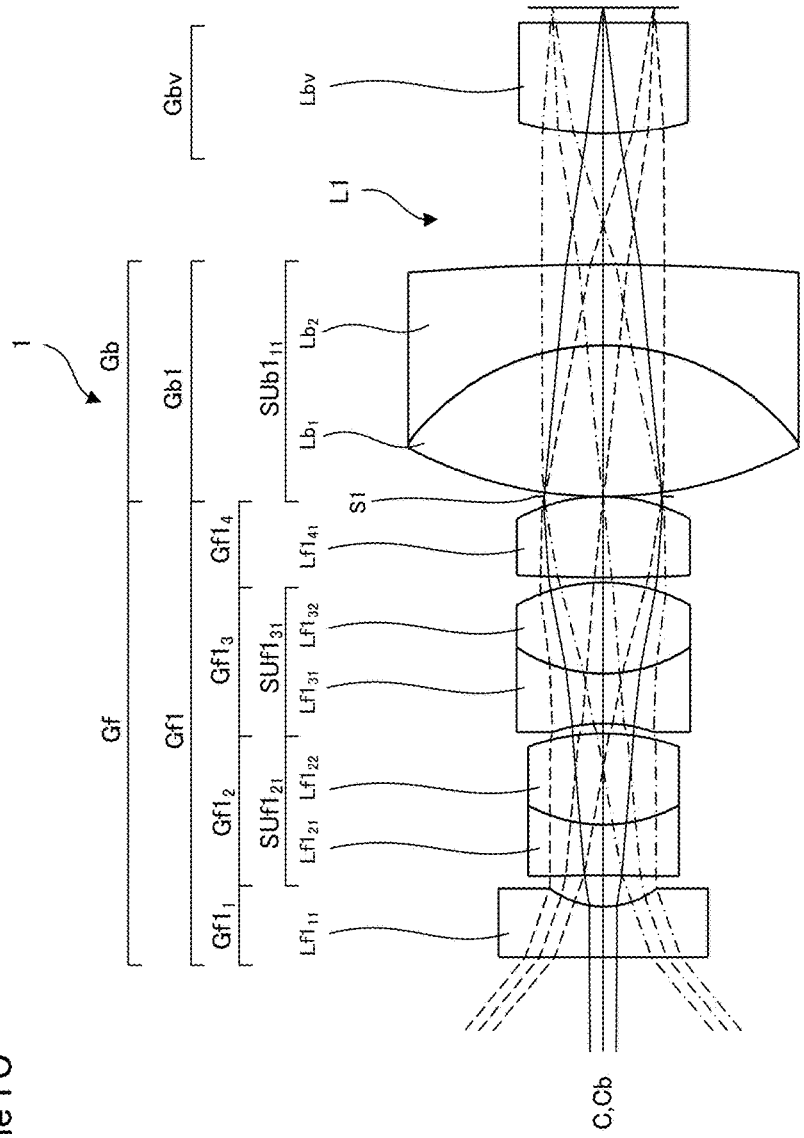
FIG. 42 is a view as seen from a direction perpendicular to that of FIG. 41.
Figure 43:
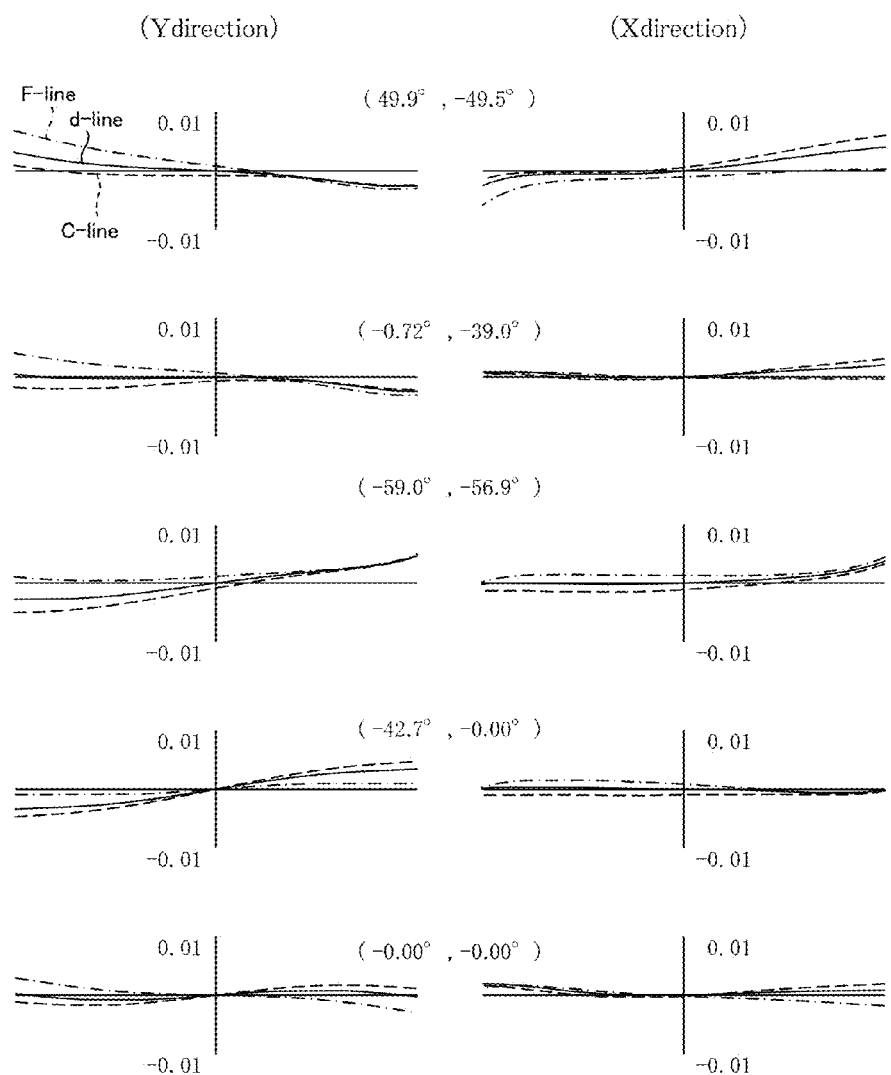
FIG. 43 is a lateral aberration diagram of the optical system 1 according to Example 10.
Figure 44:
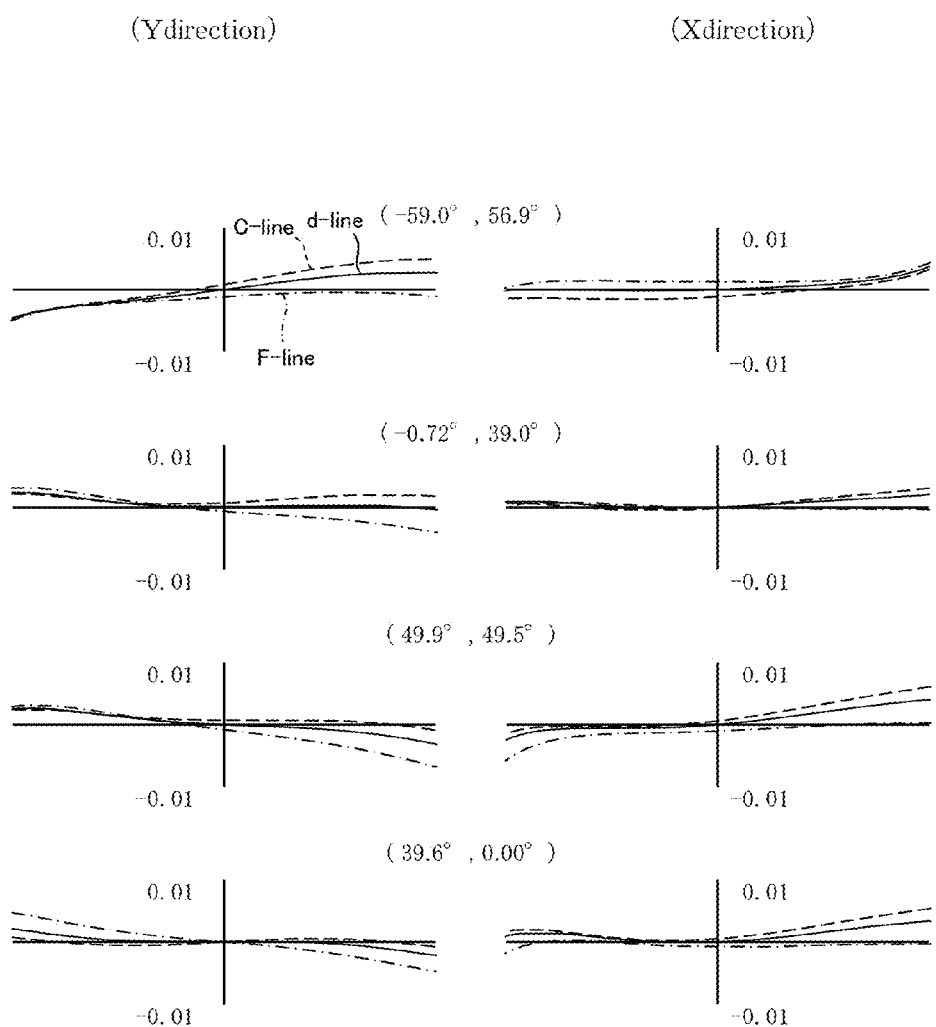
FIG. 44 is a lateral aberration diagram of the optical system 1 according to Example 10.

FIG. 41 is a cross-sectional view including a first front group central axis Cf1 and a second front group central axis Cf2 of the optical system 1 according to Example 10. FIG. 42 is a view as seen from a direction perpendicular to that of FIG. 41. FIGS. 43 and 44 are each a lateral aberration diagram of the optical system 1 according to Example 10.

As illustrated in FIG. 41, the optical system 1 of Example 10 includes, in order from the object side to the image side, a front group Gf, a back group Gb, and a back deflection group Gbv. The front group Gf includes a first front group Gf1 having a first front group central axis Cf1 and a second front group Gf2 having a second front group central axis Cf2 extending parallel to the first front group central axis Cf1. The back group Gb has a single back group central axis Cb. The back deflection group is disposed between the back group Gb and the image plane I.

Parallel arrangement of the first front group Gf1 and second front group Gf2 allows stereoscopic observation.

The first front group Gf1 preferably includes a first front first group Gf1$_1$ including a flat-concave negative lens Lf1$_{11}$ whose flat surface faces the object side, a first front second group Gf1$_2$ including a cemented lens SUf1$_{21}$ composed of a concave-concave negative lens Lf1$_{21}$ and a convex-convex positive lens Lf1$_{22}$, a first front third group Gf1$_3$ including a cemented lens SUf1$_{31}$ composed of a concave-concave negative lens Lf1$_{31}$ and a convex-convex positive lens Lf1$_{32}$, a first front fourth group Gf1$_4$ including a convex-convex positive lens Lf1$_{41}$, and a first stop S1. A surface of the flat-concave negative lens Lf1$_{11}$ on the image side is an aspheric surface.

The second front group Gf2 preferably includes a second front first group Gf2$_1$ including a flat-concave negative lens Lf2$_{11}$ whose flat surface faces the object side, a second front second group Gf2$_2$ including a cemented lens SUf2$_{21}$ composed of a concave-concave negative lens Lf2$_{21}$ and a convex-convex positive lens Lf2$_{22}$, a second front third group Gf2$_3$ including a cemented lens SUf2$_{31}$ composed of a concave-concave negative lens Lf2$_{31}$ and a convex-convex positive lens Lf2$_{32}$, a second front fourth group Gf2$_4$ including a convex-convex positive lens Lf2$_{41}$, and a second stop S2. A surface of the flat-concave negative lens Lf2$_{11}$ on the image side is an aspheric surface.

The back group Gb preferably includes a back first group Gb1 including a cemented lens SUb1$_{11}$ composed of a convex-convex positive lens Lb$_1$ and a negative meniscus lens Lb$_2$ whose convex surface faces the image plane I side.

The back deflection group Gbv is disposed between the back group Gb and the image plane I and includes a back deflection member Lbv that deflects the first and second light beams L1 and L2. The back deflection member Lbv preferably performs deflection so as to reduce convergence of the first and second light beams L1 and L2 that have exited from the back group Gb and to make an absolute value of an incident angle of the first and second light beams L1 and L2 onto the image plane I smaller than an absolute value of an incident angle thereof onto the back deflection group Gbv.

A first light beam L1 entering the first front group Gf1 from a first object plane passes through the flat-concave negative lens Lf1$_{11}$ of the first front first group Gf1$_1$, the cemented lens SUf1$_{21}$ of the first front second group Gf1$_2$, the cemented lens SUf1$_{31}$ of the first front third group Gf1$_3$, and the first stop S1, exits from the first front group Gf1, and, thereafter, enters the back group Gb.

A second light beam L2 entering the second front group Gf2 from a second object plane passes through the flat-concave negative lens Lf2$_{11}$ of the second front first group Gf2$_1$, the cemented lens SUf2$_{21}$ of the second front second group Gf2$_2$, the cemented lens SUf2$_{31}$ of the second front third group Gf2$_3$, and the second stop S2, exits from the second front group Gf2, and, thereafter, enters the back group Gb.

The first and second light beams L1 and L2 entering the back group Gb pass through the cemented lens SUb1$_{11}$ of the back first group Gb1 and the back deflection member Lbv of the back deflection group Gbv, and then enter the image plane.

Further, in the optical system 1 of Example 10, the back deflection group Gbv includes an optical device having a curved surface.

When the back deflection member Lbv includes a curved surface, it is possible to set more freely an angle of the light beam entering into the image plane. This can further improve telecentricity of the principal ray with respect to image height after the principal ray exits from the back group Gb and image plane curvature. More preferably, the curved surface may be a spherical surface, a toric surface, an anamorphic surface, or a free-form surface.

The back deflection member Lbv can be used in any of the above Examples 1 to 10.

The following describes configuration parameters in the above Examples 1 to 10.

A coordinate system is defined for each surface. A direction directed from an origin O of the coordinate system on which the surface is defined toward the image plane along the central axis is defined as a Z-axis positive direction. A direction directed from the second front group central axis Cf2 toward the first front group central axis Cf1 on the same surface is defined as an X-axis positive direction. A Y-axis positive direction is defined by a right-hand coordinate system.

In the case where, of the optical surfaces forming the optical system in each Example, a specific surface and the subsequent surface form together a coaxial optical system, surface separations are given to them. In addition, radii of curvatures of surfaces, refractive indices of media and Abbe constants are given as usual.

Given to each eccentric surface are an eccentric amount of the coordinate system on which that surface is defined from the origin O (X, Y and Z in the X-, Y- and Z-axis directions) and the angles ($\alpha$, $\beta$, $\gamma$(°)) of tilt of the coordinate system for defining each surface with the X-, Y- and Z-axes of the coordinate system defined on the origin as center. Then, the positive $\alpha$ and $\beta$ mean counterclockwise rotation with respect to the positive directions of the respective axes, and the positive $\gamma$ means clockwise rotation with respect to the positive direction of the Z-axis. Referring here to the $\alpha$, $\beta$, $\gamma$ rotation of the center axis of a certain surface, the coordinate system for defining each surface is first $\alpha$ rotated counterclockwise about the X-axis of the coordinate system defined on the origin of an optical system. Then, the center axis of the rotated surface is $\beta$ rotated counterclockwise about the Y-axis of a new coordinate system. Finally, the center axis is $\gamma$ rotated clockwise about the Z-axis of a rotated new coordinate system.

Refractive indices and Abbe constants on d-line (wavelength: 587.56 nm) basis are given, and length is given in mm. The eccentric of each surface is expressed by the eccentric amount from the reference surface as described above. The symbol "∞" affixed to the radius of curvature stands for infinity.

Aspheric data used in the present embodiment include data about aspheric lens surfaces. Aspheric surface shape or configuration may be represented by the following formula (a):

$$Z=(y^2/r)/[1+\{1-(1+K)\cdot(y/r)^2\}^{1/2}]+A4y^4+A6y^6+A8y^8+A10y^{10} \quad (a)$$

where $z$ is indicative of an optical axis where the direction of travel of light is positive, and $y$ is indicative of a direction perpendicular to the optical axis.

In the above formula, $r$ is a paraxial radius of curvature, $K$ is the conic coefficient, and A4, A6 and A8 are the 4th, 6th and 8th order aspheric coefficients, respectively. Note here that the symbol "e" indicates that the subsequent numerical value is a power exponent having 10 as a base. For instance, "1.0e-5" means "1.0×10$^{-5}$".

A surface shape of the free-form surface FFS used in the present embodiment is defined by the following formula (b). Note here that the Z-axis of that defining formula is the axis of the free-form surface FFS, and that a coefficient term with no data described is zero.

$$Z = (r^2/R)/\left[1 + \sqrt{\{1-(1+k)(r/R)^2\}}\right] + \sum_{j=1}^{66} C_j X^m Y^m \quad (b)$$

Here the first term of Formula (a) is the spherical term, and the second term is the free-form surface term.

In the spherical term,
R is the radius of curvature of the apex,
k is the conic constant, and
r is $\sqrt{(X^2+Y^2)}$.

The free-form surface term is:

$\sum_{j=1}^{66} C_j X^m Y^n$ $= C_1$
$+C_2 X + C_3 Y$
$+C_4 X^2 + C_5 XY + C_6 Y^2$
$+C_7 X^3 + C_8 X^2 Y + C_9 XY^2 + C_{10} Y^3$
$+C_{11} X^4 + C_{12} X^3 Y + C_{13} X^2 Y^2 + C_{14} XY^3 + C_{15} Y^4$
$+C_{16} X^5 + C_{17} X^4 Y + C_{18} X^3 Y^2 + C_{19} X^2 Y^3 + C_{20} XY^4$
$+C_{21} Y^5$
$+C_{22} X^6 + C_{23} X^5 Y + C_{24} X^4 Y^2 + C_{25} X^3 Y^3 + C_{26} X^2 Y^4$
$+C_{27} XY^5 + C_{28} Y^6$
$+C_{29} X^7 + C_{30} X^6 Y + C_{31} X^5 Y^2 + C_{32} X^4 Y^3 + C_{33} X^3 Y^4$
$+C_{34} X^2 Y^5 + C_{35} XY^6 + C_{36} Y^7$
. . . .

where $C_j$ (j is an integer of 1 or greater) is a coefficient.

It is here to be noted that the defining formula (b) is provided for the purpose of illustration alone. The free-form surface according to the present invention has a feature of using a rotationally asymmetric surface thereby making correction for rotationally asymmetric aberrations occurring from eccentricity while, at the same time, improving productivity. As a matter of course, the same effect is achievable for any other defining formula too.

Example 1

| Surface No. | Radius of curvature | Surface separation | Eccentricity | Refractive index | Abbe number |
|---|---|---|---|---|---|
| Object plane | ∞ | 16.000 | | | |
| 1 | ∞ | 0.600 | | 1.8830 | 40.7 |
| 2 | 1.780 | 0.805 | | | |
| 3 | −1.761 | 0.600 | | 1.8830 | 40.7 |
| 4 | 3.212 | 1.000 | | 1.9229 | 18.9 |
| 5 | −4.531 | 1.186 | | | |
| 6 | 4.215 | 0.600 | | 1.8830 | 40.7 |
| 7 | 1.261 | 0.800 | | 1.4875 | 70.2 |
| 8 | −4.965 | 0.200 | | | |
| 9 | Stop plane | 0.600 | | | |
| 10 | −4.839 | 1.000 | | 1.4875 | 70.2 |
| 11 | −1.839 | 0.300 | | | |
| 12 | Reference plane | 0.000 | Eccentricity (1) | | |
| 13 | 5.239 | 2.800 | | 1.8467 | 23.8 |
| 14 | −7.173 | 1.000 | | 1.9229 | 18.9 |
| 15 | 3.535 | 0.500 | | | |
| 16 | 5.438 | 3.779 | | 1.8830 | 40.7 |
| 17 | −13.184 | 0.500 | | | |
| 18 | ∞ | 1.000 | | 1.5163 | 64.1 |
| 19 | ∞ | 0.100 | | | |
| Image plane | ∞ | | Eccentricity (2) | | |

Eccentricity [1]

| X | 2.00 | Y | 0.00 | Z | 0.00 |
|---|---|---|---|---|---|
| α | 0.00 | β | 0.00 | γ | 0.00 |

Eccentricity [2]

| X | −0.70 | Y | −0.00 | Z | 0.00 |
|---|---|---|---|---|---|
| α | 0.00 | β | 0.00 | γ | 0.00 |

Specifications

| Base length (entrance pupil interval) | 4 mm |
|---|---|
| Angle of view (diagonal) | 140° |
| Stop diameter | φ1.0 mm |
| Image size | φ1.00 mm |
| Focal distance | 1.105 mm |
| Effective Fno | 5.07 |

Example 2

| Surface No. | Radius of curvature | Surface separation | Eccentricity | Refractive index | Abbe number |
|---|---|---|---|---|---|
| Object plane | ∞ | 16.000 | | | |
| 1 | ∞ | 0.600 | | 1.8830 | 40.7 |
| 2 | 2.078 | 1.760 | | | |
| 3 | −3.800 | 0.600 | | 1.8830 | 40.7 |
| 4 | 4.946 | 0.800 | | 1.9229 | 18.9 |
| 5 | −5.853 | 3.717 | | | |
| 6 | 6.030 | 0.600 | | 1.8830 | 40.7 |
| 7 | 1.228 | 0.800 | | 1.4875 | 70.2 |
| 8 | −4.995 | 0.200 | | | |
| 9 | Stop plane | 0.600 | | | |
| 10 | −5.355 | 0.800 | | 1.4875 | 70.2 |
| 11 | −1.740 | 0.300 | | | |
| 12 | Reference plane | 0.000 | Eccentricity (1) | | |
| 13 | 4.806 | 1.908 | | 1.8467 | 23.8 |
| 14 | −19.258 | 1.000 | | 1.9229 | 18.9 |
| 15 | 3.473 | 0.290 | | | |
| 16 | 6.706 | 4.035 | | 1.8830 | 40.7 |
| 17 | −79.279 | 0.500 | | | |
| 18 | ∞ | 1.000 | | 1.5163 | 64.1 |
| 19 | ∞ | 0.100 | | | |
| Image plane | ∞ | | Eccentricity (2) | | |

Eccentricity [1]

| X | 1.50 | Y | 0.00 | Z | 0.00 |
|---|---|---|---|---|---|
| α | 0.00 | β | 0.00 | γ | 0.00 |

Eccentricity [2]

| X | −0.70 | Y | 0.00 | Z | 0.00 |
|---|---|---|---|---|---|
| α | 0.00 | β | 0.00 | γ | 0.00 |

Specifications

| Base length (entrance pupil interval) | 3 mm |
|---|---|
| Angle of view (diagonal) | 140° |
| Stop diameter | φ1.0 mm |
| Image size | φ1.00 mm |

-continued

| | | |
|---|---|---|
| Focal distance | 1.035 mm | |
| Effective Fno | 4.67 | |

Example 3

| Surface No. | Radius of curvature | Surface separation | Eccentricity | Refractive index | Abbe number |
|---|---|---|---|---|---|
| Object plane | ∞ | 16.000 | | | |
| 1 | ∞ | 0.600 | | 1.8830 | 40.7 |
| 2 | 1.646 | 1.515 | | | |
| 3 | −6.519 | 0.600 | | 1.8830 | 40.7 |
| 4 | 1.829 | 1.000 | | 1.9229 | 18.9 |
| 5 | −129.380 | 5.136 | | | |
| 6 | Stop plane | 0.00 | | | |
| 7 | 2.007 | 0.600 | | 1.8830 | 40.7 |
| 8 | 1.216 | 1.000 | | 1.4875 | 70.2 |
| 9 | −5.462 | 0.200 | | | |
| 10 | Reference plane | 0.000 | Eccentricity (1) | | |
| 11 | 6.267 | 1.200 | | 1.8973 | 22.4 |
| 12 | −6.950 | 1.000 | | 1.9229 | 18.9 |
| 13 | 4.982 | 0.467 | | | |
| 14 | 18.257 | 4.437 | | 1.9229 | 18.9 |
| 15 | −19.936 | 0.500 | | | |
| 16 | ∞ | 1.000 | | 1.5163 | 64.1 |
| 17 | ∞ | 0.100 | | | |
| Image plane | ∞ | | Eccentricity (2) | | |

Eccentricity [1]

| X | 1.00 | Y | 0.00 | Z | 0.00 |
|---|---|---|---|---|---|
| α | 0.00 | β | 0.00 | γ | 0.00 |

Eccentricity [2]

| X | −0.70 | Y | 0.00 | Z | 0.00 |
|---|---|---|---|---|---|
| α | 0.00 | β | 0.00 | γ | 0.00 |

Specifications

| | |
|---|---|
| Base length (entrance pupil interval) | 2 mm |
| Angle of view (diagonal) | 140° |
| Stop diameter | φ1.0 mm |
| Image size | φ1.00 mm |
| Focal distance | 1.046 mm |
| Effective Fno | 5.82 |

Example 4

| Surface No. | Radius of curvature | Surface separation | Eccentricity | Refractive index | Abbe number |
|---|---|---|---|---|---|
| Object plane | ∞ | 16.000 | | | |
| 1 | ∞ | 0.600 | | 1.8830 | 40.7 |
| 2 | 1.407 | 2.216 | | | |
| 3 | −72.977 | 0.500 | | 1.8830 | 40.7 |
| 4 | 2.693 | 1.000 | | 1.8081 | 22.8 |
| 5 | −4.310 | 0.692 | | | |
| 6 | Stop plane | 0.544 | | | |
| 7 | 6.678 | 0.500 | | 1.9229 | 18.9 |
| 8 | 1.719 | 0.800 | | 1.7880 | 47.3 |
| 9 | −3.971 | 0.200 | | | |
| 10 | Reference plane | 0.000 | Eccentricity (1) | | |
| 11 | 3.866 | 1.200 | | 1.6204 | 60.3 |
| 12 | −222.046 | 1.000 | | 1.8830 | 40.7 |
| 13 | 3.239 | 0.400 | | | |
| 14 | 5.702 | 1.000 | | 1.8830 | 40.7 |
| 15 | −38.833 | 0.200 | | | |
| 16 | ∞ | 1.000 | | 1.5163 | 64.1 |
| 17 | ∞ | 0.100 | | | |
| Image plane | ∞ | | Eccentricity (2) | | |

Eccentricity [1]

| X | 1.00 | Y | 0.00 | Z | 0.00 |
|---|---|---|---|---|---|
| α | 0.00 | β | 0.00 | γ | 0.00 |

Eccentricity [2]

| X | −0.70 | Y | 0.00 | Z | 0.00 |
|---|---|---|---|---|---|
| α | 0.00 | β | 0.00 | γ | 0.00 |

Specifications

| | |
|---|---|
| Base length (entrance pupil interval) | 2 mm |
| Angle of view (diagonal) | 120° |
| Stop diameter | φ0.9 mm |
| Image size | φ1.00 mm |
| Focal distance | 1.104 mm |
| Effective Fno | 3.80 |

Example 5

| Surface No. | Radius of curvature | Surface separation | Eccentricity | Refractive index | Abbe number |
|---|---|---|---|---|---|
| Object plane | ∞ | 16.000 | | | |
| 1 | ∞ | 0.600 | | 1.8830 | 40.7 |
| 2 | 1.246 | 1.495 | | | |
| 3 | −10.577 | 0.500 | | 1.8830 | 40.7 |
| 4 | 1.336 | 0.800 | | 1.8081 | 22.8 |
| 5 | −2.947 | 0.505 | | | |
| 6 | Stop plane | 0.100 | | | |
| 7 | 25.912 | 0.500 | | 1.9229 | 18.9 |
| 8 | 1.481 | 0.800 | | 1.8348 | 42.7 |
| 9 | −2.651 | 0.800 | | | |
| 10 | Reference plane | 0.000 | Eccentricity (1) | | |
| 11 | −3.172 | 1.400 | | 1.8830 | 40.7 |
| 12 | −3.593 | 0.100 | | | |
| 13 | 5.111 | 2.000 | | 1.7620 | 40.1 |
| 14 | −3.683 | 0.800 | | 1.8467 | 23.8 |
| 15 | 58.674 | 0.500 | | | |
| 16 | ∞ | 1.000 | | | |
| 17 | ∞ | 0.100 | | 1.5163 | 64.1 |
| Image plane | ∞ | | Eccentricity (2) | | |

Eccentricity [1]

| X | 1.00 | Y | 0.00 | Z | 0.00 |
|---|---|---|---|---|---|
| α | 0.00 | β | 0.00 | γ | 0.00 |

Eccentricity [2]

| X | −0.70 | Y | 0.00 | Z | 0.00 |
|---|---|---|---|---|---|
| α | 0.00 | β | 0.00 | γ | 0.00 |

Specifications

| | |
|---|---|
| Base length (entrance pupil interval) | 2 mm |
| Angle of view (diagonal) | 120° |
| Stop diameter | φ0.9 mm |
| Image size | φ1.00 mm |
| Focal distance | 1.107 mm |
| Effective Fno | 3.560 |

Example 6

| Surface No. | Radius of curvature | Surface separation | Eccentricity | Refractive index | Abbe number |
|---|---|---|---|---|---|
| Object plane | ∞ | 16.000 | | | |
| 1 | ∞ | 0.600 | | 1.8830 | 40.7 |
| 2 | 2.255 | 1.167 | | | |
| 3 | −4.055 | 0.600 | | 1.8830 | 40.7 |
| 4 | 3.656 | 1.600 | | 1.9229 | 18.9 |
| 5 | −6.965 | 12.026 | | | |
| 6 | 100.005 | 0.600 | | 1.5481 | 45.8 |
| 7 | 1.473 | 1.200 | | 1.5400 | 59.4 |
| 8 | −7.807 | 0.200 | | | |
| 9 | Stop plane | 0.300 | Eccentricity (1) | Glass material (1) | |
| 10 | ∞ | 0.300 | Eccentricity (2) | | |
| 11 | −3.278 | 0.800 | | 1.9229 | 18.9 |
| 12 | −3.472 | 0.300 | | | |
| 13 | Reference plane | 0.000 | Eccentricity (3) | | |
| 14 | 11.239 | 5.000 | Eccentricity (3) | 1.6400 | 60.1 |
| 15 | −4.949 | 0.800 | | 1.6398 | 34.5 |
| 16 | 33.704 | 5.707 | | | |
| 17 | 5.562 | 2.200 | | 1.9229 | 18.9 |
| 18 | 151.444 | 0.500 | | | |
| 19 | ∞ | 1.000 | | 1.5163 | 64.1 |
| 20 | ∞ | 0.100 | | | |
| Image plane | ∞ | | Eccentricity (4) | | |

| | No separation | First pupil E1 | Second pupil E2 |
|---|---|---|---|
| Surface separation of eighth surface | | | |
| d8 | 0.20 | 0.20 | 0.10 |
| Surface separation of ninth surface | | | |
| d9 | 0.30 | 0.30 | 0.40 |
| Curvature radius of tenth surface | | | |
| R10 | ∞ | −202.184 | −202.184 |
| Glass material of ninth surface (1) | | | |
| Refractive index 9 | 1.0000 | 1.8830 | 1.8830 |
| Abbe number 9 | | 40.7 | 40.7 |

| Eccentricity [1] | | | |
|---|---|---|---|
| X | 0.00 | 0.50 | −0.50 |
| β | 0.00 | 0.00 | −13.67 |
| Eccentricity [2] | | | |
| X | 0.00 | 0.50 | −0.50 |
| β | 0.00 | 0.00 | −2.12 |

| Eccentricity [3] | | | | | |
|---|---|---|---|---|---|
| X | 3.00 | Y | 0.00 | Z | 0.00 |
| β | 0.00 | β | 0.00 | γ | 0.00 |
| Eccentricity [4] | | | | | |
| X | −0.70 | Y | 0.00 | Z | 0.00 |
| β | 0.00 | β | 0.00 | γ | 0.00 |

Specifications

| | First pupil E1 | Second pupil E2 |
|---|---|---|
| Base length (entrance pupil interval) | 6 mm | 0.135 mm |
| Angle of view (diagonal) | 140° | |
| Stop diameter | φ2.0 mm | φ1.0 mm | φ1.0 mm |
| Image size | φ1.00 | | |
| Focal distance | 1.040 mm | 1.057 mm | 1.058 mm |
| Effective Fno | 3.85 | 7.84 | 8.07 |

Example 7

| Surface No. | Radius of curvature | Surface separation | Eccentricity | Refractive index | Abbe number |
|---|---|---|---|---|---|
| Object plane | ∞ | 16.000 | | | |
| 1 | ∞ | 0.600 | | 1.8830 | 40.7 |
| 2 | 1.684 | 0.900 | | | |
| 3 | −3.162 | 0.600 | | 1.8830 | 40.7 |
| 4 | 2.965 | 1.600 | | 1.9229 | 18.9 |
| 5 | −4.780 | 5.255 | | | |
| 6 | 16.321 | 0.600 | | 1.6668 | 33.0 |
| 7 | 1.575 | 1.600 | | 1.5638 | 60.6 |
| 8 | −3.483 | 0.200 | | | |
| 9 | Stop plane | 0.300 | Eccentricity (1) | Glass material (1) | |
| 10 | ∞ | 0.300 | Eccentricity (2) | | |
| 11 | −2.604 | 0.800 | | 1.9229 | 18.9 |
| 12 | −2.726 | 0.300 | | | |
| 13 | Reference plane | 0.000 | Eccentricity (3) | | |
| 14 | 8.115 | 2.800 | | 1.6935 | 53.2 |
| 15 | −3.245 | 0.800 | | 1.6889 | 31.1 |
| 16 | 6.452 | 2.914 | | | |
| 17 | 4.652 | 1.600 | | 1.9229 | 18.9 |
| 18 | −66.351 | 0.500 | | | |
| 19 | ∞ | 1.000 | | 1.5163 | 64.1 |
| 20 | ∞ | 0.100 | | | |
| Image plane | ∞ | | Eccentricity (4) | | |

| | No separation | First pupil E1 | Second pupil E2 |
|---|---|---|---|
| Surface separation of eighth surface | | | |
| d8 | 0.20 | 0.10 | 0.20 |
| Surface separation of ninth surface | | | |
| d9 | 0.30 | 0.40 | 0.30 |
| Curvature radius of tenth surface | | | |
| d10 | ∞ | −202.184 | −202.184 |
| Glass material of ninth surface (1) | | | |
| Refractive index 9 | 1.0000 | 1.8830 | 1.8830 |
| Abbe number 9 | | 40.7 | 40.7 |

| Eccentricity [1] | | | |
|---|---|---|---|
| X | 0.00 | 0.50 | −0.50 |
| β | 0.00 | 0.00 | −13.666 |
| Eccentricity [2] | | | |
| X | 0.00 | 0.50 | −0.50 |
| β | 0.00 | 0.00 | −2.120 |

| Eccentricity [3] | | | | | |
|---|---|---|---|---|---|
| X | 1.50 | Y | 0.00 | Z | 0.00 |
| α | 0.00 | β | 0.00 | γ | 0.00 |
| Eccentricity [4] | | | | | |
| X | −0.70 | Y | 0.00 | Z | 0.00 |
| α | 0.00 | β | 0.00 | γ | 0.00 |

-continued

Specifications

|  | First pupil E1 | Second pupil E2 |
|---|---|---|
| Base length (entrance pupil interval) | 3 mm | 0.152 mm |
| Angle of view (diagonal) | 140° |  |
| Stop diameter | φ1.6 mm | φ0.8 mm  φ0.8 mm |
| Image size | φ1.00 |  |
| Focal distance | 1.032 mm | 1.029 mm  1.033 mm |
| Effective Fno | 3.40 | 6.83  6.94 |

Example 8

| Surface No. | Radius of curvature | Surface separation | Eccentricity | Refractive index | Abbe number |
|---|---|---|---|---|---|
| Object plane | ∞ | 20.000 |  |  |  |
| 1 | ∞ | 0.500 |  | 1.8830 | 40.7 |
| 2 | Aspheric surface [1] | 1.439 |  |  |  |
| 3 | −39.792 | 0.500 |  | 1.8830 | 40.7 |
| 4 | 1.534 | 0.900 |  | 1.7847 | 25.7 |
| 5 | −4.963 | 0.100 |  |  |  |
| 6 | 4.316 | 0.500 |  | 1.9229 | 18.9 |
| 7 | 1.596 | 0.900 |  | 1.5831 | 59.4 |
| 8 | −1.806 | 0.050 |  |  |  |
| 9 | Stop plane | 0.000 |  |  |  |
| 10 | Reference plane | 0.000 | Eccentricity (1) |  |  |
| 11 | 2.834 | 1.200 |  | 1.5831 | 59.4 |
| 12 | −46.290 | 0.878 |  |  |  |
| 13 | −40.929 | 0.600 |  | 1.9229 | 18.9 |
| 14 | 5.915 | 0.383 |  |  |  |
| 15 | ∞ | 1.100 | Eccentricity (2) | 1.5163 | 64.1 |
| 16 | ∞ | 0.150 | Eccentricity (3) |  |  |
| Image plane | ∞ |  | Eccentricity (3) |  |  |

Aspheric surface [1]

| Radius curvature | 0.717 |
|---|---|
| k | −2.2311e−001 |

Eccentricity [1]

| X | 1.000 | Y | 0.000 | Z | 0.000 |
|---|---|---|---|---|---|
| α | 0.000 | β | 0.000 | γ | 0.000 |

Eccentricity [2]

| X | −0.600 | Y | 0.000 | Z | 0.000 |
|---|---|---|---|---|---|
| α | 0.000 | β | 19.443 | γ | 0.000 |

Eccentricity [3]

| X | −0.600 | Y | 0.000 | Z | 0.000 |
|---|---|---|---|---|---|
| α | 0.000 | β | 0.000 | γ | 0.000 |

Specifications

| Base length (entrance pupil interval) | 2.0 mm |
|---|---|
| Angle of view (diagonal) | 90° |
| Stop diameter | φ1.05 mm |
| Image size | φ1.41 mm (1.00 × 1.00) |
| Focal distance | 0.809 mm |
| Effective Fno | 3.422 |

Example 9

| Surface No. | Radius of curvature | Surface separation | Eccentricity | Refractive index | Abbe number |
|---|---|---|---|---|---|
| Object plane | ∞ | 20.000 |  |  |  |
| 1 | ∞ | 0.500 |  | 1.8830 | 40.7 |
| 2 | Aspheric surface [1] | 0.286 |  |  |  |
| 3 | −3.513 | 0.500 |  | 1.8830 | 40.7 |
| 4 | 1.534 | 0.900 |  | 1.8591 | 20.1 |
| 5 | −2.632 | 0.434 |  |  |  |
| 6 | −1.826 | 0.500 |  | 1.8927 | 31.6 |
| 7 | 1.534 | 0.900 |  | 1.4875 | 70.4 |
| 8 | −1.664 | 0.050 |  |  |  |
| 9 | 16.256 | 0.800 |  | 1.5589 | 64.0 |
| 10 | −1.792 | 0.000 |  |  |  |
| 11 | Stop plane | 0.000 |  |  |  |
| 12 | Reference plane | 0.000 | Eccentricity (1) |  |  |
| 13 | 3.533 | 1.500 |  | 1.6204 | 60.3 |
| 14 | −3.617 | 0.800 |  | 1.5739 | 37.6 |
| 15 | 7.980 | 1.580 |  |  |  |
| 16 | ∞ | 1.100 | Eccentricity (2) | 1.5163 | 64.1 |
| 17 | ∞ | 0.150 | Eccentricity (3) |  |  |
| Image plane | ∞ |  | Eccentricity (3) |  |  |

Aspheric surface [1]

| Radius curvature | 0.989 |
|---|---|
| k | 7.8037e−001 |

Eccentricity [1]

| X | 1.100 | Y | 0.000 | Z | 0.000 |
|---|---|---|---|---|---|
| α | 0.000 | β | 0.000 | γ | 0.000 |

Eccentricity [2]

| X | −0.600 | Y | 0.000 | Z | 0.000 |
|---|---|---|---|---|---|
| α | 0.000 | β | 18.532 | γ | 0.000 |

Eccentricity [3]

| X | −0.600 | Y | 0.000 | Z | 0.000 |
|---|---|---|---|---|---|
| α | 0.000 | β | 0.000 | γ | 0.000 |

Specifications

| Base length (entrance pupil interval) | 2.2 mm |
|---|---|
| Angle of view (diagonal) | 90° |
| Stop diameter | φ1.15 mm |
| Image size | φ1.41 mm (1.00 × 1.00) |
| Focal distance | 0.828 mm |
| Effective Fno | 3.55 |

Example 10

| Surface No. | Radius of curvature | Surface separation | Eccentricity | Refractive index | Abbe number |
|---|---|---|---|---|---|
| Object plane | ∞ | 20.000 |  |  |  |
| 1 | ∞ | 0.500 |  | 1.8830 | 40.7 |
| 2 | Aspheric surface [1] | 0.310 |  |  |  |
| 3 | −13.875 | 0.500 |  | 1.8830 | 40.7 |
| 4 | 1.534 | 0.900 |  | 1.9229 | 18.9 |
| 5 | −2.178 | 0.100 |  |  |  |

-continued

| 6 | −1.493 | 0.500 | | 1.8952 | 29.8 |
| 7 | 1.534 | 0.900 | | 1.5714 | 63.1 |
| 8 | −1.727 | 0.050 | | | |
| 9 | 17.392 | 0.800 | | 1.4983 | 69.2 |
| 10 | −1.738 | 0.000 | | | |
| 11 | Stop plane | 0.000 | | | |
| 12 | Reference plane | 0.000 | Eccentricity (1) | | |
| 13 | 4.077 | 1.500 | | 1.5539 | 64.4 |
| 14 | −2.378 | 0.800 | | 1.5659 | 42.4 |
| 15 | −23.139 | 1.298 | | | |
| 16 | FFS[1] | 1.100 | Eccentricity (2) | 1.5163 | 64.1 |
| 17 | ∞ | 0.150 | Eccentricity (3) | | |
| Image plane | ∞ | | Eccentricity (3) | | |

Aspheric surface [1]

| Radius curvature | 0.851 |
|---|---|
| k | −7.6361e−002 |

FES [1]

| C4 | 2.0964e−001 | C6 | 1.6540e−001 | C7 | 4.9915e−024 |
| C9 | 5.6305e−023 | C67 | 8.0000e+000 | | |

Eccentricity [1]

| X | 1.100 | Y | 0.000 | Z | 0.000 |
| α | 0.000 | β | 0.000 | γ | 0.000 |

Eccentricity [2]

| X | −0.600 | Y | 0.000 | Z | 0.000 |
| α | 0.000 | β | 11.462 | γ | 0.000 |

Eccentricity [3]

| X | −0.600 | Y | 0.000 | Z | 0.000 |
| α | 0.000 | β | 0.000 | γ | 0.000 |

Specifications

| Base length (entrance pupil interval) | 2.2 mm |
|---|---|
| Angle of view (diagonal) | 90° |
| Stop diameter | φ1.15 mm |
| Image size | φ1.41 mm(1.00 × 1.00) |
| Imaging plane size | φ2.42 |
| Focal distance | 0.914 mm |
| Effective Fno | 3.37 |

Conditional formulas (1) and (2) for the above Examples 1 to 10 are given below.

| Conditional formula | Example 1 | Example 2 | Example 3 | Example 4 |
|---|---|---|---|---|
| (1) FAb/f | 15.723 | 12.444 | 7.805 | 36.816 |
| (2) Lb/f | 1.448 | 1.546 | 1.530 | 1.538 |

| Conditional formula | Example 5 | Example 6 | Example 7 | Example 8 |
|---|---|---|---|---|
| (1) FAb/f | 12.491 | 4.525 | 4.459 | 9.951 |
| (2) Lb/f | 1.551 | 0.871 | 1.144 | 2.019 |

| Conditional formula | Example 9 | Example 10 |
|---|---|---|
| (1) FAb/f | 11.964 | 9.239 |
| (2) Lb/f | 3.418 | 2.788 |

The following describes application examples of the optical system 1 according to the present embodiment.

Figure 45A:
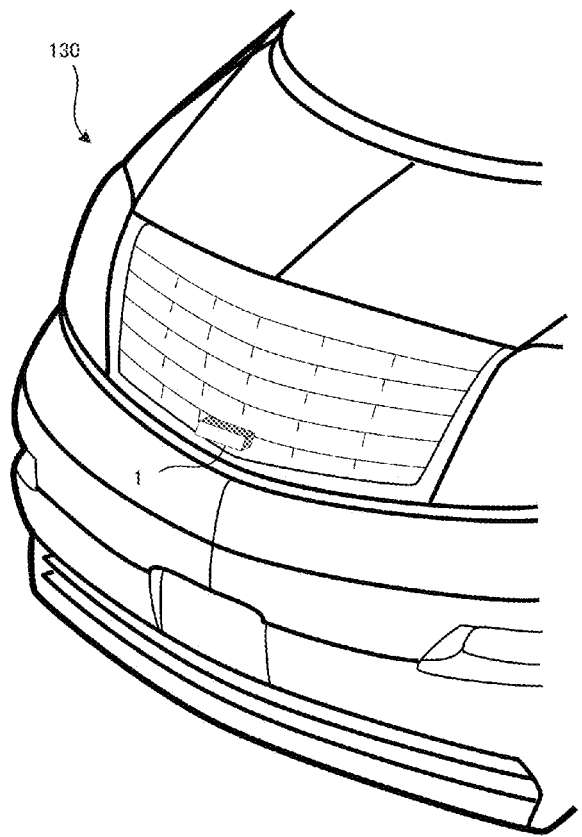
FIGS. 45A and 45B are views illustrating an example in which the optical system according to the present embodiment is used as an on-vehicle imaging device.
Figure 45B:
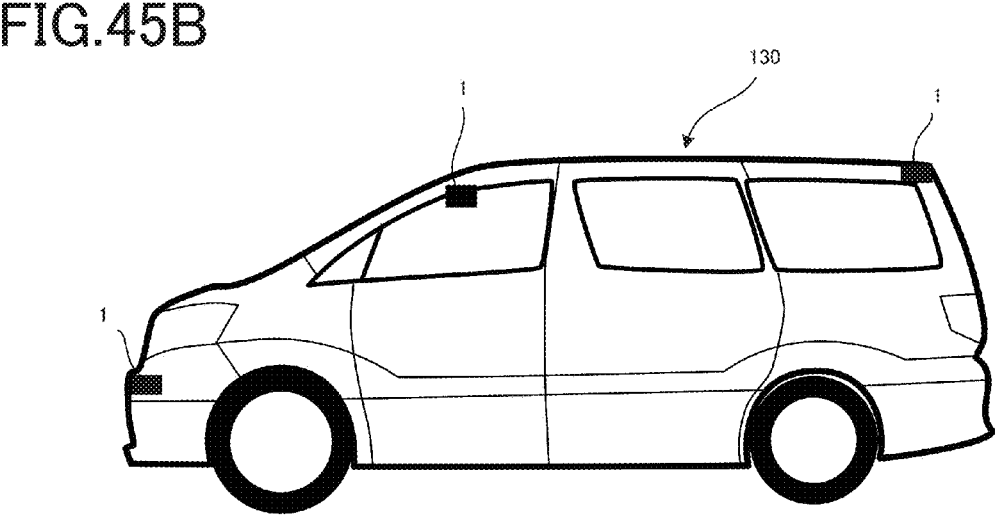

FIGS. 45A and 45B are views illustrating an example in which the optical system according to the present embodiment is used as an on-vehicle imaging device.

FIG. 45A is a view illustrating an example in which, the optical system 1 according to the present embodiment is mounted as an imaging device on the front of an automobile 130 so that images taken via the respective optical systems 1 are simultaneously displayed on an in-vehicle display device after distortion correction by image processing. FIG. 45B is a view illustrating an example in which a plurality of optical systems 1 according to the present embodiment are attached as an imaging device to the corners of the automobile 130 or the top of a pole of a head portion thereof so that images taken via the respective optical systems 1 are simultaneously displayed in a stereoscopic manner on the in-vehicle display device after distortion correction through image processing.

Figure 46A:
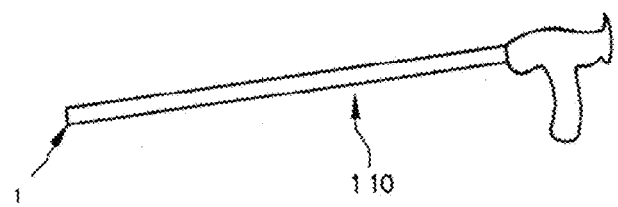
FIGS. 46A to 46C are views illustrating an example in which the optical system according to the present embodiment is used as an imaging optical system to be attached to a distal end of an endoscope.
Figure 46B:
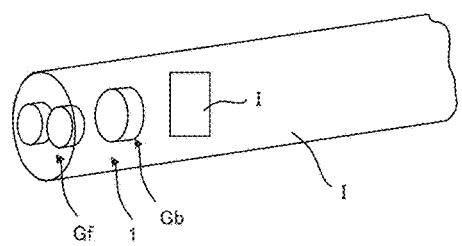
Figure 46C:
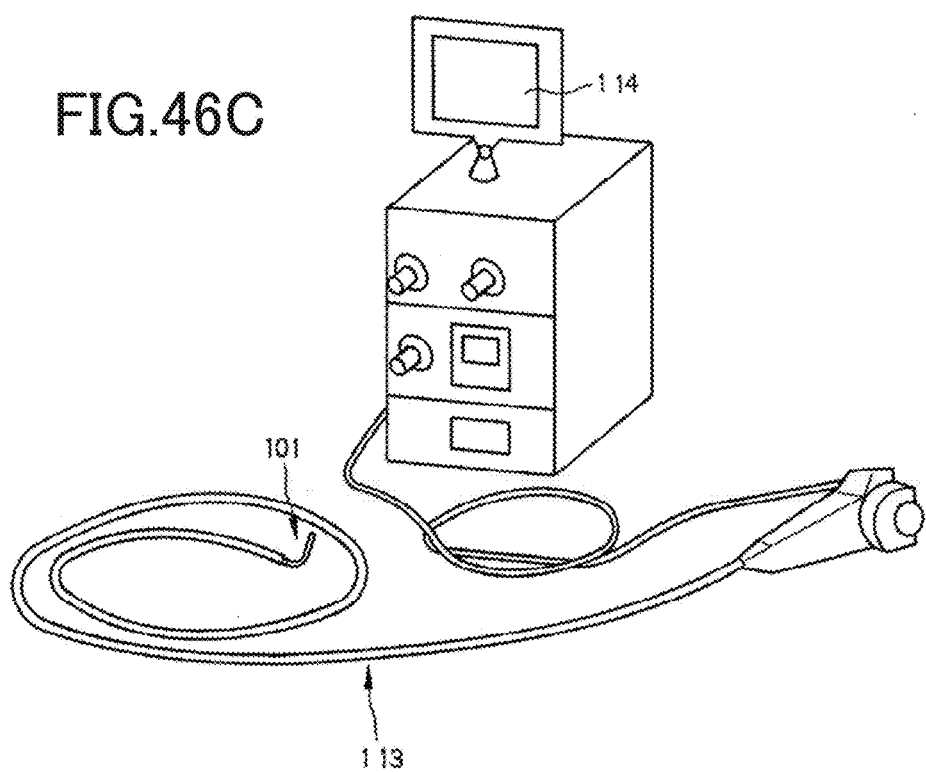

FIGS. 46A to 46C are views for illustrating an example in which the optical system according to the present embodiment is used as an imaging optical system to be attached to a distal end of an endoscope.

FIGS. 46A to 46C are views for illustrating an example in which the optical system 1 according to the present embodiment is used as an imaging optical system to be attached to a distal end of an endoscope. FIG. 46A is an example in which the optical system 1 is attached to a distal end of a rigid endoscope 110 for stereoscopic imaging/observation of an omnidirectional image. FIG. 46B illustrates a schematic configuration of the distal end of the rigid endoscope 110. FIG. 46C is an example in which the optical system 1 according to the present embodiment of the invention is attached to a distal end of a soft electronic endoscope 113 so that images taken are stereoscopically displayed on a display device 114 after distortion correction through image processing.

Using the optical system 1 for the endoscope as illustrated in FIGS. 46A to 46C, it is possible to stereoscopically image/observe an omnidirectional image and stereoscopically image/observe various regions from angles different from conventional one.

While various embodiments of the invention have been described, it is understood that the invention is not limited only thereto: changes or modifications made to the constructions of such embodiments or some combinations thereof are embraced in the invention as well.

REFERENCE SIGNS LIST

1: Optical system
Gf: Front lens group
Gb: Back lens group
S1: First stop
S2: Second stop
I: Image plane

The invention claimed is:

1. An optical system comprising, in order from an object side to an image plane side:
   a front group including a first front group arranged centering a first front central axis and a second front group arranged centering a second front group central axis extending parallel to the first front group central axis; and
   a back group arranged centering a single back group central axis,
   wherein:
   a central principal ray of a first light beam that has passed through the first front group and a central principal ray of a second light beam that has passed through the second front group do not cross each other from when they exit from the first and second front groups, respectively, to when they reach the image plane, the first and second light beams are convergent light beams along an entirety of their respective exit paths from the first and second front groups, and the first and second light beams remain convergent and do not cross each other from when they exit from the first and second front groups, respectively, to when they reach the image plane, an interval between the first and second front group central axes is larger than an interval between the centers of the first and second light beams at the image plane, and the first and second front groups each include a stop.

2. The optical system according to claim 1, further comprising a back deflection group disposed between the back group and the image plane and configured to deflect the first and second light beams, wherein the back deflection group performs deflection so as to reduce convergence of the first and second light beams that have exited from the back group and to make an absolute value of an incident angle of the first and second light beams onto the image plane smaller than an absolute value of an incident angle thereof onto the back deflection group.

3. The optical system according to claim 2, wherein the back deflection group includes a first back deflection group that deflects the first light beam and a second back deflection group that deflects the second light beam.

4. The optical system according to claim 2, wherein the back deflection group includes a back deflection member, and wherein the back deflection member comprises an optical device having a thickness in a direction of the back group central axis which increases toward an outer peripheral side with respect to the back group central axis.

5. The optical system according to claim 4, wherein the back deflection member comprises an optical device having a wedge prism shape.

6. The optical system according to claim 4, wherein the back deflection member includes a curved surface.

7. The optical system according to claim 2, wherein the back deflection group includes a diffraction optical device.

8. An optical system comprising, in order from an object side to an image plane side:

a front group including a first front group arranged centering a first front central axis and a second front group arranged centering a second front group central axis extending parallel to the first front group central axis; and a back group arranged centering a single back group central axis, wherein:

a central principal ray of a first light beam that has passed through the first front group and a central principal ray of a second light beam that has passed through the second front group do not cross each other from when they exit from the first and second front groups, respectively, to when they reach the image plane, the first and second light beams are convergent light beams that do not cross each other from when they exit from the first and second front groups, respectively, to when they reach the image plane, an interval between the first and second front group central axes is larger than an interval between the centers of the first and second light beams at the image plane, the first and second front groups each include a stop, and the first and second front groups each include, in order from the object side to image plane side, a front first group having a negative refractive power and a front second group including a cemented positive lens.

9. The optical system according to claim 8, wherein the front first group includes a flat-concave negative lens whose flat surface faces the object side, and wherein the cemented lens of the front second group includes a cemented positive meniscus lens whose convex surface faces the object side.

10. The optical system according to claim 8, wherein the first and second front groups each include, on the back group side of the front second group thereof, a front third group including a cemented positive lens different from that of the front second group.

11. The optical system according to claim 1, satisfying the following conditional formula (1):

$$FAb/f<50 \qquad (1)$$

where FAb is a distance from a final surface of the front group to an image formation position at which light beams exiting from the front group are image-formed, and f is a focal distance of the entire optical system.

12. The optical system according to claim 1, satisfying the following conditional formula (2):

$$Lb/f<5 \qquad (2)$$

where Lb is a distance from a final surface of the back group to the image plane, and f is a focal distance of the entire optical system.

13. The optical system according to claim 1, further comprising:

a shielding member disposed in the first front group so as to shield the first light beam; and a pupil dividing member disposed in the second front group so as to deflect the second light beam.

14. The optical system according to claim 13, wherein the pupil dividing member includes a first pupil that forms an image of a part of the second light beam without deflecting it and a second pupil that forms an image of the remaining part of the second light beam at a position different from a position at which the image is formed by the first pupil, on the same plane as the plane on which the image formed by the first pupil is formed.

15. The optical system according to claim 13, wherein the pupil dividing member has a positive refractive power, and wherein an image formation position upon near-point observation obtained without use of the pupil dividing member and an image formation position upon far-point observation obtained with use of the pupil dividing member are the same.

16. The optical system according to claim 13, wherein the shielding member and the pupil dividing member are disposed in opposition to each other between their corresponding lenses of the first front group and second front group, respectively.

17. A stereoscopic imaging device comprising:

the optical system as claimed in claim 1; and an imaging device.

18. The stereoscopic imaging device according to claim 17, wherein the imaging device includes a single device.

19. An endoscope comprising the stereoscopic imaging device as claimed in claim 17.

* * * * *